US005643356A

United States Patent [19]
Nohr et al.

[11] Patent Number: 5,643,356
[45] Date of Patent: Jul. 1, 1997

[54] INK FOR INK JET PRINTERS

[75] Inventors: Ronald Sinclair Nohr, Alpharetta; John Gavin MacDonald, Decatur, both of Ga.

[73] Assignee: Kimberly-Clark Corporation, Neenah, Wis.

[21] Appl. No.: 465,377

[22] Filed: Jun. 5, 1995

Related U.S. Application Data

[63] Continuation-in-part of Ser. No. 403,240, Mar. 10, 1995, abandoned, which is a continuation-in-part of Ser. No. 373,958, Jan. 17, 1995, which is a continuation-in-part of Ser. No. 360,501, Dec. 21, 1994, and Ser. No. 359,670, Dec. 20, 1994, abandoned, which is a continuation-in-part of Ser. No. 336,813, Nov. 9, 1994, abandoned, and Ser. No. 258, 858, Jun. 13, 1994, abandoned, which is a continuation-in-part of Ser. No. 119,912, Sep. 10, 1993, abandoned, which is a continuation-in-part of Ser. No. 103,503, Aug. 5, 1993, abandoned, said Ser. No. 360,501, is a continuation-in-part of Ser. No. 336,813, and Ser. No. 258,858.

[51] Int. Cl.[6] ............................................. C09D 11/02
[52] U.S. Cl. .......................... 106/31.49; 347/86; 347/96; 347/100; 430/347; 430/339; 430/340; 430/343; 522/75; 522/79; 522/141; 106/31.78
[58] Field of Search ............................... 106/20 A, 23 B, 106/22 B, 21 A, 20 D, 20 C; 347/86, 100, 96; 430/347, 339, 340, 343

[56] References Cited

U.S. PATENT DOCUMENTS

| 28,225 | 11/1860 | Heseltine et al. . |
| 28,789 | 4/1860 | Chang . |
| 575,228 | 1/1897 | von Gallois . |
| 582,853 | 5/1897 | Feer . |
| 1,013,544 | 1/1912 | Fuerth . |
| 1,325,971 | 12/1919 | Akashi . |
| 1,364,406 | 1/1921 | Olsen . |
| 1,436,856 | 11/1922 | Brenizer et al. . |
| 1,744,149 | 1/1930 | Staehlin . |
| 1,803,906 | 5/1931 | Krieger et al. . |
| 1,876,880 | 9/1932 | Drapal . |
| 1,880,572 | 10/1932 | Wendt et al. . |
| 1,880,573 | 10/1932 | Wendt et al. . |
| 1,916,350 | 7/1933 | Wendt et al. . |
| 1,916,779 | 7/1933 | Wendt et al. . |
| 1,955,898 | 4/1934 | Wendt et al. . |
| 1,962,111 | 6/1934 | Bamberger . |
| 2,049,005 | 7/1936 | Gaspar . |
| 2,054,390 | 9/1936 | Rust et al. . |
| 2,062,304 | 12/1936 | Gaspar . |
| 2,097,119 | 10/1937 | Eggert . |
| 2,106,539 | 1/1938 | Schnitzspahn . |
| 2,111,692 | 3/1938 | Saunders et al. . |
| 2,125,015 | 7/1938 | Gaspar . |
| 2,130,572 | 9/1938 | Wendt . |
| 2,132,154 | 10/1938 | Gaspar . |
| 2,145,960 | 2/1939 | Wheatley et al. . |
| 2,159,280 | 5/1939 | Mannes et al. . |
| 2,171,976 | 9/1939 | Erickson . |
| 2,185,153 | 12/1939 | Lecher et al. . |
| 2,220,178 | 11/1940 | Schneider . |
| 2,230,590 | 2/1941 | Eggert et al. . |
| 2,237,885 | 4/1941 | Markush et al. . |
| 2,242,431 | 5/1941 | Hara et al. . |
| 2,268,324 | 12/1941 | Polgar . |
| 2,281,895 | 5/1942 | van Poser et al. . |
| 2,328,166 | 8/1943 | Poigar et al. . |
| 2,346,090 | 4/1944 | Staehle . |
| 2,349,090 | 5/1944 | Haddock . |
| 2,356,618 | 8/1944 | Rossander et al. . |
| 2,361,301 | 10/1944 | Libby, Jr. et al. . |
| 2,364,359 | 12/1944 | Kienle et al. . |
| 2,381,145 | 8/1945 | von Glahn et al. . |
| 2,382,904 | 8/1945 | Federsen . |
| 2,386,646 | 10/1945 | Adams et al. . |
| 2,402,106 | 6/1946 | von Glahn et al. . |
| 2,416,145 | 2/1947 | Biro . |
| 2,477,165 | 7/1949 | Bergstrom . |
| 2,527,347 | 10/1950 | Bergstrom . |
| 2,601,669 | 6/1952 | Tullsen . |
| 2,612,494 | 9/1952 | von Glahn et al. . |
| 2,612,495 | 9/1952 | von Glahn et al. . |
| 2,628,959 | 2/1953 | von Glahn et al. . |
| 2,728,784 | 12/1955 | Tholstrup et al. . |
| 2,744,103 | 5/1956 | Koch . |
| 2,757,090 | 7/1956 | Meugebauer et al. . |
| 2,763,550 | 9/1956 | Lovick . |
| 2,768,171 | 10/1956 | Clarke et al. . |
| 2,773,056 | 12/1956 | Helfaer . |

(List continued on next page.)

FOREIGN PATENT DOCUMENTS

| 103085 | 4/1937 | Australia . |
| 620075 | 5/1962 | Belgium . |

(List continued on next page.)

OTHER PUBLICATIONS

Chang et al., "Color Modulated Dye Ink Jet Printer", Oct. 1974, IBM Technical Disclosure Bulletin vol. 17 No. 5 pp. 1520–1521.

Maki, Y. et al. "A novel heterocyclic N–oxide, pyrimido[5, 4–g]pteridinetetrone 5–oxide, with multifunctional" *Chemical Abstracts* 122 925 [No. 122:31350 F] 1995.

(List continued on next page.)

*Primary Examiner*—John A. McPherson
*Attorney, Agent, or Firm*—Jones & Askew

[57] ABSTRACT

An improved ink suitable for ink jet printing comprising, a mixture of a colorant, an arylketoalkene stabilizing compound or a photoreactor, and a liquid vehicle, wherein the colorant is light-stable. When the photoreactor is combined with a wavelength-selective sensitizer to form a radiation transorber, the colorant is mutable upon exposure of the radiation transorber to specific, narrow bandwidth radiation. The colored composition may also contain a molecular includant having a chemical structure which defines at least one cavity wherein each of the colorant and photoreactor or radiation transorber is associated with the molecular includant. The invention also includes ink jet print cartridges containing the improved ink, ink jet printers containing the improved ink and methods of printing using the improved ink.

26 Claims, 5 Drawing Sheets

U.S. PATENT DOCUMENTS

| | | |
|---|---|---|
| 2,798,000 | 7/1957 | Monterman . |
| 2,809,189 | 10/1957 | Stanley et al. . |
| 2,834,773 | 5/1958 | Scalera et al. . |
| 2,897,187 | 7/1959 | Koch . |
| 2,936,241 | 5/1960 | Sharp et al. . |
| 2,992,198 | 7/1961 | Funahashi . |
| 3,030,208 | 4/1962 | Schellenberg et al. . |
| 3,071,815 | 1/1963 | MacKinnon . |
| 3,104,973 | 9/1963 | Sprague et al. . |
| 3,114,634 | 12/1963 | Brown et al. . |
| 3,121,632 | 2/1964 | Sprague et al. . |
| 3,133,049 | 5/1964 | Hertel et al. . |
| 3,140,949 | 7/1964 | Sprague et al. . |
| 3,154,416 | 10/1964 | Fidelman . |
| 3,155,509 | 11/1964 | Roscow . |
| 3,175,905 | 3/1965 | Wiesbaden . |
| 3,178,285 | 4/1965 | Anderau et al. . |
| 3,242,215 | 3/1966 | Heitmiller . |
| 3,284,205 | 11/1966 | Sprague et al. . |
| 3,300,314 | 1/1967 | Rauner et al. . |
| 3,304,297 | 2/1967 | Wegmann et al. . |
| 3,305,361 | 2/1967 | Gaynor et al. . |
| 3,313,797 | 4/1967 | Kissa . |
| 3,359,109 | 12/1967 | Harder et al. . |
| 3,361,827 | 1/1968 | Biletch . |
| 3,385,700 | 5/1968 | Willems et al. . |
| 3,397,984 | 8/1968 | Williams et al. . |
| 3,418,118 | 12/1968 | Thommes et al. . |
| 3,479,185 | 11/1969 | Chambers . |
| 3,502,476 | 3/1970 | Kohei et al. . |
| 3,503,744 | 3/1970 | Itano et al. . |
| 3,514,597 | 5/1970 | Haes et al. . |
| 3,547,646 | 12/1970 | Hori et al. . |
| 3,563,931 | 2/1971 | Horiguchi . |
| 3,574,624 | 4/1971 | Reynolds et al. . |
| 3,595,655 | 7/1971 | Robinson et al. . |
| 3,595,657 | 7/1971 | Robinson et al. . |
| 3,595,658 | 7/1971 | Gerlach et al. . |
| 3,595,659 | 7/1971 | Gerlach et al. . |
| 3,607,639 | 9/1971 | Krefeld et al. . |
| 3,607,693 | 9/1971 | Heine et al. . |
| 3,607,863 | 9/1971 | Dosch . |
| 3,615,562 | 10/1971 | Harrison et al. . |
| 3,617,288 | 11/1971 | Hartman et al. . |
| 3,637,337 | 1/1972 | Pilling . |
| 3,637,581 | 1/1972 | Horioguchi et al. . |
| 3,642,472 | 2/1972 | Mayo . |
| 3,647,467 | 3/1972 | Grubb . |
| 3,667,954 | 6/1972 | Itano et al. . |
| 3,668,188 | 6/1972 | King et al. . |
| 3,669,925 | 6/1972 | King et al. . |
| 3,671,096 | 6/1972 | Mackin . |
| 3,671,251 | 6/1972 | Houle et al. . |
| 3,676,690 | 7/1972 | McMillin et al. . |
| 3,678,044 | 7/1972 | Adams . |
| 3,695,879 | 10/1972 | Laming et al. . |
| 3,697,280 | 10/1972 | Strilko . |
| 3,707,371 | 12/1972 | Files . |
| 3,729,313 | 4/1973 | Smith . |
| 3,737,628 | 6/1973 | Azure . |
| 3,765,896 | 10/1973 | Fox . |
| 3,775,130 | 11/1973 | Enomoto et al. . |
| 3,788,849 | 1/1974 | Taguchi et al. . |
| 3,799,773 | 3/1974 | Watarai et al. . |
| 3,800,439 | 4/1974 | Sokolski et al. . |
| 3,817,752 | 6/1974 | Laridon et al. . |
| 3,840,338 | 10/1974 | Zviak et al. . |
| 3,873,500 | 3/1975 | Kato et al. . |
| 3,887,450 | 6/1975 | Gilano et al. . |
| 3,895,949 | 7/1975 | Akamatsu . |
| 3,914,166 | 10/1975 | Rudolph et al. . |
| 3,915,824 | 10/1975 | McGinniss . |
| 3,919,323 | 11/1975 | Houlihan et al. . |
| 3,978,132 | 8/1976 | Houlihan et al. . |
| 3,984,248 | 10/1976 | Sturmer . |
| 3,988,154 | 10/1976 | Sturmer . |
| 4,012,256 | 3/1977 | Levinos . |
| 4,043,819 | 8/1977 | Baumann . |
| 4,048,034 | 9/1977 | Martan . |
| 4,056,665 | 11/1977 | Tayler et al. . |
| 4,058,400 | 11/1977 | Crivello . |
| 4,067,892 | 1/1978 | Thorne et al. . |
| 4,073,968 | 2/1978 | Miyamoto et al. . |
| 4,079,183 | 3/1978 | Green . |
| 4,090,877 | 5/1978 | Streeper . |
| 4,100,047 | 7/1978 | McCarty . |
| 4,107,733 | 8/1978 | Schickedanz . |
| 4,110,112 | 8/1978 | Roman et al. . |
| 4,111,699 | 9/1978 | Krueger . |
| 4,114,028 | 9/1978 | Baio et al. . |
| 4,148,658 | 4/1979 | Kondoh et al. . |
| 4,162,162 | 7/1979 | Dueber . |
| 4,179,577 | 12/1979 | Green . |
| 4,181,807 | 1/1980 | Green . |
| 4,229,172 | 10/1980 | Baumann et al. . |
| 4,232,106 | 11/1980 | Iwasaki et al. . |
| 4,239,843 | 12/1980 | Hara et al. . |
| 4,241,155 | 12/1980 | Hara et al. . |
| 4,242,430 | 12/1980 | Hara et al. . |
| 4,245,018 | 1/1981 | Hara et al. . |
| 4,245,995 | 1/1981 | Hugl et al. . |
| 4,246,330 | 1/1981 | Hara et al. . |
| 4,248,949 | 2/1981 | Hara et al. . |
| 4,250,096 | 2/1981 | Kvita et al. . |
| 4,251,622 | 2/1981 | Kimoto et al. . |
| 4,254,195 | 3/1981 | Hara et al. . |
| 4,256,493 | 3/1981 | Yokoyama et al. . |
| 4,256,817 | 3/1981 | Hara et al. . |
| 4,259,432 | 3/1981 | Kondoh et al. . |
| 4,262,936 | 4/1981 | Miyamoto . |
| 4,268,605 | 5/1981 | Hara et al. . |
| 4,268,667 | 5/1981 | Anderson . |
| 4,269,926 | 5/1981 | Hara et al. . |
| 4,270,130 | 5/1981 | Houle et al. . |
| 4,271,252 | 6/1981 | Hara et al. . |
| 4,271,253 | 6/1981 | Hara et al. . |
| 4,272,244 | 6/1981 | Schlick . |
| 4,279,982 | 7/1981 | Iwasaki et al. . |
| 4,279,985 | 7/1981 | Nonogaki et al. . |
| 4,284,485 | 8/1981 | Berner . |
| 4,289,844 | 9/1981 | Specht et al. . |
| 4,290,870 | 9/1981 | Kondoh et al. . |
| 4,300,123 | 11/1981 | McMillin et al. . |
| 4,306,014 | 12/1981 | Kunikane et al. . |
| 4,307,182 | 12/1981 | Dalzell et al. . |
| 4,308,400 | 12/1981 | Felder et al. . |
| 4,315,807 | 2/1982 | Felder et al. . |
| 4,318,705 | 3/1982 | Nowak et al. . |
| 4,318,791 | 3/1982 | Felder et al. . |
| 4,335,054 | 6/1982 | Blaser et al. . |
| 4,335,055 | 6/1982 | Blaser et al. . |
| 4,336,323 | 6/1982 | Winslow . |
| 4,343,891 | 8/1982 | Aasen et al. . |
| 4,345,011 | 8/1982 | Drexhage . |
| 4,347,111 | 8/1982 | Gehlhaus et al. . |
| 4,349,617 | 9/1982 | Kawashiri et al. . |
| 4,350,753 | 9/1982 | Shelnut et al. . |
| 4,351,893 | 9/1982 | Anderson . |
| 4,356,255 | 10/1982 | Tachikawa et al. . |
| 4,359,524 | 11/1982 | Masuda et al. . |
| 4,362,806 | 12/1982 | Whitmore . |
| 4,367,072 | 1/1983 | Vogtle et al. . |

| | | |
|---|---|---|
| 4,367,280 | 1/1983 | Kondo et al. . |
| 4,369,283 | 1/1983 | Altschuler . |
| 4,370,401 | 1/1983 | Winslow et al. . |
| 4,373,020 | 2/1983 | Winslow . |
| 4,376,887 | 3/1983 | Greenaway et al. . |
| 4,390,616 | 6/1983 | Sato et al. . |
| 4,391,867 | 7/1983 | Derick et al. . |
| 4,399,209 | 8/1983 | Sanders et al. . |
| 4,416,961 | 11/1983 | Drexhage . |
| 4,424,325 | 1/1984 | Tsunoda et al. . |
| 4,425,162 | 1/1984 | Sugiyama et al. . |
| 4,425,424 | 1/1984 | Altland et al. . |
| 4,434,035 | 2/1984 | Eichler et al. . |
| 4,447,521 | 5/1984 | Tiers et al. . |
| 4,450,227 | 5/1984 | Holmes et al. . |
| 4,460,676 | 7/1984 | Fabel . |
| 4,467,112 | 8/1984 | Matsuura et al. . |
| 4,475,999 | 10/1984 | Via . |
| 4,496,447 | 1/1985 | Eichler et al. . |
| 4,510,392 | 4/1985 | Litt et al. . |
| 4,523,924 | 6/1985 | Lacroix . |
| 4,524,122 | 6/1985 | Weber et al. . |
| 4,548,896 | 10/1985 | Sabongi et al. . |
| 4,555,474 | 11/1985 | Kawamura . |
| 4,565,769 | 1/1986 | Dueber et al. . |
| 4,567,171 | 1/1986 | Mangum . |
| 4,571,377 | 2/1986 | McGinniss et al. . |
| 4,595,745 | 6/1986 | Nakano et al. . |
| 4,604,344 | 8/1986 | Irving et al. . |
| 4,613,334 | 9/1986 | Thomas et al. . |
| 4,617,380 | 10/1986 | Hinson et al. . |
| 4,622,286 | 11/1986 | Sheets . |
| 4,632,891 | 12/1986 | Banks et al. . |
| 4,632,895 | 12/1986 | Patel et al. . |
| 4,634,644 | 1/1987 | Irving et al. . |
| 4,638,340 | 1/1987 | Iiyama et al. . |
| 4,663,275 | 5/1987 | West et al. . |
| 4,663,641 | 5/1987 | Iiyama et al. . |
| 4,668,533 | 5/1987 | Miller . |
| 4,672,041 | 6/1987 | Jain . |
| 4,698,291 | 10/1987 | Koibuchi et al. . |
| 4,701,402 | 10/1987 | Patel et al. . |
| 4,702,996 | 10/1987 | Griffing et al. . |
| 4,707,161 | 11/1987 | Thomas et al. . |
| 4,707,425 | 11/1987 | Sasagawa et al. . |
| 4,707,430 | 11/1987 | Ozawa et al. . |
| 4,720,450 | 1/1988 | Ellis . |
| 4,721,734 | 1/1988 | Gehlhaus et al. . |
| 4,724,021 | 2/1988 | Martin et al. . |
| 4,724,201 | 2/1988 | Okazaki et al. . |
| 4,725,527 | 2/1988 | Robillard . |
| 4,737,438 | 4/1988 | Ito et al. . |
| 4,740,451 | 4/1988 | Kohara . |
| 4,745,042 | 5/1988 | Sasago et al. . |
| 4,755,450 | 7/1988 | Sanders et al. . |
| 4,761,181 | 8/1988 | Suzuki . |
| 4,766,050 | 8/1988 | Jerry . |
| 4,766,055 | 8/1988 | Kawabata et al. . |
| 4,771,802 | 9/1988 | Tannenbaum . |
| 4,772,291 | 9/1988 | Shibanai et al. . |
| 4,772,541 | 9/1988 | Gottschalk . |
| 4,775,386 | 10/1988 | Reinert et al. . |
| 4,786,586 | 11/1988 | Lee et al. . |
| 4,800,149 | 1/1989 | Gottschalk . |
| 4,808,189 | 2/1989 | Oishi et al. . |
| 4,812,139 | 3/1989 | Brodmann . |
| 4,812,517 | 3/1989 | West . |
| 4,813,970 | 3/1989 | Kirjanov et al. . |
| 4,822,714 | 4/1989 | Sanders . |
| 4,837,106 | 6/1989 | Ishikawa et al. . |
| 4,837,331 | 6/1989 | Yamanishi et al. . |
| 4,838,938 | 6/1989 | Tomida et al. . |
| 4,839,269 | 6/1989 | Okazaki et al. . |
| 4,849,320 | 7/1989 | Irving et al. . |
| 4,853,395 | 8/1989 | Carr et al. . |
| 4,853,398 | 8/1989 | Carr et al. . |
| 4,857,438 | 8/1989 | Loerzer et al. . |
| 4,861,916 | 8/1989 | Kohler et al. . |
| 4,865,942 | 9/1989 | Gottschalk et al. . |
| 4,874,391 | 10/1989 | Reinert . |
| 4,895,880 | 1/1990 | Gottschalk . |
| 4,900,581 | 2/1990 | Stuke et al. . |
| 4,902,299 | 2/1990 | Anton . |
| 4,902,725 | 2/1990 | Moore . |
| 4,902,787 | 2/1990 | Freeman . |
| 4,925,770 | 5/1990 | Ichiura et al. . |
| 4,933,948 | 6/1990 | Herkstroeter . |
| 4,937,161 | 6/1990 | Kita et al. . |
| 4,942,113 | 7/1990 | Trundle . |
| 4,952,680 | 8/1990 | Schmeidl . |
| 4,954,380 | 9/1990 | Kanome et al. . |
| 4,956,254 | 9/1990 | Washizu et al. . |
| 4,968,813 | 11/1990 | Rule et al. . |
| 4,985,345 | 1/1991 | Hayakawa et al. . |
| 4,987,056 | 1/1991 | Imahashi et al. . |
| 4,997,745 | 3/1991 | Kawamura et al. . |
| 5,001,330 | 3/1991 | Koch . |
| 5,002,853 | 3/1991 | Aoai et al. . |
| 5,002,993 | 3/1991 | West et al. . |
| 5,003,142 | 3/1991 | Fuller . |
| 5,006,758 | 4/1991 | Gellert et al. . |
| 5,013,959 | 5/1991 | Kogelschatz . |
| 5,023,129 | 6/1991 | Morganti et al. . |
| 5,025,036 | 6/1991 | Carson et al. . |
| 5,026,427 | 6/1991 | Mitchell et al. . |
| 5,028,792 | 7/1991 | Mullis . |
| 5,034,526 | 7/1991 | Bonham et al. . |
| 5,045,435 | 9/1991 | Adams et al. . |
| 5,045,573 | 9/1991 | Kohler et al. . |
| 5,053,320 | 10/1991 | Robbillard . |
| 5,055,579 | 10/1991 | Pawlowski et al. . |
| 5,070,001 | 12/1991 | Stahlhofen . |
| 5,076,808 | 12/1991 | Hahn et al. . |
| 5,085,698 | 2/1992 | Ma et al. . |
| 5,087,550 | 2/1992 | Blum et al. . |
| 5,089,374 | 2/1992 | Saeva . |
| 5,096,489 | 3/1992 | Laver . |
| 5,098,806 | 3/1992 | Robillard . |
| 5,106,723 | 4/1992 | West et al. . |
| 5,108,505 | 4/1992 | Moffatt ........................ 106/25 |
| 5,108,874 | 4/1992 | Griffing et al. . |
| 5,110,706 | 5/1992 | Yumoto et al. . |
| 5,110,709 | 5/1992 | Aoai et al. . |
| 5,114,832 | 5/1992 | Zertani et al. . |
| 5,124,723 | 6/1992 | Laver . |
| 5,130,227 | 7/1992 | Wade et al. . |
| 5,130,778 | 7/1992 | Shor et al. . |
| 5,133,803 | 7/1992 | Moffatt . |
| 5,135,940 | 8/1992 | Belander et al. . |
| 5,139,572 | 8/1992 | Kawashima . |
| 5,141,556 | 8/1992 | Matrick . |
| 5,141,797 | 8/1992 | Wheeler . |
| 5,147,901 | 9/1992 | Rutsch et al. . |
| 5,153,104 | 10/1992 | Rossman et al. . |
| 5,153,105 | 10/1992 | Sher et al. . |
| 5,153,166 | 10/1992 | Jain et al. . |
| 5,160,372 | 11/1992 | Matrick . |
| 5,166,041 | 11/1992 | Murofushi et al. ............ 430/339 |
| 5,169,436 | 12/1992 | Matrick . |
| 5,169,438 | 12/1992 | Matrick . |
| 5,173,112 | 12/1992 | Matrick et al. . |
| 5,176,984 | 1/1993 | Hipps, Sr. et al. . |
| 5,178,420 | 1/1993 | Shelby . |
| 5,180,425 | 1/1993 | Matrick et al. . |

| | | |
|---|---|---|
| 5,180,652 | 1/1993 | Yamaguchi et al. . |
| 5,185,236 | 2/1993 | Shiba et al. . |
| 5,187,045 | 2/1993 | Bonham et al. . |
| 5,187,049 | 2/1993 | Sher et al. . |
| 5,190,565 | 3/1993 | Berenbaum et al. . |
| 5,190,845 | 3/1993 | Hashimoto et al. . |
| 5,196,295 | 3/1993 | Davis . |
| 5,198,330 | 3/1993 | Martic et al. . |
| 5,202,209 | 4/1993 | Winnik et al. . |
| 5,202,210 | 4/1993 | Matsuoka et al. . |
| 5,202,211 | 4/1993 | Vercoulen . |
| 5,202,212 | 4/1993 | Shin et al. . |
| 5,202,213 | 4/1993 | Nakahara et al. . |
| 5,202,215 | 4/1993 | Kanakura et al. . |
| 5,202,221 | 4/1993 | Imai et al. . |
| 5,205,861 | 4/1993 | Matrick . |
| 5,208,136 | 5/1993 | Zanoni et al. . |
| 5,209,814 | 5/1993 | Felten et al. . |
| 5,219,703 | 6/1993 | Bugner et al. . |
| 5,221,334 | 6/1993 | Ma et al. . |
| 5,224,197 | 6/1993 | Zanoni et al. . |
| 5,224,476 | 7/1993 | Schultz et al. . |
| 5,224,987 | 7/1993 | Matrick . |
| 5,241,059 | 8/1993 | Yoshinaga . |
| 5,250,109 | 10/1993 | Chan et al. . |
| 5,258,274 | 11/1993 | Helland et al. . |
| 5,262,276 | 11/1993 | Kawamura . |
| 5,268,027 | 12/1993 | Chan et al. . |
| 5,270,078 | 12/1993 | Walker et al. . |
| 5,271,765 | 12/1993 | Ma . |
| 5,272,201 | 12/1993 | Ma et al. . |
| 5,275,646 | 1/1994 | Marshall et al. ........................ 106/20 B |
| 5,279,652 | 1/1994 | Kaufmann et al. . |
| 5,284,734 | 2/1994 | Blum et al. . |
| 5,294,528 | 3/1994 | Furutachi . |
| 5,296,275 | 3/1994 | Goman et al. . |
| 5,296,556 | 3/1994 | Frihart . |
| 5,300,403 | 4/1994 | Angelopolus et al. . |
| 5,302,195 | 4/1994 | Helbrecht . |
| 5,302,197 | 4/1994 | Wickramanayke et al. . |
| 5,312,713 | 5/1994 | Yokoyama et al. . |
| 5,312,721 | 5/1994 | Gesign . |
| 5,324,349 | 6/1994 | Sano et al. . |
| 5,328,504 | 7/1994 | Ohnishi . |
| 5,330,860 | 7/1994 | Grot et al. . |
| 5,334,455 | 8/1994 | Noren et al. . |
| 5,340,631 | 8/1994 | Matsuzawa et al. . |
| 5,340,854 | 8/1994 | Martic et al. . |
| 5,356,464 | 10/1994 | Hickman et al. . |
| 5,362,592 | 11/1994 | Murofushi et al. . |
| 5,372,917 | 12/1994 | Tsuchida et al. . |
| 5,376,503 | 12/1994 | Audett et al. . |
| 5,393,580 | 2/1995 | Ma et al. . |
| 5,401,303 | 3/1995 | Stoffel et al. . |
| 5,415,976 | 5/1995 | Zaki . |
| 5,426,164 | 6/1995 | Babb et al. . |

FOREIGN PATENT DOCUMENTS

| | | |
|---|---|---|
| 637169 | 3/1964 | Belgium . |
| 275245 | 10/1928 | Canada . |
| 458808 | 12/1936 | Canada . |
| 413257 | 6/1943 | Canada . |
| 460268 | 10/1949 | Canada . |
| 461082 | 11/1949 | Canada . |
| 463021 | 2/1950 | Canada . |
| 463022 | 2/1950 | Canada . |
| 465495 | 5/1950 | Canada . |
| 465496 | 5/1950 | Canada . |
| 465499 | 5/1950 | Canada . |
| 483214 | 5/1952 | Canada . |
| 517364 | 10/1955 | Canada . |
| 537687 | 3/1957 | Canada . |
| 552565 | 2/1958 | Canada . |
| 571792 | 3/1959 | Canada . |
| 779239 | 2/1968 | Canada . |
| 930103 | 7/1973 | Canada . |
| 2053094 | 4/1992 | Canada . |
| 94118 | 5/1958 | Czechoslovakia . |
| 0127574 | 12/1984 | European Pat. Off. . |
| 0223587 | 5/1987 | European Pat. Off. . |
| 0280458 | 8/1988 | European Pat. Off. . |
| 0308274 | 3/1989 | European Pat. Off. . |
| 0371304 | 6/1990 | European Pat. Off. . |
| 0375160 | 6/1990 | European Pat. Off. . |
| 0390439 | 10/1990 | European Pat. Off. . |
| 0458140A1 | 10/1991 | European Pat. Off. . |
| 0468465 | 1/1992 | European Pat. Off. . |
| 0542286 | 5/1993 | European Pat. Off. . |
| 000571190 | 11/1993 | European Pat. Off. . |
| 1047787 | 12/1957 | Germany . |
| 1022801 | 1/1958 | Germany . |
| 1039835 | 9/1958 | Germany . |
| 1040562 | 10/1958 | Germany . |
| 1045414 | 12/1958 | Germany . |
| 1047013 | 12/1958 | Germany . |
| 1132450 | 7/1962 | Germany . |
| 1132540 | 7/1962 | Germany . |
| 1154069 | 9/1963 | Germany . |
| 1240811 | 5/1967 | Germany . |
| 2437380 | 2/1975 | Germany . |
| 244520 | 3/1975 | Germany . |
| 2416259 | 10/1975 | Germany . |
| 2714978 | 10/1977 | Germany . |
| 3921600 | 1/1990 | Germany . |
| 3833438 | 4/1990 | Germany . |
| 3833437 | 4/1990 | Germany . |
| 004036328 | 7/1991 | Germany . |
| 4132288 | 4/1992 | Germany . |
| 662500 | 4/1964 | Italy . |
| 43-15663 | 7/1968 | Japan . |
| 47-26653 | 7/1972 | Japan . |
| 47-45409 | 11/1972 | Japan . |
| 49-8909 | 2/1974 | Japan . |
| 50-65592 | 6/1975 | Japan . |
| 55-90506 | 7/1980 | Japan . |
| 55-090506 | 7/1980 | Japan ............................ 106/22 B |
| 0014233 | 2/1981 | Japan . |
| 56-14569 | 2/1981 | Japan . |
| 56-36556 | 4/1981 | Japan . |
| 57-61055 | 4/1982 | Japan . |
| 57-128283 | 8/1982 | Japan . |
| 57-171775 | 10/1982 | Japan . |
| 58-125770 | 7/1983 | Japan . |
| 58-211426 | 12/1983 | Japan . |
| 58-222164 | 12/1983 | Japan . |
| 59-89360 | 5/1984 | Japan . |
| 29219270 | 12/1984 | Japan . |
| 59-219270 | 4/1985 | Japan . |
| 60-192729 | 10/1985 | Japan . |
| 60-239741 | 11/1985 | Japan . |
| 60-239739 | 11/1985 | Japan . |
| 60-239740 | 11/1985 | Japan . |
| 60-239743 | 11/1985 | Japan . |
| 61-288 | 1/1986 | Japan . |
| 61-3781 | 1/1986 | Japan . |
| 61-14994 | 1/1986 | Japan . |
| 61-21184 | 1/1986 | Japan . |
| 61-25885 | 2/1986 | Japan . |
| 61-40366 | 2/1986 | Japan . |
| 61-30592 | 2/1986 | Japan . |
| 61-97025 | 9/1986 | Japan . |
| 61-222789 | 10/1986 | Japan . |
| 61-247703 | 11/1986 | Japan . |
| 61-285403 | 12/1986 | Japan . |

| | | |
|---|---|---|
| 62-7703 | 1/1987 | Japan . |
| 62-97881 | 5/1987 | Japan . |
| 62-100557 | 5/1987 | Japan . |
| 62-127281 | 6/1987 | Japan . |
| 63-43959 | 2/1988 | Japan . |
| 63-48370 | 3/1988 | Japan . |
| 63-95440 | 4/1988 | Japan . |
| 63-95445 | 4/1988 | Japan . |
| 63-95446 | 4/1988 | Japan . |
| 63-95447 | 4/1988 | Japan . |
| 63-95448 | 4/1988 | Japan . |
| 63-95439 | 4/1988 | Japan . |
| 63-95450 | 4/1988 | Japan . |
| 63-95449 | 4/1988 | Japan . |
| 63-151946 | 6/1988 | Japan . |
| 63-223078 | 9/1988 | Japan . |
| 63-223077 | 9/1988 | Japan . |
| 63-243101 | 10/1988 | Japan . |
| 63-199781 | 12/1988 | Japan . |
| 6429337 | 1/1989 | Japan . |
| 64-40948 | 2/1989 | Japan . |
| 89014948 | 3/1989 | Japan . |
| 1128063 | 5/1989 | Japan . |
| 1146974 | 6/1989 | Japan . |
| 01210477 | 8/1989 | Japan . |
| 1288854 | 11/1989 | Japan . |
| 292957 | 4/1990 | Japan . |
| 2179642 | 7/1990 | Japan . |
| 2282261 | 11/1990 | Japan . |
| 03163566 | 7/1991 | Japan . |
| 3-206439 | 9/1991 | Japan . |
| 5134447 | 11/1991 | Japan . |
| 3284668 | 12/1991 | Japan . |
| 3-203694 | 12/1991 | Japan . |
| 424756 | 1/1992 | Japan . |
| 4023884 | 1/1992 | Japan . |
| 4023885 | 1/1992 | Japan . |
| 4-45174 | 2/1992 | Japan . |
| 4100801 | 4/1992 | Japan . |
| 4-136075 | 5/1992 | Japan . |
| 04356087 | 12/1992 | Japan . |
| 543806 | 2/1993 | Japan . |
| 561220 | 3/1993 | Japan . |
| 5080506 | 4/1993 | Japan . |
| 05119506 | 5/1993 | Japan . |
| 5-140498 | 6/1993 | Japan . |
| 2-219869 | 9/1993 | Japan . |
| 5263067 | 10/1993 | Japan . |
| 680915 | 3/1994 | Japan . |
| 6116557 | 4/1994 | Japan . |
| 6116555 | 4/1994 | Japan . |
| 6116556 | 4/1994 | Japan . |
| 6116557 | 4/1994 | Japan . |
| 6214339 | 8/1994 | Japan . |
| 6256633 | 9/1994 | Japan . |
| 6256494 | 9/1994 | Japan . |
| 7113828 | 4/1972 | Netherlands . |
| 603767 | 8/1978 | Switzerland . |
| 197808 | 5/1988 | Switzerland . |
| 1310767 | 5/1987 | U.S.S.R. . |
| 1772118 | 10/1992 | U.S.S.R. . |
| 349339 | 5/1931 | United Kingdom . |
| 355686 | 8/1931 | United Kingdom . |
| 399753 | 10/1933 | United Kingdom . |
| 441085 | 1/1936 | United Kingdom . |
| 463515 | 4/1937 | United Kingdom . |
| 492711 | 9/1938 | United Kingdom . |
| 518612 | 3/1940 | United Kingdom . |
| 539912 | 9/1941 | United Kingdom . |
| 626727 | 7/1947 | United Kingdom . |
| 600451 | 4/1948 | United Kingdom . |
| 616362 | 1/1949 | United Kingdom . |
| 618616 | 2/1949 | United Kingdom . |
| 779389 | 7/1957 | United Kingdom . |
| 1372884 | 11/1974 | United Kingdom . |
| 2146357 | 4/1985 | United Kingdom . |
| 9211295 | 7/1992 | WIPO . |
| 93/06597 | 4/1993 | WIPO . |
| 94/22501 | 10/1994 | WIPO . |
| 94/22500 | 10/1994 | WIPO . |

OTHER PUBLICATIONS

Abstract of patent, JP 0643573 1994.

Pitchumani, K. et al. "Modification of chemical reactivity upon cyclodextrin encapsulation" *Chemical Abstracts* 121 982 [No. 121:13362 4v] 1994.

Derwent Publications Ltd., London, JP 05297627 (Fujitsu Ltd.), Nov. 12, 1993. (Abstract) 1993.

Patent Abstracts of Japan, JP 5241369 (Brando Chem Ind Ltd et al.), Sep. 21 1993. (Abstract) 1993.

Derwent Publications Ltd., London, JP 05232738 (Yamazaki, T.), Sep. 10, 1993. (Abstract) 1993.

Derwent Publications Ltd., London, EP 000559310 (Zeneca Ltd.), Sep. 8, 1993. (Abstract) 1993.

Derwent Publications Ltd., London, J,A, 5-230410 (Seiko Epson Corp), Sep. 7, 1993. (Abstract) 1993.

Derwent Publications Ltd., London, JP 5-230407 (Mitsubishi Kasei Corp), Sep. 7, 1993. (Abstract) 1993.

Patent Abstracts of Japan, JP 5197198 (Bando Chem Ind Ltd et al.), Aug. 6, 1993. (Abstract) 1993.

Database WPI—Week 9336, Derwent Publications Ltd., London, J,A, 5197069 (Bando Chem), Aug. 6, 1993. 1993.

Patent Abstracts of Japan, JP5181308 (Bando Chem Ind Ltd et al.), Jul. 23, 1993. (Abstract) 1993.

Patent Abstracts of Japan, JP 5181310 (Bando Chem Ind Ltd et al.), Jul. 23, 1993. (Abstract) 1993.

Derwent Publications Ltd., London, JP 5-132638 (Mitsubishi Kasei Corp), May 28, 1993. (Abstract) 1993.

Derwent Publications Ltd., London, JP 5-125318 (Mitsubishi Kasei Corp), May 21, 1993. (Abstract) 1993.

Abstract of patent, JP 05 117200 1993.

Derwent Publications Ltd., London, JP 05061246 (Ricoh KK), Mar. 12,1993. (Abstract) 1993.

Husain, N. et al. "Cyclodextrins as mobile–phase additives in reversed–phase HPLC" *American Laboratory* 82 80–87 1993.

Hamilton, D.P. "Tired of Shredding? New Ricoh Method Tries Different Tack" *Wall Street Journal* B2 1993.

Duxbury "The Photochemistry and Photophysics of Triphenylmethane Dyes in Solid Liquid Media" *Chemical Review* 93 381–433 1993.

Abstract of patent, JP 04351603 1992.

Abstract of patent, JP 04351602 1992.

Derwent Publications Ltd., London, JP 4–314769 (Citizen Watch Co Ltd), Nov. 5, 1992. (Abstract) 1992.

Abstract of patent, JP 04315739 1992.

Derwent Publications Ltd., London, JP 04300395 (Funai Denki KK), Oct. 23, 1992. (Abstract) 1992.

Derwent Publications Ltd., London, JP 4–213374 (Mitsubishi Kasei Corp), Aug. 4, 1992. (Abstract) 1992.

Abstract of patent, JP 04210228 1992.

Derwent Publications Ltd., London, J.P, 4–202271 (Mitsubishi Kasei Corp), Jul. 23, 1992. (Abstract) 1992.

Derwent Publications Ltd., London, J,A, 4–202571 (Canon Inc.), Jul. 23, 1992. (Abstract) 1992.

Derwent Publications Ltd., London, JP 4–189877 (Seiko Epson Corp), Jul. 8, 1992. (Abstract) 1992.

Derwent Publications Ltd., London, JP 4–189876 (Seiko Epson Corp), Jul. 8, 1992. (Abstract) 1992.
Derwent Publications Ltd., London, J,A, 4–170479 (Seiko Epson Corp), Jun. 18, 1992. (Abstract) 1992.
Abstract of patent, JP 0481402 1992.
Abstract of patent, JP 0481401 1992.
Derwent Publications Ltd., London, J0 3247676 (Canon KK), Nov. 5, 1991. (Abstract) 1991.
Abstract of patent, JP 03–220384 1991.
Derwent Publications Ltd., London, JP 3167270 (Mitsubishi Kasei Corp), Jul. 19, 1991. (Abstract) 1991.
Derwent Publications Ltd., London, J0 3093870 (Dainippon Ink Chem KK), Apr. 18, 1991. (Abstract) 1991.
Abstract of patent, JP 06369890 1991.
Abstract of patent, JP 03 41165 1991.
"Coloring/Decoloring Agent for Tonor Use Developed" *Japan Chemical Week* 1991.
Braithwaite, M., "Formulation" *Chemistry & Technology of UV & EB Formulation for Coatings, Inks & Paints* IV 11–12 1991.
*Scientific Polymer Products, Inc. Brochure* 24–31 1991.
Dietliker, K. "Photoiniators for Free Radical and Catioinc Polymerisation" *Chemistry & Technology of UV & EB Formulation for Coatings, Inks & Paints* III 1991.
Abstract of patent, JP 02289652 1990.
Abstract of Patent, JP 0297957, (Fuji Xerox Co., Ltd.) 1990.
Derwent Publications Ltd., London, JP 2091166 (Canon KK), Mar. 30, 1990. (Abstract) 1990.
Kogelschatz, U. "Silent Discharges for the Generation of ultraviolet and vacuum ultraviolet excimer radiation" *Pure & Applied Chem.* 62 1667–74 1990.
Abstract of patent, JP 01299083 1989.
Derwent Publications Ltd., London, J,0, 1182379 (Canon KK), Jul. 20, 1989. (Abstract) 1989.
Derwent Publications Ltd., London, J,0, 1011171 (Mitsubishi Chem Ind KK), Jan. 13, 1989. (Abstract) 1989.
"Xenographic Materials" *Encyclopedia of Polymer Science and Engineering* 17 918–943 1989.
Pappas, S.P. "Photocrosslinking" *Comph. Pol. Sci.* 6 135–148 1989.
Pappas, S.P. "Photoinitiated Polymerization" *Comph. Pol. Sci.* 4 337–355 1989.
Kirilenko, G.V. "An analog of the vesicular process with amplitude modulation of the incident light beam" *Chemical Abstracts* 111 569 [No. 111:12363 3b] 1989.
Abstract of patent, JP 63190815 1988.
Abstract of patent, JP 63144329 1988.
Abstract of patent, JP 63130164 1988.
Abstract of patent, JP 6177846 1988.
Abstract of patent, JP 6373241 1988.
Abstract of patent, JP 6347762, 1988.
Abstract of patent, JP 63 47763, 1988.
Abstract of patent, JP 63–47764, 1988.
Abstract of patent, JP 63–47765, 1988.
Eliasson, B., et al. "UV Excimer Radiation from Dielectric–Barrier Discharges" *Applied Physics B* 46 299–303 1988.
Abstract of patent, JP 62215261 1987.
Abstract of patent, JP 6232082 1987.
Derwent Publications Ltd., London, J6 2007772 (Alps Electric KK), Jan. 14, 1987. (Abstract) 1987.
Derwent Publications Ltd., London, JA 0284478 (Sanyo Chem Ind Ltd), Dec. 15, 1986. (Abstract) 1986.
Abstract of patent, JP 61251842 1986.
Abstract of patent, JP 6197025 1986.
Abstract of patent, JP 6187760 1986.
Derwent Publications Ltd., London, DL 0234731 (Karl Marx Univ. Leipzig), Apr. 9, 1986. (Abstract) 1986.
Derwent Publications Ltd., London, J, 0226575 (Sumitomo Chem Ind KK), Oct. 11, 1985. (Abstract) 1985.
Abstract of patent, JP 60156761 1985.
Derwent Publications Ltd., London, J,A, 0011451 (Fugi Photo Film KK), Jan. 21, 1985. (Abstract) 1985.
Roos, G. et al. "Textile applications of photocrosslinkable polymers" *Chemical Abstracts* 103 57 [No. 103:23690j] 1985.
Derwent Publications Ltd., London, JP 0198187 (Canon KK), Nov. 9, 1984. (Abstract) 1984.
Derwent Publications Ltd., London, J,A, 0169883 (Ricoh KK), Sep. 25, 1984. (Abstract) 1984.
Derwent Publications Ltd., London, J,A, 0053563 (Dainippon Toryo KK), Mar. 28, 1984. (Abstract) 1984.
Derwent Publications Ltd., London, J,A, 0053562 (Dainippon Toryo KK), Mar. 28, 1984. (Abstract) 1984.
Derwent Publications Ltd., London, J,A, 0051961 (Dainippon Toryo KK), Mar. 26, 1984. (Abstract) 1984.
Saenger, W. "Structural Aspects of Cyclodextrins and Their Inclusion Complexes" *Inclusion Compounds—Structural Aspects of Inclusion Compounds* 2 231–259 1984.
Szejtli "Industrial Applications of Cyclodextrins" *Inclusion Compounds: Physical Prop. & Applns* 3 331–390 1984.
"Clathrate Compounds, Molecular Inclusion Phenomena, and Cyclodextrins" *D. Reidel Publishing* 714–746 1984.
van Beek, H.C.A "Light–Induced Colour Changes in Dyes and Materials" *Color Res. and Appl.* 8 176–181 1983.
Connors, K.A. "Application of a stoichiometric model of cyclodextrin complex formation" *Chemical Abstracts* 98 598 [No. 98:53067g] 1983.
Derwent Publications Ltd., London, EP 0065617 (IBM Corp.), Dec. 1, 1982. (Abstract) 1982.
Derwent Publications Ltd., London, J,A, 0187289 (Honshu Paper Mfg KK), Nov. 17, 1982. (Abstract) 1982.
Derwent Publications Ltd., London, JA 0185364 (Ricoh KK), Nov. 15, 1982. (Abstract) 1982.
Derwent Publications Ltd., London, J,A, 0090069 (Canon KK), Jun. 4, 1982. (Abstract) 1982.
Derwent Publications Ltd., London, J,A, 0010661 (Canon KK), Jan. 20, 1982. (Abstract) 1982.
Derwent Publications Ltd., London, J,A, 0010659 (Canon KK), Jan. 20, 1982. (Abstract) 1982.
Derwent Publications Ltd., London, J,A, 0155263 (Canon KK), Dec. 1, 1981. (Abstract) 1981.
Derwent Publications Ltd., London, J,A, 0147861 (Canon KK), Nov. 17, 1981. (Abstract) 1981.
Derwent Publications Ltd., London, J,A, 0143273 (Canon KK), Nov. 7, 1981. (Abstract) 1981.
Derwent Publications Ltd., London, J,A, 0136861 (Canon KK), Oct. 26, 1981. (Abstract) 1981.
Derwent Publications Ltd., London, J,A, 6133378 (Canon KK), Oct. 19, 1981. (Abstract) 1981.
Derwent Publications Ltd., London, J,A, 6133377 (Canon KK), Oct. 19, 1981. (Abstract) 1981.
Derwent Publications Ltd., London, J,A, 6093775 (Canon KK), Jul. 29, 1981. (Abstract) 1981.
Derwent Publications Ltd., London, J,A, 0008135 (Ricoh KK), Jan. 27, 1981. (Abstract) 1981.
Derwent Publications Ltd., London, J,A, 0004488 (Canon KK), Jan. 17, 1981. (Abstract) 1981.

Rosanske et al. "Stoichiometric Model of Cyclodextrin Complex Formation" *Journal of Pharmaceutical Sciences* 69 (5) 564–567 1980.

Derwent Publications Ltd., London, J,A, 0005422 (Fuji Photo Film KK), Jan. 16, 1979. (Abstract) 1979.

"Color imaging devices and color filter arrays using photo–bleachable dyes" *Research Disclosure* 22–23 1979.

"Electrophotography" *Kirk–Othmer Encyclopedia of Chemical Technology* 8 794–826 1979.

Derwent Publications Ltd., London, J,A, 0012037 (Pentel KK), Jan. 29, 1977. (Abstract) 1977.

"Photo–bleachable dyes and processes" *Research Disclosure* 85–87 1975.

Jenkins, P.W. et al. "Photobleachable dye material" *Reseach Disclosure* 18 [No. 12932] 1975.

Lamberts, R.L. "Recording color grid patterns with lenticules" *Research Disclosure* 18–19 [No. 12923] 1975.

Karmanova, L.S. et al. "Light stabilizers of daytime fluorescent paints" *Chemical Abstracts* 82 147 [No. 59971p] 1975.

Prokopovich, B. et al. "Selection of effective photoinducers for rapid hardening of polyester varnish PE–250" *Chemical Abstracts* 83 131 [No. 81334a] 1975.

"Variable Contrast Printing System" *Research Disclosure* 19 [No. 12931] 1975.

Chang, I.F., et al. "Color Modulated Dye Ink Jet Printer" *IBM Technical Disclosure Bulletin* 17(5) 1520–1521 1974.

"Darocur 1173: Liquid Photoiniator for Ultraviolet Curing of Coatings" 1974.

Fischer, "Submicroscopic contact imaging with visible light by energy transfer".

Rigdon, J.E. "In Search of Paper that Spies Can't Copy" *Wall Street Journal*.

Chatterjee,S. et al. "Photochemistry of Carbocyanine Alkyltriphenylborate Salts: Intra–Ion–Pair Electron Transfer and" *J. Am. Chem. Soc.* 112 6329–6338.

"Assay—Physical and Chemical Analysis of Complexes" *AMAIZO*.

"Cyclodextrin" *AMAIZO*.

"Beta Cyclodextrin Polymer (BCDP)" *AMAIZO*.

"Chemically Modified Cyclodextrins" *AMAIZO*.

"Cyclodextrin Complexation" *American Maize Products Co.*

"Cyclodextrins: A Breakthrough for Molecular Encapsulation" *American Maize Products Co. (AMAIZO)* 1993.

"Monomers" *Scientific Polymer Products Inc.*

Suppan, Paul, "Quenching of Excited States" *Chemistry and Light* 65–69.

Yamaguchi, H. et al. "Supersensitization. Aromatic ketones as supersensitizers" *Chemical Abstracts* 53 107 (d).

Stecher, H. "Ultraviolet–absorptive additives in adhesives, lacquers and plastics" *Chemical Abstracts* 53 14579 (c).

Maslennikov, A.S. "Coupling of diazonium salts with ketones" *Chemical Abstracts* 60 3128e.

Derwent Publications, Ltd., London SU 292698–S Jan. 15, 1971 (abstract).

Derwent Publication, Ltd., London, JA 7226653.

Derwent Publications Ltd., London, 2416259.

Derwent Publications Ltd., London, 4 9128022.

Derwent Publications Ltd., London, 47 45409.

Derwent Publications Ltd., London, 7112489.

Derwent Publications Ltd., London, J6 2270665 (Konishiroku Photo KK), Nov. 25, 1987 (Abstract).

Derwent Publications, Ltd., London, EP 0280653, Aug. 31, 1988 (Abstract).

Derwent Publications, Ltd., London, SU 1423656 (Kherson Ind Inst), Sep. 15, 1988 (Abstract).

Abstract of Patent, JP 405195450.

Derwent Publications, Ltd., London, J6 1041381 (Osaka Prefecture), Feb. 27, 1986 (Abstract).

Derwent Publications, Ltd., London, JA 0061785 (Nippon Senka KK), Apr. 14, 1982 (Abstract).

Derwent Publications, Ltd., London, EP 0072775 (Ciba Geigy AG), Feb. 23, 1983 (Abstract).

Derwent Publications, Ltd., London, J6 3108074 (Konishiroku Photo KK), May 12, 1988 (Abstract).

Derwent Publications, Ltd., London,J6 3108073 (Konishiroku Photo KK), May 12, 1988(Abstract).

Derwent Publications, Ltd., London, J6 3112770 (Toray Ind Inc), May 17, 1988 (Abstract).

Derwent Publications, Ltd., London, JP 403269167 (Japan Wool Textile KK), Nov. 29, 1991 (Abstract).

Gafney et al. "Photochemical Reactions of Copper (II)—1, 3–Diketonate Complexes" *Journal of the Americqal Chemical Society*.

Gross et al. Laser direct–write metallization in thin palladium acetate films *J. App. Phys.* 61 (4) 1628–1632.

Al–Ismail et al. Some experimental results on thin polypropylene films loaded with finely–dispersed copper *Journal of Materials Science* 415–418.

Baufay et al. Optical self–regulation during laser–induced oxidation of copper *J. Appl. Phys* 61 (9) 4640–4651.

Esrom et al. Large area Photochemical Dry Etching of Polymers iwth Incoherent Excimer UV Radiation *MRS Materials Research Society* 1–7.

Derwent Publications, Ltd., London CA, 1086–719, (Sherwood Medical) Sep. 3, 1980 (Abstract).

New Excimer UV Sources for Industrial Applications *ABB Review* 391 1–10.

Kogelschatz Silent–discharge driven excimer UV sources and their applications *Applied Surface Science* 410–423.

Eliasson et al. New Trends in High Intensity UV Generation *EPA Newsletter* (32) 29–40.

Esrom et al. Excimer Laser–Induced Decomposition of Aluminum Nitride *Materials Research Society Fall Meeting* 1–6.

Esrom et al. Investigation of the mechanism of the UV–induced palladium depostions processf from thin solid *Applied Surface Science* 46 158–162.

Kogelschatz et al. New Incoherent Ultraviolet Excimer Sources for Photolytic Material Deposition.

Esrom et al. Metal deposition with a windowless VUV excimer source *Applied Surface Science* 1–5.

Esrom et al. UV excimer laser–induced pre–nucleation of surfaces followed by electroless metallization *Chemtronics* 4 216–223.

Esrom Excimer Laser–Induced Surface Activation of Aln for Electroless Metal Deposition *Mat. Res. Sco.lSymp. Proc.* 204 457–465.

Zhang et al. UV–induced decompositin of adsorbed Cu–acetylacetonate films at room temperature for electroless *Applied Surface Science* 1–6.

Esrom et al. VUV light–induced depostion of palladium using an incoherent Xe2* excimer source *Chemtronics* 4.

Lakshman Electronic Absorption Spectrum of Copper Formate Tetrahydrate *Chemical Physics Letters* 31 (2) 331–334.

Esrom et al. UV Light–Induced Depostion of Copper Films C5–719–C5–725.

Esrom et al. Metal Deposition with Incoherent Excimer Radiation *mat. Res. Soc. Symp. Proc.* 158 189–198.

Zhang et al. VUV synchrotron radiation processing of thin palladium acetate spin–on films for metallic surface *Applied Surface Science* 46 153–157.

Esrom UV Excimer Laer–Induced Deposition of Palladium from palladiym Acetate Films *Mat. Res. Soc. Symp. Proc.* 158 109–117.

German company develops reuseable paper *Pulp & Paper.* Derwent Publications, Ltd., London J6 0011–449–A (Taoka Chemical KK) Jan. 21, 1985 (abstract).

Derwent Publications, Ltd., London J5 7139–146 (Showa Kako KK) Aug. 27, 1982(abstract).

Derwent Publications, Ltd., London J4 9131–226 (TNational Cash Register C) Dec. 16, 1974 (abstract).

Derwent Publications, Ltd., London CA 1086–719 (Sherwood Medical) Sep. 30, 1980 (abstract).

INK FOR INK JET PRINTERS

CROSS-REFERENCE TO RELATED APPLICATIONS

This application is a continuation-in-part patent application of U.S. patent application Ser. No. 08/403,240, filed on Mar. 10, 1995, now abandoned, which is incorporated herein by reference, which is a continuation-in-part patent application of U.S. patent application Ser. No. 08/373,958, filed on Jan. 17, 1995, which is incorporated herein by reference, which is a continuation-in-part of U.S. patent application Ser. No. 08/360,501, filed on Dec. 21, 1994, which is incorporated herein by reference, and U.S. patent application Ser. No. 08/359,670, filed on Dec. 20, 1994, now abandoned which is incorporated herein by reference, both of which are continuation-in-part patent applications of U.S. patent application Ser. No. 08/336,813, filed Nov. 9, 1994, now abandoned and U.S. patent application Ser. No. 08/258,858, filed on Jun. 13, 1994, now abandoned which is incorporated herein by reference, which is a continuation-in-part patent application of U.S. patent application Ser. No. 08/119,912, filed Sep. 10, 1993, now abandoned, which is incorporated herein by reference, and is a continuation-in-part patent application of U.S. patent application Ser. No. 08/103,503, filed on Aug. 5, 1993, now abandoned which is incorporated herein by reference.

TECHNICAL FIELD

The present invention is directed to ink compositions. More specifically, the present invention is directed to ink compositions that are particularly suitable for use in ink jet printing processes. The present invention more particularly relates to improved ink compositions comprising a light-stable and/or mutable colored composition.

BACKGROUND OF THE INVENTION

Ink jet printing technology is used from industrial labeling applications to office printing. Ink jet printers are low cost, low maintenance, quiet printers that provide near laser printing quality with high print speeds. Another advantage of the use of ink jet printers is the development of consistent, high-quality color printing capabilities for the full range of colors. These attributes have made the ink jet printer one of the most popular office printers on the market today. Ink jet printing technology has also expanded into the reprographic market with the advent of large format ink jet plotters, such as the Hewlett Packard Designjet series and Encad's Novajet series. Such plotters can produce a range of sizes of drawings and designs from the standard A size (8.5"×11") up to an E size (36"×48") plot. For example, ink jet plotters are used in the production of designs, floor plans, and structures with computer aided design (CAD) software.

Ink jet printing technology is a form of printing that encompasses the projection of ink through a nozzle orifice, forming tiny droplets of a specific diameter, directly onto a substrate, such as paper or film, to form written symbols and drawn images. Several different technologies are used for such projection of ink droplets onto a substrate. For example, in a continuous stream system a continuous stream of ink droplets is discharged from an ink reservoir through a nozzle. The droplets may then be deflected by means of an electrically charged field to the substrate to form an image on an ink-receiving substrate. Those droplets not deflected to the substrate by the electrically charged field are allowed to flow in a straight stream and are collected and recirculated for reuse.

Another example of ink jet printing technology is drop-on-demand systems, a droplet is expelled from an orifice directly to a position on a recording medium in accordance with digital data signals. A droplet is not formed or expelled unless it is to be placed on the recording medium. Since drop-on-demand systems require no ink recovery, charging, or deflection, the system is much simpler than the continuous stream type. There are two types of drop-on-demand ink jet systems.

One type of drop-on-demand system has as its major components an ink filled channel or passageway having a nozzle on one end and a piezoelectric transducer near the other end to produce pressure pulses. The relatively large size of the transducer prevents the close spacing of the nozzles to one another which is necessary for high resolution printing. Additionally, physical limitations of the transducer result in low ink drop velocity. Low drop velocity seriously diminishes tolerances for drop velocity variation and directionality, thus impacting the system's ability to produce high quality copies, and also decreases printing speed. Drop-on-demand systems which use piezoelectric devices to expel the droplets also suffer the disadvantage of a slow printing speed.

The other type of drop-on-demand system is known as thermal ink jet, or bubble jet, and produces high velocity droplets and allows very close spacing of nozzles. The major components of this type of drop-on-demand system are an ink filled channel having a nozzle on one end and a heat generating resistor near the nozzle. Printing signals representing digital information originate an electric current pulse in a resistive layer within each ink passageway near the orifice or nozzle, causing the liquid vehicle of the ink in the immediate vicinity to undergo a liquid-gas phase transition, which creates a bubble. The ink at the orifice is forced out as a propelled droplet as the bubble expands. The drop-on-demand ink jet printers provide simpler, lower cost devices than their continuous stream counterparts, and yet have substantially the same high speed printing capability.

A major problem with inks used in ink jet printers is that the dye colorants contained in the ink tend to fade when exposed to sunlight or artificial light. It is believed that most of the fading of colorants when exposed to light is due to photodegradation mechanisms. These degradation mechanisms include oxidation or reduction of the colorants depending upon the environmental conditions in which the colorant is placed. Fading of a colorant also depends upon the substrate upon which they reside.

Various factors such as temperature, humidity, gaseous reactants, including $O_2$, $O_3$, $SO_2$, and $NO_2$, and water soluble, nonvolatile photodegradation products have been shown to influence fading of colorants. The factors that effect colorant fading appear to exhibit a certain amount of interdependence. It is due to this complex behavior that observations for the fading of a particular colorant on a particular substrate cannot be applied to colorants and substrates in general.

Under conditions of constant temperature it has been observed that an increase in the relative humidity of the atmosphere increases the fading of a colorant for a variety of colorant-substrate systems (e.g., McLaren, K., *J. Soc. Dyers Colour*, 1956, 72, 527). For example, as the relative humidity of the atmosphere increases, a fiber may swell because the moisture content of the fiber increases. This aids diffusion of gaseous reactants through the substrate structure.

The ability of a light source to cause photochemical change in a colorant is also dependent upon the spectral distribution of the light source, in particular the proportion of radiation of wavelengths most effective in causing a change in the colorant and the quantum yield of colorant degradation as a function of wavelength. On the basis of photochemical principles, it would be expected that light of higher energy (short wavelengths) would be more effective at causing fading than light of lower energy (long wavelengths). Studies have revealed that this is not always the case. Over 100 colorants of different classes were studied, and it was found that generally the most unstable were faded more efficiently by visible light while those of higher lightfastness were degraded mainly by ultraviolet light (McLaren, K., *J. Soc. Dyers Colour*, 1956, 72, 86).

The influence of a substrate on colorant stability can be extremely important. Colorant fading may be retarded or promoted by some chemical group within the substrate. Such a group can be a ground-state species or an excited-state species. The porosity of the substrate is also an important factor in colorant stability. A high porosity can promote fading of a colorant by facilitating penetration of moisture and gaseous reactants into the substrate. A substrate may also act as a protective agent by screening the colorant from light of wavelengths capable of causing degradation.

The purity of the substrate is also an important consideration whenever the photochemistry of dyed technical polymers is considered. For example, technical-grade cotton, viscose rayon, polyethylene, polypropylene, and polyisoprene are known to contain carbonyl group impurities. These impurities absorb light of wavelengths greater than 300 nm, which are present in sunlight, and so, excitation of these impurities may lead to reactive species capable of causing colorant fading (van Beek, H. C. A., *Col. Res. Appl.*, 1983, 8(3), 176).

Therefore, for all of these reasons, there exists a great need for methods and compositions which are capable of stabilizing a wide variety of colorants from the effects of both sunlight and artificial light. There is a particular need for an improved ink for ink jet printers that are light-stable.

SUMMARY OF THE INVENTION

The present invention addresses the needs described above by providing an improved, light-stable and/or mutable ink composition. The present invention includes an improved ink composition comprising a colored composition and a liquid vehicle. A feature of the present invention is that the colored composition comprises a colorant and a arylketoalkene stabilizing compound or a photoreactor or modified photoreactor. An advantage of the present invention is that the arylketoalkene stabilizing compound or photoreactor provides superior and unexpected light stability characteristics to the colored composition. As a consequence, the improved ink is particularly suited for printing applications entailing substantial exposure to light, and for long-term archival print applications.

Another feature of the invention is that the colored composition may optionally contain a wavelength-selective sensitizer combined with the photoreactor to form a radiation transorber. An advantage of including a radiation transorber in the ink jet ink composition of the present invention is that the colorant is mutable upon exposure to specific narrow wavelength radiation. Thus, printed images may be selectively altered in response to exposure to specific wavelength radiation. The colored composition may also contain a molecular includant, which provides further desirable characteristics to the improved ink of the present invention.

The present invention also includes ink jet printer cartridges containing the improved ink of the present invention and methods of printing using the improved ink of the present invention.

These and other objects, features and advantages of the present invention will become apparent after a review of the following detailed description of the disclosed embodiments and the appended claims.

DETAILED DESCRIPTION OF THE INVENTION

Figure 1:
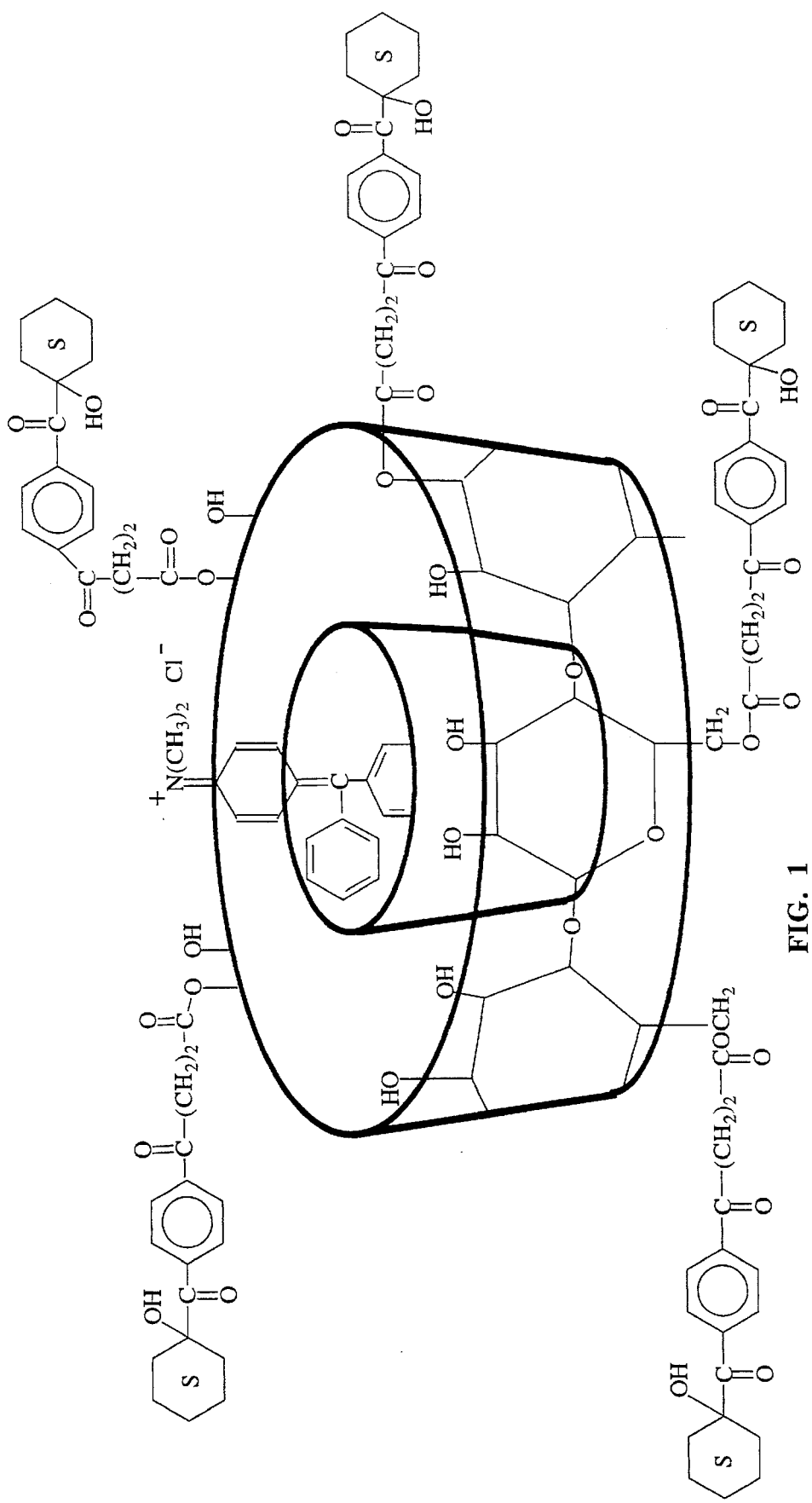
FIG. 1 illustrates an ultraviolet radiation transorber/mutable colorant/molecular includant complex wherein the mutable colorant is malachite green, the ultraviolet radiation transorber is IRGACURE 184 (1-hydroxycyclohexyl phenyl ketone), and the molecular includant is β-cyclodextrin.

The present invention relates generally to an improved ink comprising a light-stable colored composition that is optionally mutable at a specific wavelength of electromagnetic radiation and a liquid vehicle that is compatible with the colored composition.

More particularly, one embodiment the present invention includes an improved ink composition suitable for ink jet printing comprising, a mixture of a colored composition and a liquid vehicle, wherein the colored composition comprises a colorant and a photoreactor or a modified photoreactor, wherein the colorant is light-stable, and wherein the ink is suitable for ink jet printing.

The colored composition may also include a wavelength-selective sensitizer combined with the photoreactor to form a radiation transorber, wherein the colorant is mutable by exposure to narrow bandwidth radiation. The colored composition that is mutable is also described in U.S. patent application Ser. No. 08/461,372, filed Jun. 5, 1995, which is hereby incorporated by reference. Optionally, a molecular includant can be included in the colored composition to provide a more stable colorant to sunlight and ordinary artificial light and, when a wavelength-selective sensitizer is included to provide a radiation transorber, a more efficient mutable colorant.

The present invention also includes an improved ink composition suitable for ink jet printing comprising an admixture of a colored composition and a liquid vehicle, wherein the colored composition comprises a colorant and an arylketoalkene stabilizer represented in the following general formula:

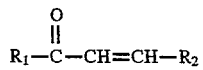

wherein when $R_1$ is an aryl group, $R_2$ is a hydrogen; alkyl; aryl; heterocyclic; or phenyl group, the phenyl group optionally being substituted with an alkyl, halo, amino, or thiol group; and wherein when $R_2$ is an aryl group, $R_1$ is a hydrogen; alkyl; aryl; heterocyclic; or phenyl group, the phenyl group optionally being substituted with an alkyl, halo, amino, or thiol group. Preferably, the alkene group is in the trans configuration. The following compounds represented by the following formulas are preferred:

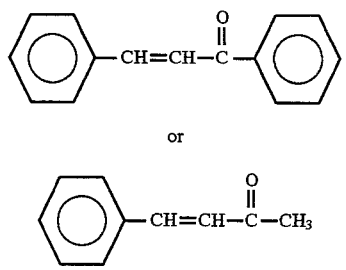

Accordingly, this embodiment of the present invention provides a stabilizing molecule, the above arylketoalkene, which when associated with a colorant, stabilizes the colorant. Therefore, the above arylketoalkene can be used as an additive to any colorant composition. For example, as the arylketoalkene compound is poorly soluble in water, it can be directly added to non-aqueous solvent or oil based colorant compositions. Additionally, the arylketoalkene compound can be added to other colorant compositions that contain additives enabling the solubilization of the compound therein. Further, the arylketoalkene stabilizing compounds can be solubilized in an aqueous solution by attaching the compound to a large water soluble molecule, such as a cyclodextrin. Optionally, a photoreactor can be included in the colored composition to provide a radiation transorber, and therefore, a mutable colorant, as discussed more fully below. However, it is to be understood that the arylketoalkene stabilizing compound is not to be used with photoreactors in a colored composition when stability of the colorant to natural sunlight is desired. The arylketoalkene compounds absorb radiation in the wavelength range of about 270 nm to about 310 nm, depending on the identity of $R_1$ and $R_2$. Accordingly, the arylketoalkene compounds are capable of absorbing radiation from sunlight and, when combined with a photoreactor can effect a mutation of the colorant upon exposure to sunlight. Where such a change in color is not desired, then a photoreactor is not to be admixed with the arylketoalkene compound in a colored composition.

The present invention also includes ink jet printer cartridges containing the improved ink of the present invention and methods of printing using the improved ink of the present invention.

After definition of various terms used herein, the colored composition of the present invention and the method of making that composition are described, followed by a description of the improved ink jet ink composition of the present invention, and methods of using the improved ink.

The term "colored composition" is used herein to mean a composition comprising a colorant and a photoreactor or an arylketoalkene stabilizer. In one embodiment the photoreactor is a modified photoreactor. The colored composition may further comprise a wavelength-selective sensitizer combined with a photoreactor or modified photoreactor (to form a radiation transorber). Alternatively, the colored composition may comprise a photoreactor combined with an arylketoalkene stabilizer. The colored composition may also include a molecular includant.

The term "photoreactor" means a conventional photoreactor as described more fully herein, and also includes modified photoreactors, wherein, for example, the photoreactor has been modified to remove the functional group α to the carbonyl carbon.

As used herein, the term "colorant" is meant to include, without limitation, any material which absorbs light in the visible wavelength so that the material is colored. This includes, but is not limited to, material which, in the presence of a radiation transorber, is adapted upon exposure to specific radiation to be mutable. The colorant typically will be an organic material, such as an organic colorant, dye or pigment. Desirably, the colorant will be substantially transparent to, that is, will not significantly interact with, the ultraviolet radiation to which it is exposed. The term is meant to include a single material or a mixture of two or more materials.

As used herein, the term "irreversible" means that the colorant will not revert to its original color when it no longer is exposed to ultraviolet radiation.

The term "radiation transorber" as used herein means a photoreactor combined with a wavelength-selective sensitizer. A radiation transorber is any material which is adapted to absorb radiation at a specific wavelength and interact with the colorant to affect the mutation of the colorant and, at the same time, protect the colorant from fading in sunlight or artificial light. The term "ultraviolet radiation transorber" is used herein to mean any material which is adapted to absorb ultraviolet radiation and interact with the colorant to effect the mutation of the colorant. In some embodiments, the ultraviolet radiation transorber may be an organic compound. The term "compound" is intended to include a single material or a mixture of two or more materials. If two or more materials are employed, it is not necessary that all of them absorb radiation of the same wavelength. The term "light-stable" is used herein to mean that the colorant, when associated with the photoreactor or radiation transorber or arylketoalkene stabilizer, is more stable to light, including, but not limited to, sunlight or artificial light, than when the colorant is not associated with one of these molecules.

The term "artificial light" is used herein to mean light having a relatively broad bandwidth that is produced from conventional light sources, including, but not limited to, conventional incandescent light bulbs and fluorescent light bulbs.

The term "ultraviolet radiation" is used herein to mean electromagnetic radiation having wavelengths in the range of from about 4 to about 400 nanometers. The especially desirable ultraviolet radiation range for the present invention is between approximately 100 to 375 nanometers. Thus, the term includes the regions commonly referred to as ultraviolet and vacuum ultraviolet. The wavelength ranges typically assigned to these two regions are from about 180 to about 400 nanometers and from about 100 to about 180 nanometers, respectively.

The term "associated", in its broadest sense, means that the colorant and the photoreactor or radiation transorber are at least in close proximity to the molecular includant.

The term "mutable" with reference to the colorant is used to mean that the absorption maximum of the colorant in the visible region of the electromagnetic spectrum is capable of being mutated or changed by exposure to radiation, desirably ultraviolet radiation, when in the presence of the radiation transorber. In general, it is only necessary that such absorption maximum be mutated to an absorption maximum which is different from that of the colorant prior to exposure to the ultraviolet radiation, and that the mutation be irreversible. Thus, the new absorption maximum can be within or outside of the visible region of the electromagnetic spectrum. In other words, the colorant can mutate to a different color or be rendered colorless. The latter is also desirable when the colorant is used in data processing forms for use with photo-sensing apparatus that detect the presence of indicia at indicia-receiving locations of the form.

The term "incoherent, pulsed ultraviolet radiation" has reference to the radiation produced by a dielectric barrier discharge excimer lamp (referred to hereinafter as "excimer lamp"). Such a lamp is described, for example, by U. Kogelschatz, "Silent discharges for the generation of ultraviolet and vacuum ultraviolet excimer radiation," Pure & Appl. Chem., 62, No. 9, pp. 1667–1674 (1990); and E. Eliasson and U. Kogelschatz, "UV Excimer Radiation from Dielectric-Barrier Discharges," Appl. Phys. B, 46, pp. 299–303 (1988).

The term "molecular includant," as used herein, means any substance having a chemical structure which defines at least one cavity. That is, the molecular includant is a cavity-containing structure. As used herein, the term "cavity" is meant to include any opening or space of a size sufficient to accept at least a portion of the colorant, of the arylketoalkene stabilizing compound or of the photoreactor, or, when a wavelength-selective sensitizer is combined with the photoreactor, of the radiation transorber. Thus, the cavity can be a tunnel through the molecular includant or a cave-like space or indention in the molecular includant. The cavity can be isolated or independent, or connected to one or more other cavities.

The term "functionalized molecular includant" is used herein to mean a molecular includant to which one or more molecules of an ultraviolet radiation transorber or modified photoreactor or arylketoalkene stabilizer are covalently coupled to each molecule of the molecular includant. The term "degree of substitution" is used herein to refer to the number of these molecules or leaving groups (defined below) which are covalently coupled to each molecule of the molecular includant.

The term "derivatized molecular includant" is used herein to mean a molecular includant having more than two leaving groups covalently coupled to each molecule of molecular includant. The term "leaving group" is used herein to mean any leaving group capable of participating in a bimolecular nucleophilic substitution reaction.

In several embodiments, the radiation transorber molecule, the wavelength-selective sensitizer, the photoreactor, or the arylketoalkene stabilizer, or a combination thereof, may be associated with a molecular includant. It is to be noted that in all the formulas, the number of such molecules can be between approximately 1 and approximately 21 molecules per molecular includant. Of course, in certain situations, there can be more than 21 molecules per molecular includant molecule. Desirably, there are more than three of such molecules per molecular includant.

The degree of substitution of the functionalized molecular includant may be in a range of from 1 to approximately 21. As another example, the degree of substitution may be in a range of from 3 to about 10. As a further example, the degree of substitution may be in a range of from about 4 to about 9.

The colorant is associated with the functionalized molecular includant. The term "associated" in its broadest sense means that the colorant is at least in close proximity to the functionalized molecular includant. For example, the colorant may be maintained in close proximity to the functionalized molecular includant by hydrogen bonding, van der Waals forces, or the like. Alternatively, the colorant may be covalently bonded to the functionalized molecular includant, although this normally is neither desired nor necessary. As a further example, the colorant may be at least partially included within the cavity of the functionalized molecular includant.

The examples below disclose methods of preparing and associating these colorants and ultraviolet radiation transorbers to β-cyclodextrins. For illustrative purposes only, Examples 1, 2, 6, and 7 disclose one or more methods of preparing and associating colorants and ultraviolet radiation transorbers to cyclodextrins.

In those embodiments of the present invention in which the ultraviolet radiation transorber is covalently coupled to the molecular includant, the efficiency of energy transfer from the ultraviolet radiation transorber to the colorant is, at least in part, a function of the number of ultraviolet radiation transorber molecules which are attached to the molecular includant. It now is known that the synthetic methods described above result in covalently coupling an average of two transorber molecules to each molecule of the molecular includant. As discussed more fully below, a colorant combined with a radiation transorber is mutable upon exposure to narrow wavelength radiation. Because the time required to mutate the colorant should, at least in part, be a function of the number of ultraviolet radiation transorber molecules coupled to each molecule of molecular includant, there is a need for an improved colored composition in which an average of re.ore than two ultraviolet radiation transorber molecules are covalently coupled to each molecule of the molecular includant.

Accordingly, the present invention also relates to a composition which includes a colorant and a functionalized molecular includant. For illustrative purposes only, Examples 12 through 19, and 21 through 22 disclose other methods of preparing and associating colorants and ultraviolet radiation transorbers to cyclodextrins, wherein more than two molecules of the ultraviolet radiation transorber are covalently coupled to each molecule of the molecular includant. Further, Examples 29 and 31 disclose methods of preparing and associating arylketoalkene stabilizers with. cyclodextrin, wherein the cyclodextrin has an average of approximately 3 or 4 stabilizer molecules attached thereto.

The present invention also provides a method of making a functionalized molecular includant. The method of making a functionalized molecular includant involves the steps of providing a derivatized ultraviolet radiation transorber having a nucleophilic group, providing a derivatized molecular includant having more than two leaving groups per molecule, and reacting the derivatized ultraviolet radiation transorber with the derivatized molecular includant under conditions sufficient to result in the covalent coupling of an average of more than two ultraviolet radiation transorber molecules to each molecular includant molecule. By way of example, the derivatized ultraviolet radiation transorber may be 2-[p-(2-methyl-2-mercaptomethylpropionyl)phenoxy] ethyl 1,3-dioxo-2-isoindolineacetate. As another example, the derivatized ultraviolet radiation transorber may be 2-mercaptomethyl-2-methyl-4'-[2-[p-(3-oxobutyl)phenoxy] ethoxy]propiophenone.

In general, the derivatized ultraviolet radiation transorber and the derivatized molecular includant are selected to cause the covalent coupling of the ultraviolet radiation transorber to the molecular includant by means of a bimolecular nucleophilic substitution reaction. Consequently, the choice of the nucleophilic group and the leaving groups and the preparation of the derivatized ultraviolet radiation transorber and derivatized molecular includant, respectively, may be readily accomplished by those having ordinary skill in the art without the need for undue experimentation.

The nucleophilic group of the derivatized ultraviolet radiation transorber may be any nucleophilic group capable of participating in a bimolecular nucleophilic substitution reaction, provided, of course, that the reaction results in the covalent coupling of more than two molecules of the ultraviolet radiation transorber to the molecular includant. The nucleophilic group generally will be a Lewis base, i.e., any group having an unshared pair of electrons. The group may be neutral or negatively charged. Examples of nucleophilic groups include, by way of illustration only, aliphatic hydroxy, aromatic hydroxy, alkoxides, carboxy, carboxylate, amino, and mercapto.

Similarly, the leaving group of the derivatized molecular includant may be any leaving group capable of participating in a bimolecular nucleophilic substitution reaction, again provided that the reaction results in the covalent coupling of more than two molecules of the ultraviolet radiation transorber to the molecular includant. Examples of leaving groups include, also by way of illustration only, p-toluenesulfonates (tosylates), p-bromobenzenesulfonates (brosylates), p-nitrobenzenesulfonates (nosylates), methanesulfonates (mesylates), oxonium ions, alkyl perchlorates, ammonioalkane sulfonate esters (betylates), alkyl fluorosulfonates, trifluoromethanesulfonates (triflates), nonafluorobutanesulfonates (nonaflates), and 2,2,2-trifluoroethanesulfonates (tresylates).

The reaction of the derivatized ultraviolet radiation transorber with the derivatized molecular includant is carried out in solution. The choice of solvent depends upon the solubilities of the two derivatized species. As a practical matter, a particularly useful solvent is N,N-dimethylformamide (DMF).

The reaction conditions, such as temperature, reaction time, and the like generally are matters of choice based upon the natures of the nucleophilic and leaving groups. Elevated temperatures usually are not required. For example, the reaction temperature may be in a range of from about 0° C. to around ambient temperature, i.e., to 20°–25° C.

The preparation of the functionalized molecular includant as described above generally is carried out in the absence of the colorant. However, the colorant may be associated with the derivatized molecular includant before reacting the derivatized ultraviolet radiation transorber with the derivatized molecular includant, particularly if a degree of substitution greater than about three is desired. When the degree of substitution is about three, it is believed that the association of the colorant with the functionalized molecular includant still may permit the colorant to be at least partially included in a cavity of the functionalized molecular includant. At higher degrees of substitution, such as about six, steric hindrance may partially or completely prevent the colorant from being at least partially included in a cavity of the functionalized molecular includant. Consequently, the colorant may be associated with the derivatized molecular includant which normally will exhibit little, if any, steric hindrance. In this instance, the colorant will be at least partially included in a cavity of the derivatized molecular includant. The above-described bimolecular nucleophilic substitution reaction then may be carried out to give a colored composition of the present invention in which the colorant is at least partially included in a cavity of the functionalized molecular includant.

As stated above, the colored composition of the present invention comprises one or more colorants, and a photoreactor or an arylketoalkene stabilizer. The colored composition may also contain a wavelength selective-sensitizer combined with the photoreactor to form a radiation transorber. Optionally, the colored composition may also contain a molecular includant.

The dye, for example, may be an organic dye. Organic dye classes include, by way of illustration only, triarylmethyl dyes, such as Malachite Green Carbinol base {4-(dimethylamino)-α-[4-(dimethylamino)phenyl]-α-phenylbenzene-methanol}, Malachite Green Carbinol hydrochloride {N-4-[[4-(dimethylamino)phenyl] phenylmethylene]-2,5-cyclohexyldien-1-ylidene]-N-methyl-methanaminium chloride or bis[p-(dimethylamino) phenyl]phenylmethylium chloride}, and Malachite Green oxalate {N-4-[[-4-(dimethylamino)phenyl] phenylmethylene]-2,5-cyclohexyldien-1-ylidene]-N-methylmethanaminium chloride or bis[p-(dimethylamino) phenyl]phenylmethylium oxalate}; monoazo dyes, such as Cyanine Black, Chrysoidine [Basic Orange 2; 4-(phenylazo) -1,3-benzenediamine monohydrochloride], Victoria Pure Blue BO, Victoria Pure Blue B, basic fuschin and β-Naphthol Orange; thiazine dyes, such as Methylene Green, zinc chloride double salt [3,7-bis(dimethylamino)-6-nitrophenothiazin-5-ium chloride, zinc chloride double salt]; oxazine dyes, such as Lumichrome (7,8-dimethylalloxazine); naphthalimide dyes, such as Lucifer Yellow CH {6-amino-2-[(hydrazinocarbonyl)amino]-2,3-dihydro-1,3-dioxo-1H-benz[de]isoquinoline-5,8-disulfonic acid dilithium salt}; azine dyes, such as Janus Green B {3-(diethylamino)-7-[[4-(dimethylamino)phenyl]azo]-5-phenylphenazinium chloride}; cyanine dyes, such as Indocyanine Green {Cardio-Green or Fox Green; 2-[7-[1,3-dihydro-1,1-dimethyl-3-(4-sulfobutyl)-2H-benz[e]indol-2-ylidene]-1,3,5-heptatrienyl]-1,1-dimethyl-3-(4-sulfobutyl)-1H-benz[e]indolium hydroxide inner salt sodium salt}; indigo dyes, such as Indigo {Indigo Blue or Vat Blue 1; 2-(1,3-dihydro-3-oxo-2H-indol-2-ylidene)-1,2-dihydro-3H-indol-3-one}; coumarin dyes, such as 7-hydroxy-4-methylcoumarin (4-methylumbelliferone); benzimidazole dyes, such as Hoechst 33258 [bisbenzimide or 2-(4-hydroxyphenyl)-5-(4-methyl-1-piperazinyl)-2,5-bi-1H-benzimidazole trihydrochloride pentahydrate]; paraquinoidal dyes, such as Hematoxylin {Natural Black 1; 7,1 11b-dihydrobenz[b]indeno[1,2-d]pyran-3,4,6a,9,10(6H)-pentol}; fluorescein dyes, such as Fluoresceinamine (5-aminofluorescein); diazonium salt dyes, such as Diazo Red RC (Azoic Diazo No. 10 or Fast Red RC salt; 2-methoxy-5-chlorobenzenediazonium chloride, zinc chloride double salt); azoic diazo dyes, such as Fast Blue BB salt (Azoic Diazo No. 20; 4-benzoylamino-2,5-diethoxybenzene diazonium chloride, zinc chloride double salt); phenylenediamine dyes, such as Disperse Yellow 9 [N-(2,4-dinitrophenyl)-1,4-phenylenediamine or Solvent Orange 53]; diazo dyes, such as Disperse Orange 13 [Solvent Orange 52; 1-phenylazo-4-(4-hydroxyphenylazo) naphthalene]; anthraquinone dyes, such as Disperse Blue 3 [Celliton Fast Blue FFR; 1-methylamino-4-(2-hydroxyethylamino)-9,10-anthraquinone], Disperse Blue 14 [Celliton Fast Blue B; 1,4-bis(methylamino)- 9,10-anthraquinone], and Alizarin Blue Black B (Mordant Black 13); trisazo dyes, such as Direct Blue 71 {Benzo Light Blue FFL or Sirius Light Blue BRR; 3-[(4-[(4-[(6-amino-1-hydroxy-3-sulfo-2-naphthalenyl)azo]-6-sulfo-1-naphthalenyl)azo]-1-naphthalenyl)azo]-1,5-naphthalenedisulfonic acid tetrasodium salt}; xanthene dyes, such as 2,7-dichlorofluorescein; proflavine dyes, such as 3,6-diaminoacridine hemisulfate (Proflavine); sulfonaphthalein dyes, such as Cresol Red (o-cresolsulfonaphthalein); phthalocyanine dyes, such as Copper Phthalocyanine {Pigment Blue 15; (SP-4-1)-[29H,31H-phthalocyanato(2-)-$N^{29}$, $N^{30}$, $N^{31}$, $N^{32}$]copper}; carotenoid dyes, such as trans-β-carotene (Food Orange 5); canninic acid dyes, such as Carmine, the aluminum or calcium-aluminum lake of carminic acid (7-a-D-glucopyranosyl-9,10-dihydro-3,5,6,8-tetrahydroxy-1-methyl-9,10-dioxo-2-anthracenecarbonylic acid); azure dyes, such as Azure A [3-amino-7-(dimethylamino)phenothiazin-5-ium chloride or 7-(dimethylamino)-3-imino-3H-phenothiazine hydrochloride]; and acridine dyes, such as Acridine Orange [Basic Orange 14; 3,8-bis(dimethylamino)acridine hydrochloride, zinc chloride double salt] and Acriflavine (Acriflavine neutral; 3,6-diamino-10-methylacridinium chloride mixture with 3,6-acridinediamine).

The present invention includes unique compounds, namely, radiation transorbers, that are capable of absorbing narrow ultraviolet wavelength radiation, while at the same time, imparting light-stability to a colorant with which the compounds are associated. The compounds are synthesized by combining a wavelength-selective sensitizer and a photoreactor. The photoreactors oftentimes do not efficiently absorb high energy radiation. When combined with the wavelength-selective sensitizer, the resulting compound is a wavelength specific compound that efficiently absorbs a very narrow spectrum of radiation. The wavelength-selective sensitizer may be covalently coupled to the photoreactor.

By way of example, the wavelength-selective sensitizer may be selected from the group consisting of phthaloylglycine and 4-(4-oxyphenyl)-2-butanone. As another example, the photoreactor may be selected from the group consisting of 1-[4-(2-hydroxyethoxy)phenyl]-2-hydroxy-2-methylpropan-1-one and cyclohexyl-phenyl ketone ester. Other photoreactors are listed by way of example, in the detailed description below regarding the impoved stabilized composition of the present invention. As a further example, the ultraviolet radiation transorber may be 2-[p-2-methyllactoyl)phenoxy]ethyl 1,3-dioxo-2-isoindolineacetate. As still another example, the ultraviolet radiation transorber may be 2-hydroxy-2-methyl-4'-2-[p-(3-oxobutyl)phenoxy]propiophenone.

Although the colorant and the ultraviolet radiation transorber have been described as separate compounds, they can be part of the same molecule. For example, they can be covalently coupled to each other, either directly, or indirectly through a relatively small molecule, or spacer. Alternatively, the colorant and ultraviolet radiation transorber can be covalently coupled to a large molecule, such as an oligomer or a polymer. Further, the colorant and ultraviolet radiation transorber may be associated with a large molecule by van der Waals forces, and hydrogen bonding, among other means. Other variations will be readily apparent to those having ordinary skill in the art. For example, in an embodiment of the composition of the present invention, the composition further comprises a molecular includant. Thus, the cavity in the molecular includant can be a tunnel through the molecular includant or a cave-like space or a dented-in space in the molecular includant. The cavity can be isolated or independent, or connected to one or more other cavities.

The molecular includant can be inorganic or organic in nature. In certain embodiments, the chemical structure of the molecular includant is adapted to form a molecular inclusion complex. Examples of molecular includants are, by way of illustration only, clathrates or intercalates, zeolites, and cyclodextrins. Examples of cyclodextrins include, but are not limited to, α-cyclodextrin, β-cyclodextrin, γ-cyclodextrin, hydroxypropyl β-cyclodextrin, hydroxyethyl β-cyclodextrin, sulfated β-cyclodextrin, hydroxyethyl α cyclodextrin, carboxymethyle α cyclodextrin, carboxymethyl β cyclodextrin, carboxymethyl γ cyclodextrin, octyl succinated α cyclodextrin, octyl succinated β cyclodextrin, octyl succinated γ cyclodextrin and sulfated β and γ-cyclodextrin (American Maize-Products Company, Hammond, Ind.).

A desirable molecular includant is a cyclodextrin. More particularly, in some embodiments, the molecular includant is an α-cyclodextrin. In other embodiments, the molecular includant is a β-cyclodextrin. Although not wanting to be bound by the following theory, it is believed that the closer the transorber molecule is to the mutable colorant on the molecular includant, the more efficient the interaction with the colorant to effect mutation of the colorant. Thus, the molecular includant with functional groups that can react with and bind the transorber molecule and that are close to the binding site of the mutable colorant are the more desirable molecular includants.

In some embodiments, the colorant and the ultraviolet radiation transorber are associated with the molecular includant. The term "associated", in its broadest sense, means that the colorant and the ultraviolet radiation transorber are at least in close proximity to the molecular includant. For example, the colorant and/or the ultraviolet radiation transorber can be maintained in close proximity to the molecular includant by hydrogen bonding, van der Waals forces, or the like. Alternatively, either or both of the colorant and the ultraviolet radiation transorber can be covalently bonded to the molecular includant. In certain embodiments, the colorant will be associated with the molecular includant by means of hydrogen bonding and/or van der Waals forces or the like, while the ultraviolet radiation transorber is covalently bonded to the molecular includant. In other embodiments, the colorant is at least partially included within the cavity of the molecular includant, and the ultraviolet radiation transorber is located outside of the cavity of the molecular includant.

In one embodiment wherein the colorant and the ultraviolet radiation transorber are associated with the molecular includant, the colorant is crystal violet, the ultraviolet radiation transorber is a dehydrated phthaloylglycine-2959, and the molecular includant is β-cyclodextrin. In yet another embodiment wherein the colorant and the ultraviolet radiation transorber are associated with the molecular includant, the colorant is crystal violet, the ultraviolet radiation transorber is 4(4-hydroxyphenyl) butan-2-one-2959 (chloro substituted), and the molecular includant is β-cyclodextrin.

Figure 2:
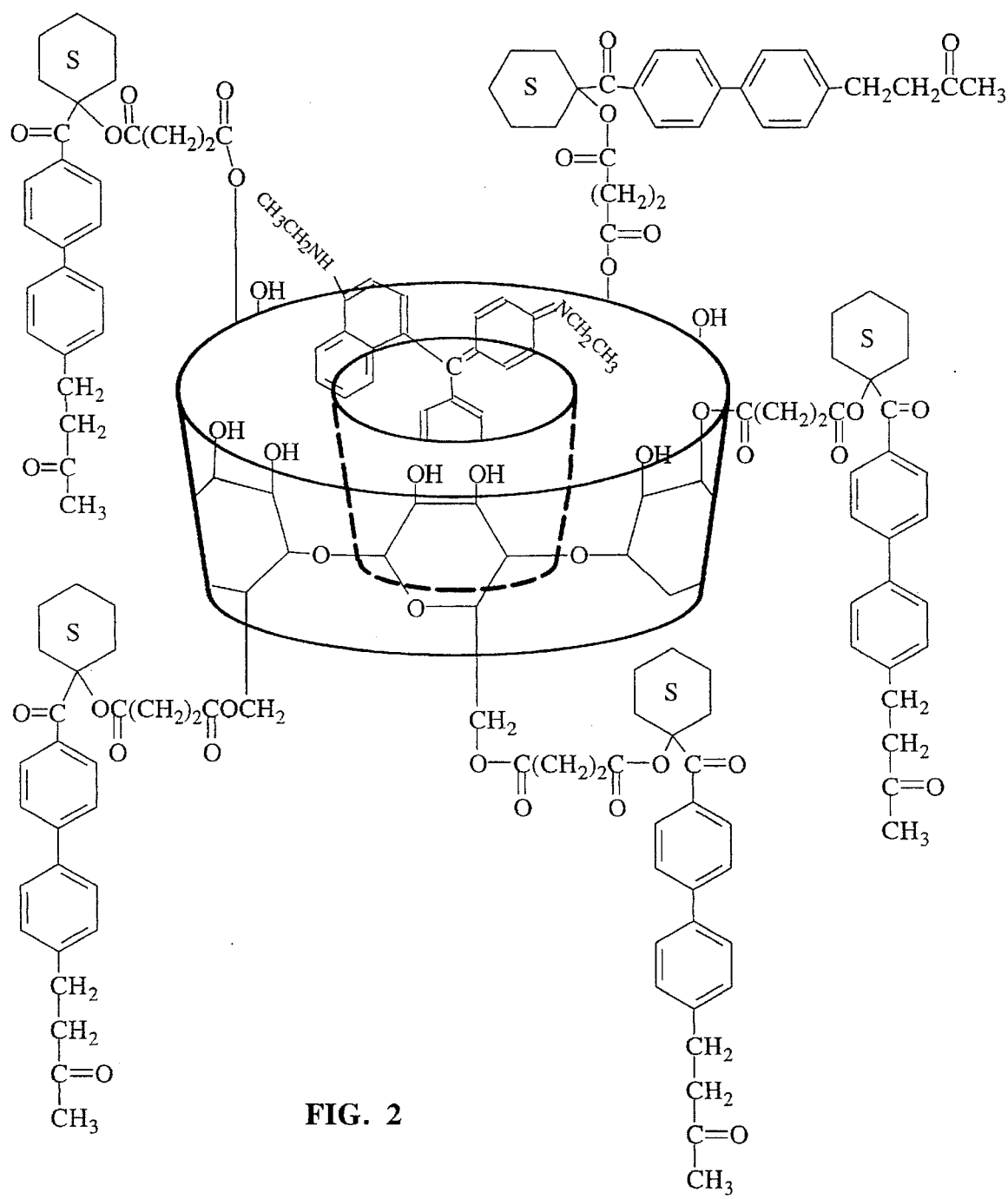
FIG. 2 illustrates an ultraviolet radiation transorber mutable colorant/molecular includant complex wherein the mutable colorant is Victoria Pure Blue BO (Basic Blue 7), the ultraviolet radiation transorber is IRGACURE 184 (1-hydroxycyclohexyl phenyl ketone), and the molecular includant is β-cyclodextrin.

In another embodiment wherein the colorant and the ultraviolet radiation transorber are associated with the molecular includant, the colorant is malachite green, the ultraviolet radiation transorber is IRGACURE 184, and the molecular includant is β-cyclodextrin as shown in FIG. 1. In still another embodiment wherein the colorant and the ultraviolet radiation transorber are associated with the molecular includant, the colorant is Victoria Pure Blue BO, the ultraviolet radiation transorber is IRGACURE 184, and the molecular includant is β-cyclodextrin as shown in FIG. 2.

The present invention also relates to a method of mutating the colorant in the composition of the present invention. Briefly described, the method comprises irradiating a composition containing a mutable colorant and a radiation transorber with radiation at a dosage level sufficient to mutate the colorant. As stated above, in one embodiment the composition further includes a molecular includant. In another embodiment, the composition is applied to a substrate before being irradiated with ultraviolet radiation.

The composition of the present invention may be irradiated with radiation having a wavelength of between about 4 to about 1,000 nanometers. The radiation to which the composition of the present invention is exposed generally will have a wavelength of from about 4 to about 1,000 nanometers. Thus, the radiation may be ultraviolet radiation, including near ultraviolet and far or vacuum ultraviolet radiation; visible radiation; and near infrared radiation. Desirably, the composition is irradiated with radiation having a wavelength of from about 4 to about 700 nanometers. More desirably, the composition of the present invention is irradiated with ultraviolet radiation having a wavelength of from about 4 to about 400 nanometers. It is more desirable that the radiation has a wavelength of between about 100 to 375 nanometers.

Especially desirable radiation is incoherent, pulsed ultraviolet radiation produced by a dielectric barrier discharge lamp. Even more preferably, the dielectric barrier discharge lamp produces radiation having a narrow bandwidth, i.e., the half width is of the order of approximately 5 to 100 nanometers. Desirably, the radiation will have a half width of the order of approximately 5 to 50 nanometers, and more desirably will have a half width of the order of 5 to 25 nanometers. Most desirably, the half width will be of the order of approximately 5 to 15 nanometers.

The amount or dosage level of ultraviolet radiation that the colorant of the present invention is exposed to will generally be that amount which is necessary to mutate the colorant. The amount of ultraviolet radiation necessary to mutate the colorant can be determined by one of ordinary skill in the art using routine experimentation. Power density is the measure of the amount of radiated electromagnetic power traversing a unit area and is usually expressed in watts per centimeter squared ($W/cm^2$). The power density level range is between approximately 5 $mW/cm^2$ and 15 $mW/cm^2$, more particularly 8 to 10 $mW/cm^2$. The dosage level, in turn, typically is a function of the time of exposure and the intensity or flux of the radiation source which irradiates the colored composition. The latter is affected by the distance of the composition from the source and, depending upon the wavelength range of the ultraviolet radiation, can be affected by the atmosphere between the radiation source and the composition. Accordingly, in some instances it may be appropriate to expose the composition to the radiation in a controlled atmosphere or in a vacuum, although in general neither approach is desired.

With regard to the mutation properties of the present invention, photochemical processes involve the absorption of light quanta, or photons, by a molecule, e.g., the ultraviolet radiation transorber, to produce a highly reactive electronically excited state. However, the photon energy, which is proportional to the wavelength of the radiation, cannot be absorbed by the molecule unless it matches the energy difference between the unexcited, or original, state and an excited state. Consequently, while the wavelength range of the ultraviolet radiation to which the colored composition is exposed is not directly of concern, at least a portion of the radiation must have wavelengths which will provide the necessary energy to raise the ultraviolet radiation transorber to an energy level which is capable of interacting with the colorant.

It follows, then, that the absorption maximum of the ultraviolet radiation transorber ideally will be matched with the wavelength range of the ultraviolet radiation to increase the efficiency of the mutation of the colorant. Such efficiency also will be increased if the wavelength range of the ultraviolet radiation is relatively narrow, with the maximum of the ultraviolet radiation transorber coming within such range. For these reasons, especially suitable ultraviolet radiation has a wavelength of from about 100 to about 375 nanometers. Ultraviolet radiation within this range desirably may be incoherent, pulsed ultraviolet radiation from a dielectric barrier discharge excimer lamp.

The term "incoherent, pulsed ultraviolet radiation" has reference to the radiation produced by a dielectric barrier discharge excimer lamp (referred to hereinafter as "excimer lamp"). Such a lamp is described, for example, by U. Kogelschatz, "Silent discharges for the generation of ultraviolet and vacuum ultraviolet excimer radiation," Pure & Appl. Chem., 62, No. 9, pp. 1667–1674 (1990); and E. Eliasson and U. Kogelschatz, "UV Excimer Radiation from Dielectric-Barrier Discharges," Appl. Phys. B, 46, pp. 299–303 (1988). Excimer lamps were developed originally by ABB Infocom Ltd., Lenzburg, Switzerland. The excimer lamp technology since has been acquired by Haräus Noblelight AG, Hanau, Germany.

The excimer lamp emits radiation having a very narrow bandwidth, i.e., radiation in which the half width is of the order of 5–15 nanometers. This emitted radiation is incoherent and pulsed, the frequency of the pulses being dependent upon the frequency of the alternating current power supply which typically is in the range of from about 20 to about 300 kHz. An excimer lamp typically is identified or referred to by the wavelength at which the maximum intensity of the radiation occurs, which convention is followed throughout this specification. Thus, in comparison with most other commercially useful sources of ultraviolet radiation which typically emit over the entire ultraviolet spectrum and even into the visible region, excimer lamp radiation is substantially monochromatic.

Excimers are unstable molecular complexes which occur only under extreme conditions, such as those temporarily existing in special types of gas discharge. Typical examples are the molecular bonds between two rare gaseous atoms or between a rare gas atom and a halogen atom. Excimer complexes dissociate within less than a microsecond and, while they are dissociating, release their binding energy in the form of ultraviolet radiation. Known excimers, in general, emit in the range of from about 125 to about 360 nanometers, depending upon the excimer gas mixture.

For example, in one embodiment, the colorant of the present invention is mutated by exposure to 222 nanometer excimer lamps. More particularly, the colorant crystal violet is mutated by exposure to 222 nanometer lamps. Even more particularly, the colorant crystal violet is mutated by exposure to 222 nanometer excimer lamps located approximately 5 to 6 centimeters from the colorant, wherein the lamps are arranged in four parallel columns approximately 30 centimeters long. It is to be understood that the arrangement of the lamps is not critical to this aspect of the invention. Accordingly, one or more lamps may be arranged in any configuration and at any distance which results in the colorant mutating upon exposure to the lamp's ultraviolet radiation. One of ordinary skill in the art would be able to determine by routine experimentation which configurations and which distances are appropriate. Also, it is to be understood that different excimer lamps are to be used with different ultraviolet radiation transorbers. The excimer lamp used to mutate a colorant associated with an ultraviolet radiation transorber should produce ultraviolet radiation of a wavelength that is absorbed by the ultraviolet radiation transorber.

In some embodiments, the molar ratio of ultraviolet radiation transorber to colorant generally will be equal to or greater than about 0.5. As a general rule, the more efficient the ultraviolet radiation transorber is in absorbing the ultraviolet radiation and interacting with, i.e., transferring absorbed energy to, the colorant to effect irreversible mutation of the colorant, the lower such ratio can be. Current theories of molecular photo chemistry suggest that the lower limit to such ratio is 0.5, based on the generation of two free radicals per photon. As a practical matter, however, ratios higher than 1 are likely to be required, perhaps as high as about 10. However, the present invention is not bound by any specific molar ratio range. The important feature is that the transorber is present in an amount sufficient to effect mutation of the colorant.

While the mechanism of the interaction of the ultraviolet radiation transorber with the colorant is not totally understood, it is believed that it may interact with the colorant in a variety of ways. For example, the ultraviolet radiation transorber, upon absorbing ultraviolet radiation, may be converted to one or more free radicals which interact with the colorant. Such free radical-generating compounds typically are hindered ketones, some examples of which include, but are not limited to: benzildimethyl ketal (available commercially as IRGACURE 651, Ciba-Geigy Corporation, Hawthorne, N.Y.); 1-hydroxycyclohexyl phenyl ketone (IRGACURE 500); 2-methyl-1-[4-(methylthio)phenyl]-2-morpholino-propan-1-one] (IRGACURE 907); 2-benzyl-2-dimethylamino-1-(4-morpholinophenyl)butan-1-one (IRGACURE 369); and 1-hydroxycyclohexyl phenyl ketone (IRGACURE 184).

Alternatively, the ultraviolet radiation may initiate an electron transfer or reduction-oxidation reaction between the ultraviolet radiation transorber and the colorant. In this case, the ultraviolet radiation transorber may be, but is not limited to, Michler's ketone (p-dimethylaminophenyl ketone) or benzyl trimethyl stannate. Or, a cationic mechanism may be involved, in which case the ultraviolet radiation transorber can be, for example, bis[4-(diphenylsulphonio)phenyl)] sulfide bis(hexafluorophosphate) (Degacure KI85, Ciba-Geigy Corporation, Hawthorne, N.Y.); Cyracure UVI-6990 (Ciba-Geigy Corporation), which is a mixture of bis[4-(diphenylsulphonio)phenyl] sulfide bis(hexafluorophosphate) with related monosulphonium hexafluorophosphate salts; and n5-2,4-(cyclopentadienyl)[1,2,3,4,5,6-n-(methylethyl)benzene]-iron(II) hexafluorophosphate (IRGACURE 261).

With regard to the light stabilizing activity of the present invention, it has been determined that in some embodiments it is necessary to modify a conventional photoreactor to produce the improved light stable composition of the present invention. The simplest form of the improved light stable composition of the present invention includes a colorant admixed with a photoreactor modified as described below. The modified photoreactor may or may not be combined with a wavelength-selective sensitizer. Many conventional photoreactor molecules have a functional group that is α to a carbonyl group. The functional group includes, but is not limited to, hydroxyl groups, ether groups, ketone groups, and phenyl groups.

For example, a preferred radiation transorber that can be used in the present invention is designated phthaloylglycine-2959 and is represented by the following formula:

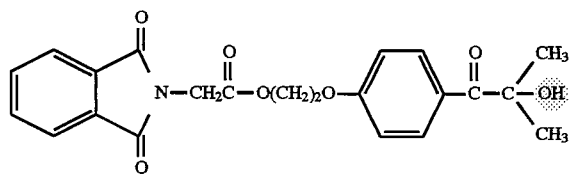

The photoreactor portion of the ultraviolet radiation transorber has a hydroxyl group (shaded portion) α to the carbonyl carbon. The above molecule does not light-stabilize a colorant. However, the hydroxyl group can be removed by dehydration (see Example 4 and 5) yielding the compound represented by the following formula:

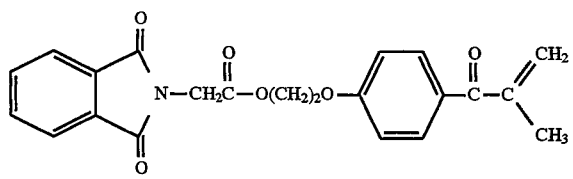

This dehydrated phthaloylglycine-2959 is capable of light-stabilizing a colorant. Thus, it is believed that removal of the functional group α to the carbonyl carbon on any photoreactor molecule will impart the light-stabilizing capability to the molecule. While the dehydrated ultraviolet radiation transorber can impart light-stability to a colorant simply by mixing the molecule with the colorant, it has been found that the molecule is much more efficient at stabilizing colorants when it is attached to an includant, such as cyclodextrin, as described herein.

It is to be understood that stabilization of a colorant can be accomplished according to the present invention by utilizing only the modified photoreactor. In other words, a modified photoreactor without a wavelength selective sensitizer may be used to stabilize a colorant. An example of a photoreactor that is modified according to the present invention is DAROCUR 2959. The unmodified DAROCUR 2959 and the dehydrated DARCUR 2959 are represented by the following formulas:

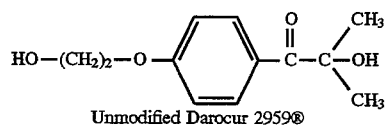
Unmodified Darocur 2959®

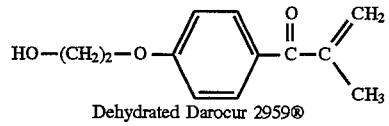
Dehydrated Darocur 2959®

Other photoreactors can be modified according to the present invention to provide stabilizers for dyes. These photoreactors include, but are not limited to: 1-Hydroxy-cyclohexyl-phenyl ketone ("HCPK") (IRGACURE 184, Ciba-Geigy); α,α-dimethoxy-α-hydroxy acetophenone (DAROCUR 1173, Merck); 1-(4-Isopropylphenyl)-2-hydroxy-2-methyl-propan-1-one (DAROCUR 1116, Merck); 1-[4-(2-Hydroxyethoxy)phenyl]-2-hydroxy-2-methyl-propan-1-one (DAROCUR 2959, Merck); Poly[2-hydroxy-2-methyl-1-[4-(1-methylvinyl)phenyl]propan-1-one] (ESACURE KIP, Fratelli Lamberti); Benzoin (2-Hydroxy-1,2-diphenylethanone) (ESACURE BO, Fratelli Lamberti); Benzoin ethyl ether (2-Ethoxy-1,2-diphenylethanone) (DAITOCURE EE, Siber Hegner); Benzoin isopropyl ether (2-Isopropoxy-1,2-diphenylethanone) (VICURE 30, Stauffer); Benzoin n-butyl ether (2-Butoxy-1,2-diphenylethanone) (ESACURE EB1, Fratelli Lamberti); mixture of benzoin butyl ethers (TRIGONAL 14, Akzo); Benzoin iso-butyl ether (2-Isobutoxy-1,2-diphenylethanone) (VICURE 10, Stauffer); blend of benzoin n-butyl ether and benzoin isobutyl ether (ESACURE EB3, ESACURE EB4, Fratelli Lamberti); Benzildimethyl ketal (2,2-Dimethoxy-1,2-diphenylethanone) ("BDK") (IRGACURE 651, Ciba-Geigy); 2,2-Diethoxy-1,2-diphenylethanone (UVATONE 8302, Upjohn); α,α-Diethoxyacetophenone (2,2-Diethoxy-1-phenyl-ethanone) ("DEAP", Upjohn), (DEAP, Rahn); and α,α-Di-(n-butoxy)-acetophenone (2,2-Dibutoxyl-1-phenylethanone) (UVATONE 8301, Upjohn).

It is known to those of ordinary skill in the art that the dehydration by conventional means of the tertiary alcohols that are α to the carbonyl groups is difficult. One conventional reaction that can be used to dehydrate the phthaloylglycine-2959 is by reacting the phthaloylglycine-2959 in anhydrous benzene in the presence of p-toluenesulfonic acid. After refluxing the mixture, the final product is isolated. However, the yield of the desired dehydrated alcohol is only about 15 to 20% by this method.

To increase the yield of the desired dehydrated phthaloylglycine-2959, a new reaction was invented. The reaction is summarized as by the following reaction:

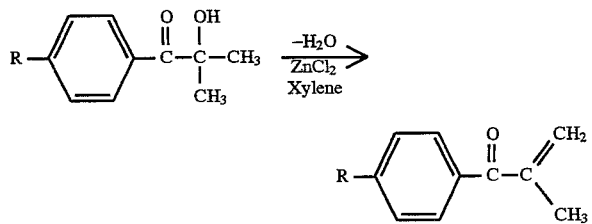

It is to be understood that the groups on the carbon α to the carbonyl group can be groups other than methyl groups such as aryl or heterocyclic groups. The only limitation on these groups are steric limitations. Desirably, the metal salt used in the Nohr-MacDonald elimination reaction is $ZnCl_2$.

It is to be understood that other transition metal salts can be used in performing the Nohr-MacDonald elimination reaction but $ZnCl_2$ is the preferred metal salt. The amount of metal salt used in the Nohr-MacDonald elimination reaction is preferably approximately equimolar to the tertiary alcohol compound, such as the photoreactor. The concentration of tertiary alcohol in the reaction solution is between approximately 4% and 50% w/v.

Thus, the stabilizing composition produced by the process of dehydrating a tertiary alcohol that is a to a carbonyl group on a photoreactor is represented by the following general formula:

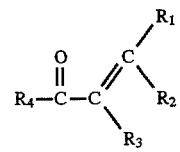

wherein:

$R_1$ is a hydrogen, alkyl, alkenyl, cycloalkyl, heterocycloalkyl, aryl or a heteroaryl group;

$R_2$ is a hydrogen, alkyl, alkenyl, cycloalkyl, heterocycloalkyl, aryl or a heteroaryl group;

$R_3$ is a hydrogen, alkyl, alkenyl, cycloalkyl, heterocycloalkyl, aryl or a heteroaryl group;

$R_4$ is an aryl, heteroaryl, or substituted aryl group.

Another requirement of the reaction is that it be run in a non-aqueous, non-polar solvent. The preferred solvents for running the Nohr-MacDonald elimination reaction are aromatic hydrocarbons including, but not limited to, xylene, benzene, toluene, cumene, mesitylene, p-cymene, butylbenzene, styrene, and divinylbenzene. It is to be understood that other substituted aromatic hydrocarbons can be used as solvents in the present invention. p-Xylene is the preferred aromatic hydrocarbon solvent, but other isomers of xylene can be used in performing the Nohr-MacDonald elimination reaction.

An important requirement in performing the Nohr-MacDonald elimination reaction is that the reaction be run at a relatively high temperature. The reaction is desirably performed at a temperature of between approximately 80° C. and 150° C. A suitable temperature for dehydrating phthaloylglycine-2959 is approximately 124° C. The time the reaction runs is not critical. The reaction should be run between approximately 30 minutes to 4 hours. However, depending upon the reactants and the solvent used, the timing may vary to achieve the desired yield of product.

It is to be understood that the dehydrated phthaloylglycine-2959 can be attached to the molecular includant in a variety of ways. In one embodiment, the dehydrated phthaloylglycine-2959 is covalently attached to the cyclodextrin as represented by the following structure:

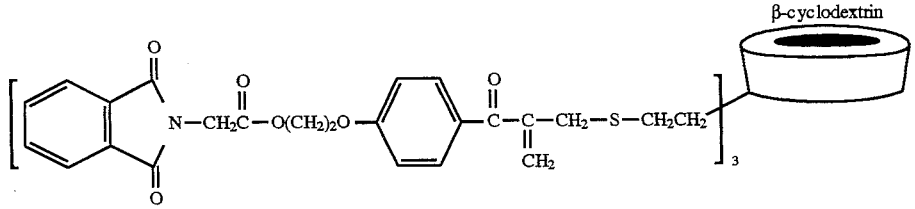

In another embodiment, as shown below, only the modified DAROCUR 2959 without the phthaloyl glycine attached is reacted with the cyclodextrin to yield the following compound. This compound, represented by the following formula, is capable of stabilizing a dye that is associated with the molecular includant.

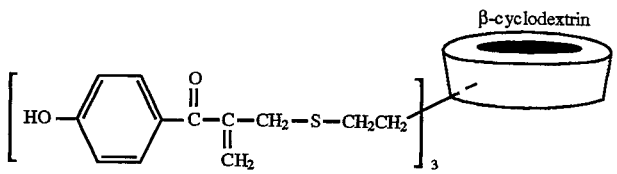

It is to be understood that photoreactors other than DAROCUR 2959 can be used in the present invention.

In yet another embodiment, the dehydrated phthaloylglycine-2959 can be attached to the molecular includant via the opposite end of the molecule. One example of this embodiment is represented by the following formula:

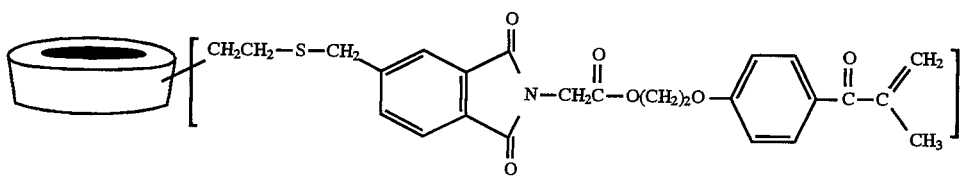

Another stabilizer that is considered part of the present invention is an arylketoalkene represented by the following general formula:

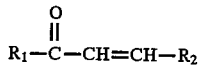

wherein when $R_1$ is an aryl group, $R_2$ is a hydrogen; alkyl; aryl; heterocyclic; or phenyl group, the phenyl group optionally being substituted with an alkyl, halo, amino, or thiol group; and
wherein when $R_2$ is an aryl group, $R_1$ is a hydrogen; alkyl; aryl; heterocyclic; or phenyl group, the phenyl group optionally being substituted with an alkyl, halo, amino, or thiol group.

Preferably, the alkene group is in the trans configuration.

Desirably, the arylketoalkene stabilizing compound is represented by the following formulas:

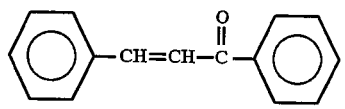

or

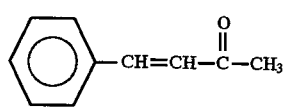

The arylketoalkene may also function as a wavelength-specific sensitizer in the present invention, and it may be associated with any of the previously discussed photoreactors. One method of associating a photoreactor with the arylketoalkene compound of the present invention is described in Example 32. The arylketoalkene compound may optionally be covalently bonded to the reactive species-generating photoinitiator. It is to be understood that the arylketoalkene compound of the present invention is not to be used with photoreactors in a composition where stability in natural sunlight is desired. More particularly, as the arylketoalkene compounds absorb radiation in the range of about 270 to 310 depending on the identity of $R_1$ and $R_2$, then these compounds are capable of absorbing the appropriate radiation from sunlight. Accordingly, these compounds when admixed with a photoreactor can effect a mutation of the colorant upon exposure to sunlight. Where such a change in color is not desired, then a photoreactor is not to be admixed with the arylketoalkene compound of the present invention, and the arylketoalkene compound is to be used with a colorant without a photoreactor.

In the embodiment where the arylketoalkene compound is covalently attached to another molecule, whichever $R_1$ or $R_2$ that is an aryl group will have a group including, but not limited to, a carboxylic acid, an aldehyde group, an amino group, a haloalkyl group, a hydroxyl group, or a thioalkyl group attached thereto to allow the arylketoalkene to be covalently bonded to the other molecule. Accordingly, the arylketoalkene stabilizing compound includes, but is not limited to, the compounds represented by the following formulas:

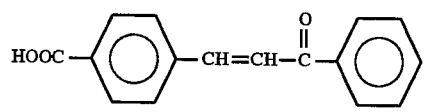

or

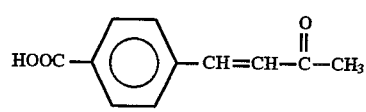

or

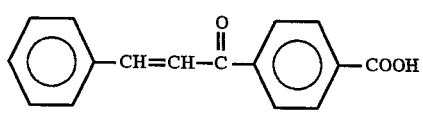

Although it is preferred that the group attached to the aryl group is para to the remainder of the stabilizer molecule, the group may also be ortho or meta to the remainder of the molecule.

Accordingly, this embodiment of the present invention provides a stabilizing arylketoalkene which, when associated with a colorant, stabilizes the colorant. Therefore, the above arylketoalkene can be used as an additive to any colorant composition. For example, as the arylketoalkene compound is not water soluble, it can be directly added to solvent or oil colorant compositions. Additionally, the arylketoalkene compound can be added to other colorant compositions that contain additives enabling the solubilization of the compound therein.

Further, the arylketoalkene stabilizing compounds can be solubilized in aqueous solution by a variety of means. One means of solubilizing the arylketoalkene stabilizing compound of the present invention is to attach the compound to a large water soluble molecule, such as a cyclodextrin, as described in Examples 28 through 31. Desirably, between about 1 and 12 arylketoalkene molecules can be attached to a cyclodextrin molecule. More desirably, between about 4 to about 9 arylketoalkene molecules are attached to a cyclodextrin molecule. Accordingly, the arylketoalkene compound attached to cyclodextrin can be added to any aqueous colorant system to stabilize the colorant therein. It is to be understood that the stabilizing arylketoalkenes do not have to be attached to the molecular includants to exhibit their stabilizing activity.

Therefore, this embodiment provides a method for stabilizing colorant compositions by admixing the aryketoalkene compound with the colorant composition in an amount effective to stabilize the composition. The arylketoalkenes desirably should be present in the colorant medium or solution at a concentration of approximately 0.1 to 50% by weight, desirably between approximately 20% and 30% by weight. If no cyclodextrin is used, the desirable range is approximately 1 part dye to approximately 20 parts arylketoalkene.

Although the arylketoalkene compound need only be associated with the colorant, in some embodiments of the present invention, the arylketoalkene compound may be covalently bonded to the colorant.

Although not wanting to be limited by the following, it is theorized that the arylketoalkene compound of the present invention stabilizes colorants through functioning as a singlet oxygen scavenger. In the alternative, it is theorized that the arylketoalkene compound functions as a stabilizer of a colorant via the resonance of the unshared electron pairs in the p orbitals, e.g., it functions as an energy sink.

As a practical matter, the colorant, ultraviolet radiation transorber, modified photoreactor, arylketoalkene stabilizer, and molecular includant are likely to be solids depending upon the constituents used to prepare the molecules. However, any or all of such materials can be a liquid. The colored composition can be a liquid either because one or more of its components is a liquid, or, when the molecular includant is organic in nature, a solvent is employed. Suitable solvents include, but are not limited to, amides, such as N,N-dimethylformamide; sulfoxides, such as dimethylsulfoxide; ketones, such as acetone, methyl ethyl ketone, and methyl butyl ketone; aliphatic and aromatic hydrocarbons, such as hexane, octane, benzene, toluene, and the xylenes; esters, such as ethyl acetate; water; and the like. When the molecular includant is a cyclodextrin, particularly suitable solvents are the amides and sulfoxides.

In an embodiment where the composition of the present invention is a solid, the effectiveness of the above compounds on the colorant is improved when the colorant and the selected compounds are in intimate contact. To this end, the thorough blending of the components, along with other components which may be present, is desirable. Such blending generally is accomplished by any of the means known to those having ordinary skill in the art. When the colored composition includes a polymer, blending is facilitated if the colorant and the ultraviolet radiation transorber are at least partly soluble in softened or molten polymer. In such case, the composition is readily prepared in, for example, a two-roll mill. Alternatively, the composition of the present invention can be a liquid because one or more of its components is a liquid.

For some applications, the composition of the present invention typically will be utilized in particulate form. In other applications, the particles of the composition should be very small. Methods of forming such particles are well known to those having ordinary skill in the art.

The colored composition of the present invention can be utilized on or in any substrate. If one desires to mutate the colored composition that is present in a substrate, however, the substrate should be substantially transparent to the ultraviolet radiation which is employed to mutate the colorant. That is, the ultraviolet radiation will not significantly interact with or be absorbed by the substrate. As a practical matter, the composition typically will be placed on a substrate, with the most common substrate being paper. Other substrates, including, but not limited to, woven and nonwoven webs or fabrics, films, and the like, can be used, however.

The colored composition optionally may also contain a carrier, the nature of which is well known to those having ordinary skill in the art. For many applications, the carrier will be a polymer, typically a thermosetting or thermoplastic polymer, with the latter being the more common.

Further examples of thermoplastic polymers include, but are not limited to: end-capped polyacetals, such as poly (oxymethylene) or polyformaldehyde, poly (trichloroacetaldehyde), poly(n-valeraldehyde), poly (acetaldehyde), poly(propionaldehyde), and the like; acrylic polymers, such as polyacrylamide, poly(acrylic acid), poly (methacrylic acid), poly(ethyl acrylate), poly(methyl methacrylate), and the like; fluorocarbon polymers, such as poly(tetrafluoroethylene), perfluorinated ethylenepropylene copolymers, ethylenetetrafluoroethylene copolymers, poly (chlorotrifluoroethylene), ethylene-chlorotrifluoroethylene copolymers, poly(vinylidene fluoride), poly(vinyl fluoride), and the like; epoxy resins, such as the condensation products of epichlorohydrin and bisphenol A; polyamides, such as poly(6-aminocaproic acid) or poly(ε-caprolactam), poly (hexamethylene adipamide), poly(hexamethylene sebacamide), poly(11-aminoundecanoic acid), and the like; polyaramides, such as poly(imino-1,3-phenyleneiminoisophthaloyl) or poly(m-phenylene isophthalamide), and the like; parylenes, such as poly-p-xylylene, poly(chloro-p-xylene), and the like; polyaryl ethers, such as poly(oxy-2,6-dimethyl-1,4-phenylene) or poly(p-phenylene oxide), and the like; polyaryl sulfones, such as poly(oxy-1,4-phenylenesulfonyl-1,4-phenyleneoxy-1,4-phenyleneisopropylidene-1,4-phenylene), poly (sulfonyl-1,4-phenyleneoxy-1,4-phenylenesulfonyl-4,4-biphenylene), and the like; polycarbonates, such as poly (bisphenol A) or poly(carbonyldioxy-1,4-phenyleneisopropylidene-1,4-phenylene), and the like; polyesters, such as poly(ethylene terephthalate), poly (tetramethylene terephthalate), poly(cyclohexylene-1,4-dimethylene terephthalate) or poly(oxymethylene-1,4- cyclohexylenemethyleneoxyterephthaloyl), and the like; polyaryl sulfides, such as poly(p-phenylene sulfide) or poly (thio-1,4-phenylene), and the like; polyimides, such as poly (pyromellitimido-1,4-phenylene), and the like; polyolefins, such as polyethylene, polypropylene, poly(1-butene), poly (2-butene), poly(1-pentene), poly(2-pentene), poly(3-methyl-1-pentene), poly(4-methyl-1-pentene), 1,2-poly-1,3-butadiene, 1,4-poly-1,3-butadiene, polyisoprene, polychloroprene, polyacrylonitrile, poly(vinyl acetate), poly (vinylidene chloride), polystyrene, and the like; and copolymers of the foregoing, such as acrylonitrilebutadienestyrene (ABS) copolymers, styrene-n-butylmethacrylate copolymers, ethylene-vinyl acetate copolymers, and the like.

Some of the more commonly used thermoplastic polymers include styrene-n-butyl methacrylate copolymers, polystyrene, styrene-n-butyl acrylate copolymers, styrene-butadiene copolymers, polycarbonates, poly(methyl methacrylate), poly(vinylidene fluoride), polyamides (nylon-12), polyethylene, polypropylene, ethylene-vinyl acetate copolymers, and epoxy resins.

Examples of thermosetting polymers include, but are not limited to, alkyd resins, such as phthalic anhydride-glycerol resins, maleic acid-glycerol resins, adipic acid-glycerol resins, and phthalic anhydride-pentaerythritol resins; allylic resins, in which such monomers as diallyl phthalate, diallyl isophthalate diallyl maleate, and diallyl chlorendate serve as nonvolatile cross-linking agents in polyester compounds; amino resins, such as aniline-formaldehyde resins, ethylene urea-formaldehyde resins, dicyandiamide-formaldehyde resins, melamine-formaldehyde resins, sulfonamide-formaldehyde resins, and urea-formaldehyde resins; epoxy resins, such as cross-linked epichlorohydrinbisphenol A resins; phenolic resins, such as phenol-formaldehyde resins, including Novolacs and resols; and thermosetting polyesters, silicones, and urethanes.

In addition to the colorant, and ultraviolet radiation transorber or functionalized molecular includant, modified photoreactor, arylketoalkene stabilizer, and optional carrier, the colored composition of the present invention also can contain additional components, depending upon the application for which it is intended. Examples of such additional components include, but are not limited to, charge carriers, stabilizers against thermal oxidation, viscoelastic properties modifiers, cross-linking agents, plasticizers, charge control additives such as a quaternary ammonium salt; flow control additives such as hydrophobic silica, zinc stearate, calcium stearate, lithium stearate, polyvinylstearate, and polyethylene powders; and fillers such as calcium carbonate, clay and talc, among other additives used by those having ordinary skill in the art. Charge carriers are well known to those having ordinary skill in the art and typically are polymer-coated metal particles. The identities and amounts of such additional components in the colored composition are well known to one of ordinary skill in the art.

The improved ink jet ink of the present invention comprises a colored composition, as described above, and a liquid vehicle that is compatible with the colored composition. The improved ink may also contain optional additives such as dispersants and humectants.

The liquid vehicle is any liquid solvent or carrier that is compatible with the colored composition such that the improved ink is suitable for use in inks for ink jet printing. For ink to be used in thermal ink jet printers it is desirable that the liquid vehicle is water. Alternatively, the liquid vehicle may comprise a mixture of water and a miscible organic component, such as ethylene glycol, propylene glycol, diethylene glycols, glycerine, dipropylene glycols, polyethylene glycols, polypropylene glycols, amides, ethers, carboxylic acids, esters, alcohols, organosulfides, organosulfoxides, sulfones, alcohol derivative carbitol, butyl carbitol, cellusolve, ether derivatives, amino alcohols, ketones, and other water miscible materials, as well as mixtures thereof. When mixtures of water and water miscible organic liquids are selected as the liquid vehicle, the water to organic ratio may be in any effective range, and typically is from about 100:0 to about 30:70. The non-water component of the liquid vehicle generally serves as a humectant which has a boiling point higher than that of water (100° C.).

The ink of the present invention may contain a non-aqueous liquid vehicle including, but not limited to, isopropanol, methyl ethyl kentone, pentane, hexane, freon 113, dimethysulfoxide, and dimethylformamide. Such non-aqueous-based ink has utility in ink jet printing, particularly when used with continuous stream ink jet printers.

The liquid vehicle is generally present in an amount of from about 85 to about 99.5 percent by weight, and desirably from about 90 to about 99 percent by weight. Typically, the total amount of colorant in the ink compositions of the present invention is from about 0.5 to about 10 percent by weight, desirably from about 2 to about 5 percent by weight, although the amount can be outside of these ranges.

Polymeric additives or dispersants can also be added to the inks of the present invention to enhance the viscosity of the ink. Examples include, but are not limited to, water soluble polymers such as Gum Arabic, polyacrylate salts, polymethacrylate salts, polyvinyl alcohols, hydroxypropylcellulose, hydroxyethylcellulose, polyvinylpyrrolidinone, polyvinylether, starch, polyethyleneoxide, polysaccharides, sodium salt of naphthalene sulfonate formaldehyde copolymer, sodium salt of alkylbenzene sulfonate, sodium salt of dialkylsulfosuccinate, sodium salt of lignosulfonate, sodium alkylene oxide copolymer, sodium salt of alkyletherphosphate, and the like. In addition, polymers such as hydroxypropylpolyethyleneimine (HPPEI-200) or other polyethyleneimine derivatives can be added to the ink. Polymeric additives can be present in the ink of the present invention in any effective amounts, typically from 0 to about 10 percent by weight, and desirably from about 0.01 to about 5 percent by weight.

Other optional additives to the inks of the present invention include, but are not limited to, humectants such as ethylene glycol, diethylene glycol, N-methylpyrrolidinone, propylene glycol, hydroxyethers, ethers, amides, sulfoxides, ketones, lactones, esters, alcohols, and the like, present in an amount of from 0 to about 50 percent by weight, and desirably from about 5 to about 40 percent by weight, and pH controlling agents such as acids or bases, phosphate salts, carboxylate salts, sulfite salts, amine salts, and the like, present in an amount of from 0 to about 10 percent by weight and desirably from about 0.01 to about 2 percent by weight.

With regard to the improved ink of the present invention the colored composition contained therein desirably is a liquid. However, the improved ink may contain a suspension of finely divided solid particles of the colored composition. The ink compositions of the present invention are generally of a viscosity suitable for use in ink jet printing processes. Typically, the ink viscosity is no more than about 5 centipoise, and desirably is from about 1 to about 2.5 centipoise. Ink compositions of the present invention can be prepared by any suitable process. The inks are generally prepared by simple mixing of the ingredients. One process entails mixing all of the ink ingredients together, heating the mixture to a temperature of from about 40° C. to about 55°

C. for a period of from about 2 to about 3 hours, subsequently cooling the mixture to room temperature (typically from about 10° to about 35° C.), and filtering the mixture to obtain an ink.

The present invention is also directed to ink jet printer ink cartridges containing the improved ink described and claimed herein. Any of the ink jet cartridges known in the art may be filled with the improved ink of the present invention. Such cartridges have utility in ink jet printers. The present invention further encompasses ink jet printers having as a component thereof the improved ink, desirably contained in ink jet printer ink cartridges.

The present invention is also directed to a process of ink jet printing comprising causing droplets of the improved ink composition to be ejected in an imagewise pattern onto a substrate. The improved ink of the present invention can be used on a substrate to form images thereon. The colored composition-based ink of the present invention can be utilized on any appropriate substrate. Substrates commonly used in ink jet printers include plain papers such as Xerox Q3 4024 papers, ruled notebook paper, bond paper, silica coated papers, JuJo paper, and the like, transparency materials, fabrics, textile products, plastics, polymeric films, inorganic substrates such as metals and wood, and the like. Films and other substrates commonly used in ink jet printers often have an ink receiving layer coated on one or both sides of the substrate.

In addition to its utility for ink jet printing, the improved colored composition-based ink of the present invention has utility for data processing forms for use with photo-sensing apparatus that detect the presence of indicia at indicia-receiving locations of the form. The data processing forms are composed of a sheet of carrier material and a plurality of indicia-receiving locations on the surface of the sheet. The indicia-receiving locations are defined by an ink containing a colored composition including a mutable colorant and a radiation transorber. The data processing forms of the present invention are disclosed in co-pending U.S. patent application Ser. No. 08/360,501, which is incorporated herein by reference.

Additionally, the present invention also includes a method of storing data utilizing the mutable ink composition of the present composition on a substrate, such as a disc. The colorant is selectively mutated using a laser at the appropriate wavelength to provide the binary information required for storing the information. The present invention is particularly useful for this purpose because the unmutated colorant is stabilized by the radiation transorber and is further stabilized by the optionally included molecular includant.

The colored composition has further utility in a dry imaging process wherein the imaging process utilizes the following three mumble colorants: cyan; magenta; and yellow. These mutable colorants can be layered on the substrate or could even be mixed together and applied as a single layer. Using, for example, laser technology with three lasers at different wavelengths, an image can be created by selectively "erasing" colorants.

The present invention is further described by the examples which follow. Such examples, however, are not to be construed as limiting in any way either the spirit or scope of the present invention. In the examples, all parts are parts by weight unless stated otherwise.

EXAMPLE 1

This example describes the preparation of a β-cyclodextrin molecular includant having (1) an ultraviolet radiation transorber covalently bonded to the cyclodextrin outside of the cavity of the cyclodextrin, and (2) a colorant associated with the cyclodextrin by means of hydrogen bonds and/or van der Waals forces.

A. Friedel-Crafts Acylation of Transorber

A 250-ml, three-necked, round-bottomed reaction flask was fitted with a condenser and a pressure-equalizing addition funnel equipped with a nitrogen inlet tube. A magnetic stirring bar was placed in the flask. While being flushed with nitrogen, the flask was charged with 10 g (0.05 mole) of 1-hydroxycyclohexyl phenyl ketone (IRGACURE 184, Ciba-Geigy Corporation, Hawthorne, N.Y.), 100 ml of anhydrous tetrahydofuran (Aldrich Chemical Company, Inc., Milwaukee, Wis.), and 5 g (0.05 mole) of succinic anhydride (Aldrich Chemical Co., Milwaukee, Wis.). To the continuously stirred contents of the flask then was added 6.7 g of anhydrous aluminum chloride (Aldrich Chemical Co., Milwaukee, Wis.). The resulting reaction mixture was maintained at about 0° C. in an ice bath for about one hour, after which the mixture was allowed to warm to ambient temperature for two hours. The reaction mixture then was poured into a mixture of 500 ml of ice water and 100 ml of diethyl ether. The ether layer was removed after the addition of a small amount of sodium chloride to the aqueous phase to aid phase separation. The ether layer was dried over anhydrous magnesium sulfate. The ether was removed under reduced pressure, leaving 12.7 g (87 percent) of a white crystalline powder. The material was shown to be 1-hydroxycyclohexyl 4-(2 -carboxyethyl)carbonylphenyl ketone by nuclear magnetic resonance analysis.

B. Preparation of Acylated Transorber Acid Chloride

A 250-ml round-bottomed flask fitted with a condenser was charged with 12.0 g of 1-hydroxycyclohexyl 4-(2-carboxyethyl)carbonylphenyl ketone (0.04 mole), 5.95 g (0.05 mole) of thionyl chloride (Aldrich Chemical Co., Milwaukee, Wis.), and 50 ml of diethyl ether. The resulting reaction mixture was stirred at 30° C. for 30 minutes, after which time the solvent was removed under reduced pressure. The residue, a white solid, was maintained at 0.01 Torr for 30 minutes to remove residual solvent and excess thionyl chloride, leaving 12.1 g (94 percent) of 1-hydroxycyclohexyl 4-(2-chloroformylethyl) carbonylphenyl ketone.

C. Covalent Bonding of Acylated Transorber to Cyclodextrin

A 250-ml, three-necked, round-bottomed reaction flask containing a magnetic stirring bar and fitted with a thermometer, condenser, and pressure-equalizing addition funnel equipped with a nitrogen inlet tube was charged with 10 g (9.8 mmole) of β-cyclodextrin (American Maize-Products Company, Hammond, Ind.), 31.6 g (98 mmoles) of 1-hydroxycyclohexyl 4-(2-chloroformylethyl) carbonylphenyl ketone, and 100 ml of N,N-dimethylformamide while being continuously flushed with nitrogen. The reaction mixture was heated to 50° C. and 0.5 ml of triethylamine added. The reaction mixture was maintained at 50° C. for an hour and allowed to cool to ambient temperature. In this preparation, no attempt was made to isolate the product, a β-cyclodextrin to which an ultraviolet radiation transorber had been covalently coupled (referred to hereinafter for convenience as β-cyclodextrin-transorber).

The foregoing procedure was repeated to isolate the product of the reaction. At the conclusion of the procedure as described, the reaction mixture was concentrated in a rotary evaporator to roughly 10 percent of the original volume. The residue was poured into ice water to which sodium chloride then was added to force the product out of solution. The resulting precipitate was isolated by filtration and washed with diethyl ether. The solid was dried under reduced pressure to give 24.8 g of a white powder. In a third preparation, the residue remaining in the rotary evaporator was placed on top of an approximately 7.5-cm column containing about 15 g of silica gel. The residue was eluted with N,N-dimethylformamide, with the eluant being monitored by means of Whatman Flexible-Backed TLC Plates (Catalog No. 05-713-161, Fisher Scientific, Pittsburgh, Pa.) The eluted product was isolated by evaporating the solvent. The structure of the product was verified by nuclear magnetic resonance analysis.

D. Association of Colorant with Cyclodextrin-Transorber-Preparation of Colored Composition To a solution of 10 g (estimated to be about 3.6 mmole) of β-cyclodextrin-transorber in 150 ml of N,N-dimethylformamide in a 250-ml round-bottomed flask was added at ambient temperature 1.2 g (3.6 mmole) of Malachite Green oxalate (Aldrich Chemical Company, Inc., Milwaukee, Wis.), referred to hereinafter as Colorant A for convenience. The reaction mixture was stirred with a magnetic stirring bar for one hour at ambient temperature. Most of the solvent then was removed in a rotary evaporator and the residue was eluted from a silica gel column as already described. The β-cyclodextrin-transorber Colorant A inclusion complex moved down the column first, cleanly separating from both free Colorant A and β-cyclodextrin-transorber. The eluant containing the complex was collected and the solvent removed in a rotary evaporator. The residue was subjected to a reduced pressure of 0.01 Torr to remove residual solvent to yield a blue-green powder.

E. Mutation of Colored Composition

The β-cyclodextrin-transorber Colorant A inclusion complex was exposed to ultraviolet radiation from two different lamps, Lamps A and B. Lamp A was a 222-nanometer excimer lamp assembly organized in banks of four cylindrical lamps having a length of about 30 cm. The lamps were cooled by circulating water through a centrally located or inner tube of the lamp and, as a consequence, they operated at a relatively low temperature, i.e., about 50° C. The power density at the lamp's outer surface typically is in the range of from about 4 to about 20 joules per square meter (J/m$^2$). However, such range in reality merely reflects the capabilities of current excimer lamp power supplies; in the future, higher power densities may be practical. The distance from the lamp to the sample being irradiated was 4.5 cm. Lamp B was a 500-watt Hanovia medium pressure mercury lamp (Hanovia Lamp Co., Newark, N.J.). The distance from Lamp B to the sample being irradiated was about 15 cm.

A few drops of an N,N-dimethylformamide solution of the β-cyclodextrin-transorber Colorant A inclusion complex were placed on a TLC plate and in a small polyethylene weighing pan. Both samples were exposed to Lamp A and were decolorized (mutated to a colorless state) in 15–20 seconds. Similar results were obtained with Lamp B in 30 seconds.

A first control sample consisting of a solution of Colorant A and β-cyclodextrin in N,N-dimethylformamide was not decolorized by Lamp A. A second control sample consisting of Colorant A and 1-hydroxycyclohexyl phenyl ketone in N,N-dimethylformamide was decolorized by Lamp A within 60 seconds. On standing, however, the color began to reappear within an hour.

To evaluate the effect of solvent on decolorization, 50 mg of the β-cyclodextrin-transorber Colorant A inclusion complex was dissolved in 1 ml of solvent. The resulting solution or mixture was placed on a glass microscope slide and exposed to Lamp A for 1 minute. The rate of decolorization, i.e., the time to render the sample colorless, was directly proportional to the solubility of the complex in the solvent, as summarized below.

TABLE 1

| Solvent | Solubility | Decolorization Time |
| --- | --- | --- |
| N,N-Dimethylformamide | Poor | 1 minute |
| Dimethylsulfoxide | Soluble | <10 seconds |
| Acetone | Soluble | <10 seconds |
| Hexane | Insoluble | — |
| Ethyl Acetate | Poor | 1 minute |

Finally, 10 mg of the β-cyclodextrin-transorber Colorant A inclusion complex were placed on a glass microscope slide and crushed with a pestle. The resulting powder was exposed to Lamp A for 10 seconds. The powder turned colorless. Similar results were obtained with Lamp B, but at a slower rate.

EXAMPLE 2

Because of the possibility in the preparation of the colored composition described in the following examples for the acylated transorber acid chloride to at least partially occupy the cavity of the cyclodextrin, to the partial or complete exclusion of colorant, a modified preparative procedure was carded out. Thus, this example describes the preparation of a β-cyclodextrin molecular includant having (1) a colorant at least partially included within the cavity of the cyclodextrin and associated therewith by means of hydrogen bonds and/or van der Waals forces, and (2) an ultraviolet radiation transorber covalently bonded to the cyclodextrin substantially outside of the cavity of the cyclodextrin.

A. Association of Colorant with a Cyclodextrin

To a solution of 10.0 g (9.8 mmole) of β-cyclodextrin in 150 ml of N,N-dimethylformamide was added 3.24 g (9.6 mmoles) of Colorant A. The resulting solution was stirred at ambient temperature for one hour. The reaction solution was concentrated under reduced pressure in a rotary evaporator to a volume about one-tenth of the original volume. The residue was passed over a silica gel column as described in Part C of Example 1. The solvent in the eluant was removed under reduced pressure in a rotary evaporator to give 12.4 g of a blue-green powder, β-cyclodextrin Colorant A inclusion complex.

B. Covalent Bonding of Acylated Transorber to Cyclodextrin Colorant Inclusion Complex—Preparation of Colored Composition A 250-ml, three-necked, round-bottomed reaction flask containing a magnetic stirring bar and fitted with a thermometer, condenser, and pressure-equalizing addition funnel equipped with a nitrogen inlet tube was charged with 10 g (9.6 mmole) of β-cyclodextrin Colorant A inclusion complex, 31.6 g (98 mmoles) of 1-hydroxycyclohexyl 4-(2-chloroformylethyl)carbonylphenyl ketone prepared as described in Part B of Example 1, and 150 ml of N,N-dimethylformamide while being continuously flushed with nitrogen. The reaction mixture was heated to 50° C. and 0.5 ml of triethylamine added. The reaction mixture was maintained at 50° C. for an hour and allowed to cool to ambient temperature. The reaction mixture then was worked up as described in Part A, above, to give 14.2 g of β-cyclodextrin-transorber Colorant A inclusion complex, a blue-green powder.

C. Mutation of Colored Composition

The procedures described in Part E of Example 1 were repeated with the β-cyclodextrin-transorber Colorant A inclusion complex prepared in Part B, above, with essentially the same results.

EXAMPLE 3

This example describes a method of preparing an ultraviolet radiation transorber, 2-[p-(2-methyllactoyl)phenoxy] ethyl 1,3-dioxo-2-isoindolineacetate, designated phthaloylglycine-2959.

The following was admixed in a 250 ml, three-necked, round bottomed flask fitted with a Dean & Stark adapter with condenser and two glass stoppers: 20.5 g (0.1 mole) of the wavelength selective sensitizer, phthaloylglycine (Aldrich Chemical Co., Milwaukee, Wis.); 24.6 g (0.1 mole) of the photoreactor, DARCUR 2959 (Ciba-Geigy, Hawthorne, N.Y.); 100 ml of benzene (Aldrich Chemical Co., Milwaukee, Wis.); and 0.4 g p-toluenesulfonic acid (Aldrich Chemical Co., Milwaukee, Wis.). The mixture was heated at reflux for 3 hours after which time 1.8 ml of water was collected. The solvent was removed under reduced pressure to give 43.1 g of white powder. The powder was recrystallized from 30% ethyl acetate in hexane (Fisher) to yield 40.2 g (93%) of a white crystalline powder having a melting point of 153°–4° C. The reaction is summarized as follows:

IR [NUJOL MULL] $\nu_{max}$ 3440, 1760, 1740, 1680, 1600 cm$^{-1}$ $^1$H NMR [CDCl$_3$] ∂ppm 1.64[s], 4.25[m], 4.49[m], 6.92[m], 7.25[m], 7.86[m], 7.98[m], 8.06[m] ppm

EXAMPLE 4

This example describes a method of dehydrating the phthaloylglycine-2959 produced in Example 3.

The following was admixed in a 250 ml round bottomed flask fitted with a Dean & Stark adapter with condenser: 21.6 g (0.05 mole) phthaloylglycine-2959; 100 ml of anhydrous benzene (Aldrich Chemical Co., Milwaukee, Wis.); and 0.1 g p-toluenesulfonic acid (Aldrich Chemical Co., Milwaukee, Wis.). The mixture was refluxed for 3 hours. After 0.7 ml of water had been collected in the trap, the solution was then removed under vacuum to yield 20.1 g (97%) of a white solid. However, analysis of the white solid showed that this reaction yielded only 15 to 20% of the desired dehydration product. The reaction is summarized as follows:

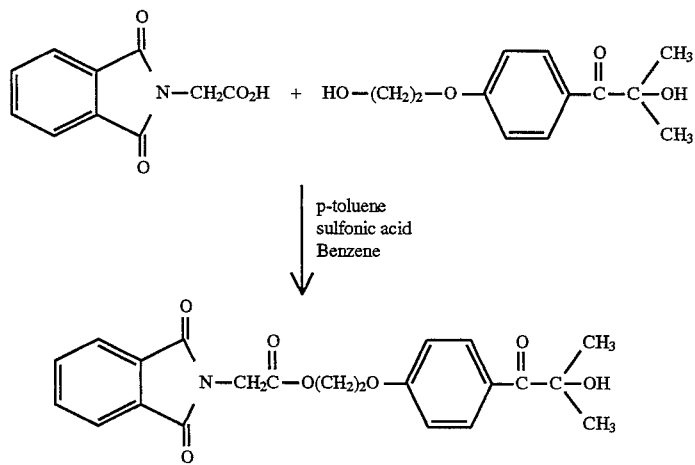

The resulting product, designated phthaloylglycine-2959, had the following physical parameters:

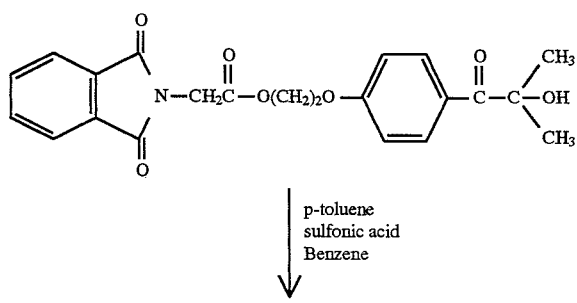

-continued

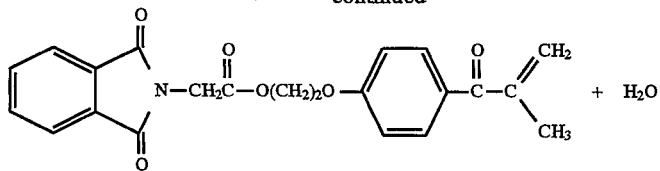

The resulting reaction product had the following physical parameters:

IR (NUJOL) $v_{max}$ 1617 cm$^{-1}$ (C=C—C=O)

EXAMPLE 5

This example describes Nohr-MacDonald elimination reaction used to dehydrate the phthaloylglycine-2959 produced in Example 3.

Into a 500 ml round bottomed flask were placed a stirring magnet, 20.0 g (0.048 mole) of the phthaloylglycine-2959, and 6.6 g (0.048 mole) of anhydrous zinc chloride (Aldrich Chemical Co., Milwaukee, Wis.). 250 ml of anhydrous p-xylene (Aldrich Chemical Co., Milwaukee, Wis.) was added and the mixture refluxed under argon atmosphere for two hours. The reaction mixture was then cooled, resulting in a white precipitate which was collected. The white powder was then recrystallized from 20% ethyl acetate in hexane to yield 18.1 g (95%) of a white powder. The reaction is summarized as follows:

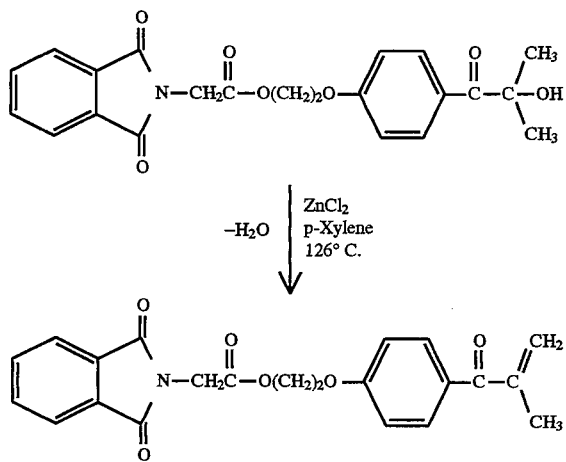

The resulting reaction product had the following physical parameters:

Melting Point: 138° C. to 140° C. Mass spectrum: m/e: 393 M$^+$, 352, 326, 232, 160. IR (KB) $v_{max}$ 1758, 1708, 1677, 1600 cm$^{-1}$ $^1$H NMR [DMSO] ∂ppm 1.8(s), 2.6(s), 2.8(d), 3.8(d), 4.6(m), 4.8(m), 7.3(m), 7.4(m), 8.3(m), and 8.6(d) $^{13}$C NMR [DMSO] ∂ppm 65.9 (CH$_2$=)

EXAMPLE 6

This example describes a method of producing a β-cyclodextrin having dehydrated phthaloylglycine-2959 groups from Example 4 or 5 covalently bonded thereto.

The following was admixed in a 100 ml round-bottomed flask: 5.0 g (4 mmole) β-cyclodextrin (American Maize Product Company, Hammond, Ind.) (designated β-CD in the following reaction); 8.3 g (20 mmole) dehydrated phthaloylglycine-2959; 50 ml of anhydrous DMF; 20 ml of benzene; and 0.01 g p-tolulenesulfonyl chloride (Aldrich Chemical Co., Milwaukee, Wis.). The mixture was chilled in a salt/ice bath and stirred for 24 hours. The reaction mixture was poured into 150 ml of weak sodium bicarbonate solution and extracted three times with 50 ml ethyl ether. The aqueous layer was then filtered to yield a white solid comprising the β-cyclodextrin with phthaloylglycine-2959 group attached. A yield of 9.4 g was obtained. Reverse phase TLC plate using a 50:50 DMF:acetonitrile mixture showed a new product peak compared to the starting materials. The reaction is summarized as follows:

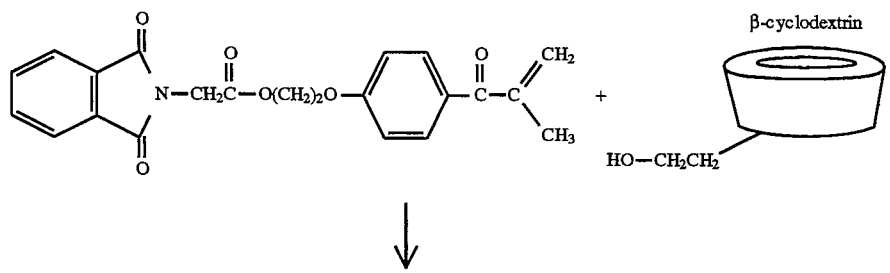

Blue BO is admixed in acetonitrile with phthaloylglycine-2959, represented by the following formula:

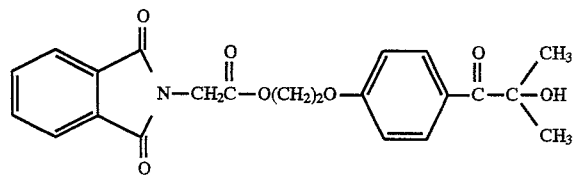

and dehydrated phthaloylglycine-2959, represented by the following formula:

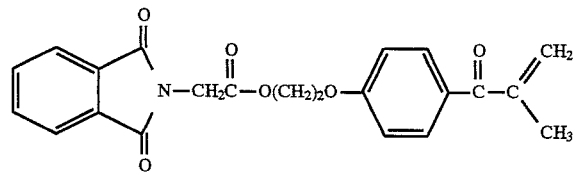

Solutions were prepared according to Table 2. The dye solutions were carefully, uniformly spread on steel plates to a thickness of approximately 0.1 mm. The plates were then immediately exposed to a medium pressure 1200 watt high intensity quartz arc mercury discharge lamp (Conrad-Hanovia, Inc., Newark, N.J.) at a distance of 30 cm from the light. The mercury discharge light is a source of high intensity, broad spectrum light that is used in accelerated fading analyses. Table 2 shows the results of the fade time with the various solutions. Fade time is defined as the time until the dye became colorless to the naked eye.

TABLE 2

| Phthaloyglycine-2959 | Victoria pure Blue BO | Fade Time |
|---|---|---|
| 3 parts by weight | 1 part by weight | 2 min |
| 10 parts by weight | 1 part by weight | 1½ min |
| 20 parts by weight | 1 part by weight | 30 sec |
| Dehydrated Phthaloylglycine-2959 | Victoria pure Blue BO | Fade Time |
| 3 parts by weight | 1 part by weight | 4 min |
| 10 parts by weight | 1 part by weight | 8 min |
| 20 parts by weight | 1 part by weight | >10 min |

As can be seen in Table 2, when phthaloylglycine-2959 was admixed with Victoria Pure Blue BO, the dye faded when exposed to the mercury dwascharge light. However, when dehydrated phthaloylglycine-2959 was admixed with the Victoria Pure Blue BO at a ratio of 10 parts dehydrated phthaloylglycine-2959 to one part Victoria Pure Blue BO, there was increased stabilization of the dye to light. When the ratio was 20 parts dehydrated phthaloylglycine-2959 to one part Victoria Pure Blue BO, the dye was substantially stabilized to the mercury dwascharge light in the time limits of the exposure.

EXAMPLE 10

To determine whether the hydroxy and the dehydroxy 2959 have the capability to stabilize colorants the following experiment was conducted. The two compounds, represented by the following formulas, were tested as described below:

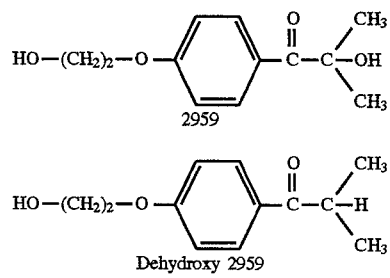

20 parts by weight of the hydroxy and the dehydroxy 2959 were admixed separately to one part by weight of Victoria Pure Blue BO in acetonitrile. The dye solutions were cwerefully uniformly spread on steel plates to a thickness of approximately 0.1 mm. The plates were then immediately exposed to a mercury discharge light at a distance of 30 cm from the light. The mercury discharge tight is a source of high intensity, broad spectrum light that is used in accelerated fading analyses. Table 3 shows the results of the fade time with the various solutions. Fade time is defined as the time until the dye became colorless to the naked eye.

TABLE 3

| Compound | Victoria Blue | Fade Time |
|---|---|---|
| 20 parts 2959 (Hydroxy) | 1 part | <2 min |
| 20 parts 2959 (Dehydroxy) | 1 part | <2 min |
| None | 1 part | <2 min |

EXAMPLE 11

Stabilizing Activity of the Radiation Transorber and a Molecular Includant

This example demonstrates the capability of dehydrated phthaloylglycine-2959 bound to β-cyclodextrin to stabilize dyes against light. The Victoria Pure Blue BO associated with the radiation transorber was tested to determine its capability to stabilize the associated dye against light emitted from a mercury discharge light. In addition, the Victoria Pure Blue BO alone and Victoria Pure Blue BO admixed with β cyclodextrin were tested as controls. The compositions tested were as follows:

1. Victoria Pure Blue BO only at a concentration of 10 mg/ml in acetonitrile.

2. Victoria Pure Blue BO included in β cyclodextrin at a concentration of 20 mg/ml in acetonitrile.

3. The Victoria Pure Blue BO included in β cyclodextrin to which the radiation transorber (dehydrated phthaloylglycine-2959) is covalently attached at a concentration of 20 mg/ml in acetonitrile.

The protocol for testing the stabilizing qualities of the three compositions is as follows: the dye solutions were carefully, uniformly spread on steel plates to a thickness of approximately 0.1 mm. The plates were then immediately exposed to a medium pressure 1200 watt high intensity quartz arc mercury discharge lamp (Conrad-Hanovia, Inc., Newark, N.J.) at a distance of 30 cm from the lamp.

-continued

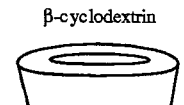
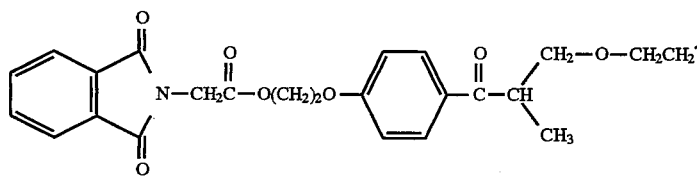

The β-cyclodextrin molecule has several primary alcohols and secondary alcohols with which the phthaloylglycine-2959 can react. The above representative reaction only shows a single phthaloylglycine-2959 molecule for illustrative purposes.

EXAMPLE 7

This example describes a method of associating a colorant and an ultraviolet radiation transorber with a molecular includant. More particularly, this example describes a method of associating the colorant crystal violet with the molecular includant β-cyclodextrin covalently bonded to the ultraviolet radiation transorber dehydrated phthaloylglycine-2959 of Example 6.

The following was placed in a 100 ml beaker: 4.0 g β-cyclodextrin having a dehydrated phthaloylglycine-2959 group; and 50 ml of water. The water was heated to 70° C. at which point the solution became clear. Next, 0.9 g (2.4 mmole) crystal violet (Aldrich Chemical Company, Milwaukee, Wis.) was added to the solution, and the solution Chemical Company, Milwaukee, Wis.); and 100 ml of anhydrous tetrahydrofuran (Aldrich Chemical Company, Milwaukee, Wis.). The mixture was refluxed for 3 hours and the solvent partially removed under reduced pressure (60% taken off). The reaction mixture was then poured into ice water and extracted with two 50 ml aliquots of diethyl ether. After drying over anhydrous magnesium sulfate and removal of solvent, 39.1 g of white solvent remained. Recrystallization of the powder from 30% ethyl acetate in hexane gave 36.7 g (91%) of a white crystalline powder, having a melting point of 142°-3° C. The reaction is summarized in the following reaction:

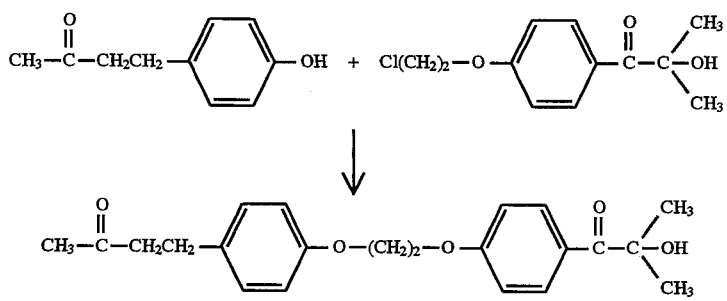

was stirred for 20 minutes. Next, the solution was then filtered. The filter was washed with the filtrate and then dried in a vacuum oven at 84° C. A violet-blue powder was obtained having 4.1 g (92%) yield. The resulting reaction product had the following physical parameters:

U.V. Spectrum DMF $v_{max}$ 610 nm (cf cv $v_{max}$ 604 nm)

EXAMPLE 8

This example describes a method of producing the ultraviolet radiation transorber 4(4-hydroxyphenyl) butan-2-one-2959 (chloro substituted).

The following was admixed in a 250 ml round-bottomed flask fitted with a condenser and magnetic stir bar: 17.6 g (0.1 mole) of the wavelength selective sensitizer, 4(4-hydroxyphenyl) butan-2-one (Aldrich Chemical Company, Milwaukee, Wis.); 26.4 g (0.1 mole) of the photoreactor, chloro substituted DAROCUR 2959 (Ciba-Geigy Corporation, Hawthorne, N.Y.); 1.0 ml of pyridine (Aldrich The resulting reaction product had the following physical parameters:

IR [NUJOL MULL] $v_{max}$ 3460, 1760, 1700, 1620, 1600 cm$^{-1}$ $^1$H[CDCl$_3$] ∂ppm 1.62[s], 4.2[m], 4.5[m], 6.9[m]ppm The ultraviolet radiation transorber produced in this example, 4(4-hydroxyphenyl) butan-2-one-2959 (chloro substituted), may be associated with β-cyclodextrin and a colorant such as crystal violet, using the methods described above wherein 4(4-hydroxyphenyl) butan-2-one-2959 (chloro substituted) would be substituted for the dehydrated phthaloylglycine-2959.

EXAMPLE 9

Stabilizing Activity of the Radiation Transorber

This example demonstrates the ability of the present invention to stabilize colorants against light. Victoria Pure

TABLE 4

| Composition | Fade Time |
|---|---|
| 1 | 5 sec |
| 2 | 5 sec |
| 3 | >10 minutes[a] |

[a]There is a phase change after 10 minutes due to extreme heat

As shown in Table 4, only composition number 3, the Victoria Pure Blue BO included in cyclodextrin with the radiation transorber covalently attached to the β-cyclodextrin was capable of stabilizing the dye under the mercury discharge light.

EXAMPLE 12

Preparation of Epoxide Intermediate of Dehydrated Phthaloylglycine-2959

The epoxide intermediate of dehydrated phthaloylglycine 2959 was prepared according to the following reaction:

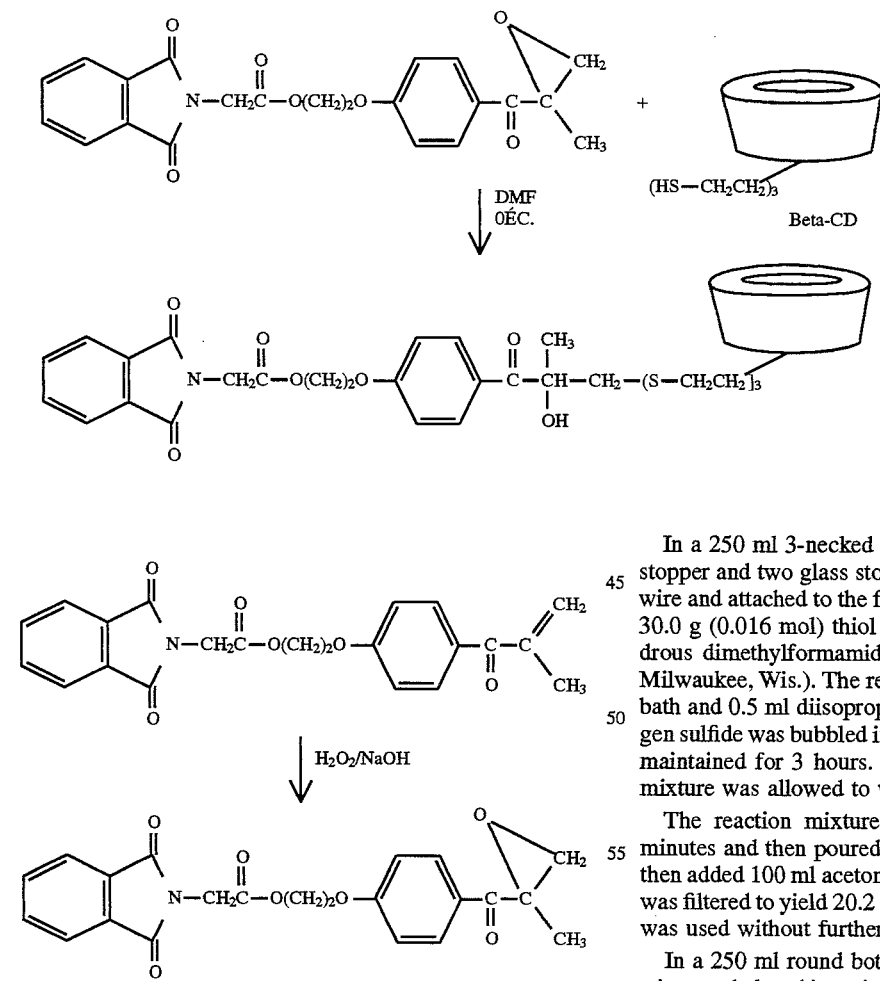

In a 250 ml, three-necked, round bottomed flask fitted with an addition funnel, thermometer and magnetic stirrer was placed 30.0 g (0.076 mol) of the dehydrated phthaloylglycine-2959, 70 ml methanol and 20.1 ml hydrogen peroxide (30% solution). The reaction mixture was stirred and cooled in a water/ice bath to maintain a temperature in the range 15°–20° C. 5.8 ml of a 6N NaOH solution was placed in the addition funnel and the solution was slowly added to maintain the reaction mixture temperature of 15°–20° C. This step took about 4 minutes. The mixture was then stirred for 3 hours at about 20°–25° C. The reaction mixture was then poured into 90 ml of water and extracted with two 70 ml portions of ethyl ether. The organic layers were combined and washed with 100 ml of water, dried with anhydrous $MgSO_4$, filtered, and the ether removed on a rotary evaporator to yield a white solid (yield 20.3 g, 65%). The IR showed the stretching of the C—O—C group and the material was used without further purification.

EXAMPLE 13

Attachment of Epoxide Intermediate to Thiol Cyclodextrin

The attachment of the epoxide intermediate of dehydrated phthaloylglycine 2959 was accomplished by the following reaction:

In a 250 ml 3-necked round bottomed flask fitted with a stopper and two glass stoppers, all being wired with copper wire and attached to the flask with rubber bands, was placed 30.0 g (0.016 mol) thiol cyclodextrin and 100 ml of anhydrous dimethylformamide (DMF) (Aldrich Chemical Co., Milwaukee, Wis.). The reaction mixture was cooled in a ice bath and 0.5 ml diisopropyl ethyl amine was added. Hydrogen sulfide was bubbled into the flask and a positive pressure maintained for 3 hours. During the last hour, the reaction mixture was allowed to warm to room temperature.

The reaction mixture was flushed with argon for 15 minutes and then poured into 70 ml of water to which was then added 100 ml acetone. A white precipitate occurred and was filtered to yield 20.2 g (84.1%) of a white powder which was used without further purification.

In a 250 ml round bottomed flask fitted with a magnetic stirrer and placed in an ice bath was placed 12.7 (0.031 mol), 80 ml of anhydrous DMF (Aldrich Chemical Co., Milwaukee, Wis.) and 15.0 g (0.010 mol) thiol CD. After the reaction mixture was cooled, 0.5 ml of diisopropyl ethyl amine was added and the reaction mixture stirred for 1 hour at 0° C. to 5° C. followed by 2 hours at room temperature. The reaction mixture was then poured into 200 ml of ice water and a white precipitate formed immediately. This was filtered and washed with acetone. The damp white powder was dried in a convection oven at 80° C. for 3 hours to yield a white powder. The yield was 24.5 g (88%).

EXAMPLE 14

Insertion of Victoria Blue in the Cyclodextrin Cavity

In a 250 ml Erlenmeyer flask was placed a magnetic stirrer, 40.0 g (0.014 mol) of the compound and 100 ml water. The flask was heated on a hot plate to 80° C. When the white cloudy mixture became clear, 7.43 g (0.016 mol) of Victoria Pure Blue BO powder was then added to the hot solution and stirred for 10 minutes then allowed to cool to 50° C. The contents were then filtered and washed with 20 ml of cold water.

The precipitate was then dried in a convention oven at 80° C. for 2 hours to yield a blue powder 27.9 g (58.1%).

EXAMPLE 15

The preparation of a tosylated cyclodextrin with the dehydroxy phthaloylglycine 2959 attached thereto is performed by the following reactions:

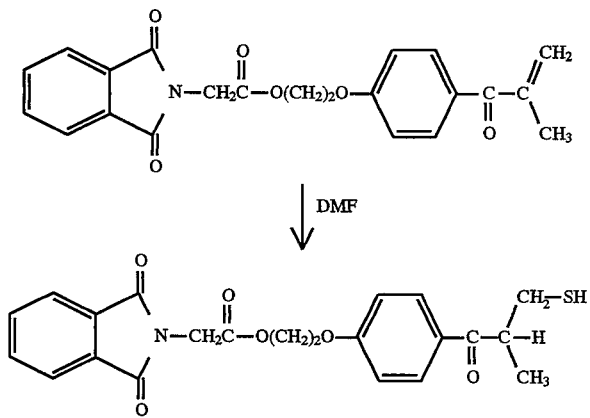

To a 500 ml 3-necked round bottomed flask fitted with a bubble tube, condenser and addition funnel, was placed 10 g (0.025 mole) of the dehydrated phthaloylglycine 2959 in 150 ml of anhydrous N,N-diethylformamide (Aldrich Chemical Co., Milwaukee, Wis.) cooled to 0° C. in an ice bath and stirred with a magnetic stirrer. The synthesis was repeated except that the flask was allowed to warm up to 60° C. using a warm water bath and the H$_2$S pumped into the reaction flask till the stoppers started to move (trying to release the pressure). The flask was then stirred under these conditions for 4 hours. The saturated solution was kept at a positive pressure of H$_2$S. The stoppers were held down by wiring and rubber bands. The reaction mixture was then allowed to warm-up overnight. The solution was then flushed with argon for 30 minutes and the reaction mixture poured onto 50 g of crushed ice and extracted three times (3×80 ml) with diethyl ether (Aldrich Chemical Co., Milwaukee, Wis.).

The organic layers were condensed and washed with water and dried with MgSO$_4$. Removal of the solvent on a rotary evaporator gave 5.2 g of a crude product. The product was purified on a silica column using 20% ethyl acetate in hexane as eluant. 4.5 g of a white solid was obtained.

A tosylated cyclodextrin was prepared according to the following reaction:

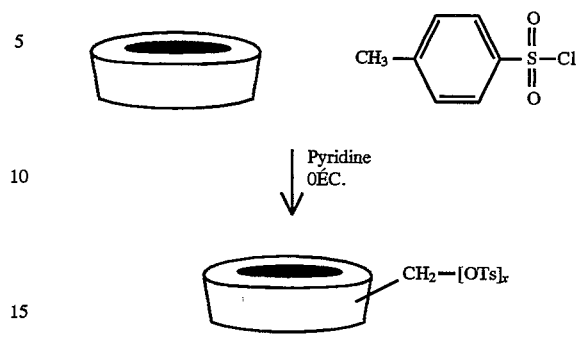

To a 100 ml round bottomed flask was placed 6.0 g β-cyclodextrin (American Maize Product Company), 10.0 g (0.05 mole) p-toluenesulfonyl chloride (Aldrich Chemical Co., Milwaukee, Wis.), 50 ml of pH 10 buffer solution (Fisher). The resultant mixture was stirred at room temperature for 8 hours after which it was poured on ice (approximately 100 g) and extracted with diethyl ether. The aqueous layer was then poured into 50 ml of acetone (Fisher) and the resultant, cloudy mixture filtered. The resultant white powder was then run through a Sephadex column (Aldrich Chemical Co., Milwaukee, Wis.) using n-butanol, ethanol, and water (5:4:3 by volume) as eluant to yield a white powder. The yield was 10.9%.

The degree of substitution of the white powder (tosyl-cyclodextrin) was determined by $^{13}$C NMR spectroscopy (DMF-d6) by comparing the ratio of hydroxysubstituted carbons versus tosylated carbons, both at the 6 position. When the 6-position carbon bears a hydroxy group, the NMR peaks for each of the six carbon atoms are given in Table 5.

TABLE 5

| Carbon Atom | NMR Peak (ppm) |
|---|---|
| 1 | 101.8 |
| 2 | 72.9 |
| 3 | 72.3 |
| 4 | 81.4 |
| 5 | 71.9 |
| 6 | 59.8 |

The presence of the tosyl group shifts the NMR peaks of the 5-position and 6-position carbon atoms to 68.8 and 69.5 ppm, respectively.

The degree of substitution was calculated by integrating the NMR peak for the 6-position tosylated carbon, integrating the NMR peak for the 6-position hydroxy-substituted carbon, and dividing the former by the latter. The integrations yielded 23.6 and 4.1, respectively, and a degree of substitution of 5.9. Thus, the average degree of substitution in this example is about 6.

The tosylated cyclodextrin with the dehydroxy phthaloylglycine 2959 attached was prepared according to the following reaction:

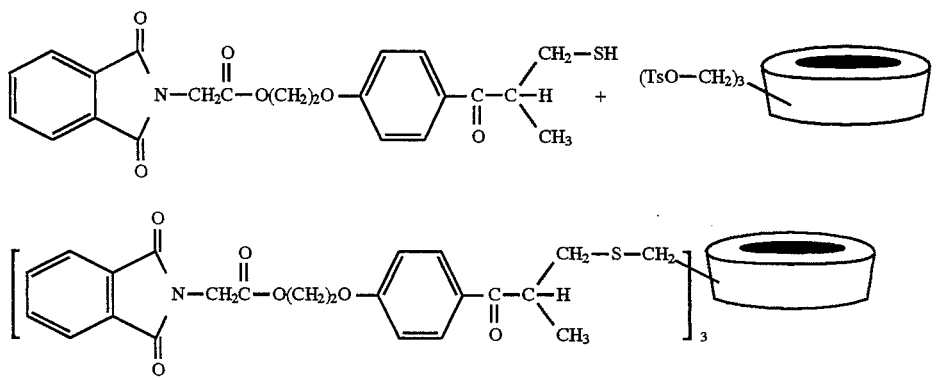

To a 250 ml round bottomed flask was added 10.0 g (4–8 mole) of tosylated substituted cyclodextrin, 20.7 g (48 mmol) thiol in 100 ml of DMF. The reaction mixture was cooled to 0° C. in an ice bath and stirred using a magnetic stirrer. To the solution was slowly dropped in 10 ml of ethyl diisopropylamine (Aldrich Chemical Co., Milwaukee, Wis.) in 20 ml of DMF. The reaction was kept at 0° C. for 8 hours with stirring. The reaction mixture was extracted with diethyl ether. The aqueous layer was then treated with 500 ml of acetone and the precipitate filtered and washed with acetone. The product was then run on a Sephadex column using n-butanol, ethanol, and water (5:4:3 by volume) to yield a white powder. The yield was 16.7 g.

The degree of substitution of the functionalized molecular includant was determined as described above. In this case, the presence of the derivatized ultraviolet radiation transorber shifts the NMR peak of the 6-position carbon atom to 63.1. The degree of substitution was calculated by integrating the NMR peak for the 6-position substituted carbon, integrating the NMR peak for the 6-position hydroxy-substituted carbon, and dividing the former by the latter. The integrations yielded 67.4 and 11.7, respectively, and a degree of substitution of 5.7. Thus, the average degree of substitution in this example is about 6. The reaction above shows the degree of substitution to be "n". Although n represents the value of substitution on a single cyclodextrin, and therefore, can be from 0 to 24, it is to be understood that the average degree of substitution is about 6.

EXAMPLE 16

The procedure of Example 15 was repeated, except that the amounts of β-cyclodextrin and p-toluenesulfonic acid (Aldrich) were 6.0 g and 5.0 g, respectively. In this case, the degree of substitution of the cyclodextrin was found to be about 3.

EXAMPLE 17

The procedure of Example 15 was repeated, except that the derivatized molecular includant of Example 16 was employed in place of that from Example 15. The average degree of substitution of the functionalized molecular includant was found to be about 3.

EXAMPLE 18

This example describes the preparation of a colored composition which includes a mutable colorant and the functionalized molecular includant from Example 15.

In a 250-ml Erlenmeyer flask containing a magnetic stirring bar was placed 20.0 g (5.4 mmoles) of the functionalized molecular includant obtained in Example 15 and 100 g of water. The water was heated to 80° C., at which temperature a clear solution was obtained. To the solution was added slowly, with stirring, 3.1 g (6.0 mmoles) of Victoria Pure Blue BO (Aldrich). A precipitate formed which was removed from the hot solution by filtration. The precipitate was washed with 50 ml of water and dried to give 19.1 g (84 percent) of a blue powder, a colored composition consisting of a mutable colorant, Victoria Pure Blue BO, and a molecular includant having covalently coupled to it an average of about six ultraviolet radiation transorber molecules per molecular includant molecule.

EXAMPLE 19

The procedure of Example 18 was repeated, except that the functionalized molecular includant from Example 17 was employed in place of that from Example 15.

EXAMPLE 20

This example describes mutation or decolorization rates for the compositions of Examples 7 (wherein the β-cyclodextrin has dehydrated phthaloyl glycine-2959 from Example 4 covalently bonded thereto), 18 and 19.

In each case, approximately 10 mg of the composition was placed on a steel plate (Q-Panel Company, Cleveland, Ohio). Three drops (about 0.3 ml) of acetonitrile (Burdick & Jackson, Muskegon, Mich.) was placed on top of the composition and the two materials were quickly mixed with a spatula and spread out on the plate as a thin film. Within 5–10 seconds of the addition of the acetonitrile, each plate was exposed to the radiation from a 222-nanometer excimer lamp assembly. The assembly consisted of a bank of four cylindrical lamps having a length of about 30 cm. The lamps were cooled by circulating water through a centrally located or inner tube of the lamp and, as a consequence, they operated at a relatively low temperature, i.e., about 50° C. The power density at the lamp's outer surface typically was in the range of from about 4 to about 20 joules per square meter ($J/m^2$). However, such range in reality merely reflects the capabilities of current excimer lamp power supplies; in the future, higher power densities may be practical. The distance from the lamp to the sample being irradiated was 4.5 cm. The time for each film to become colorless to the eye was measured. The results are summarized in Table 6.

43

TABLE 6

Decolorization Times for Various Compositions

| Composition | Decolorization Times (Seconds) |
|---|---|
| Example 18 | 1 |
| Example 19 | 3–4 |
| Example 7 | 7–8 |

Figure 3:
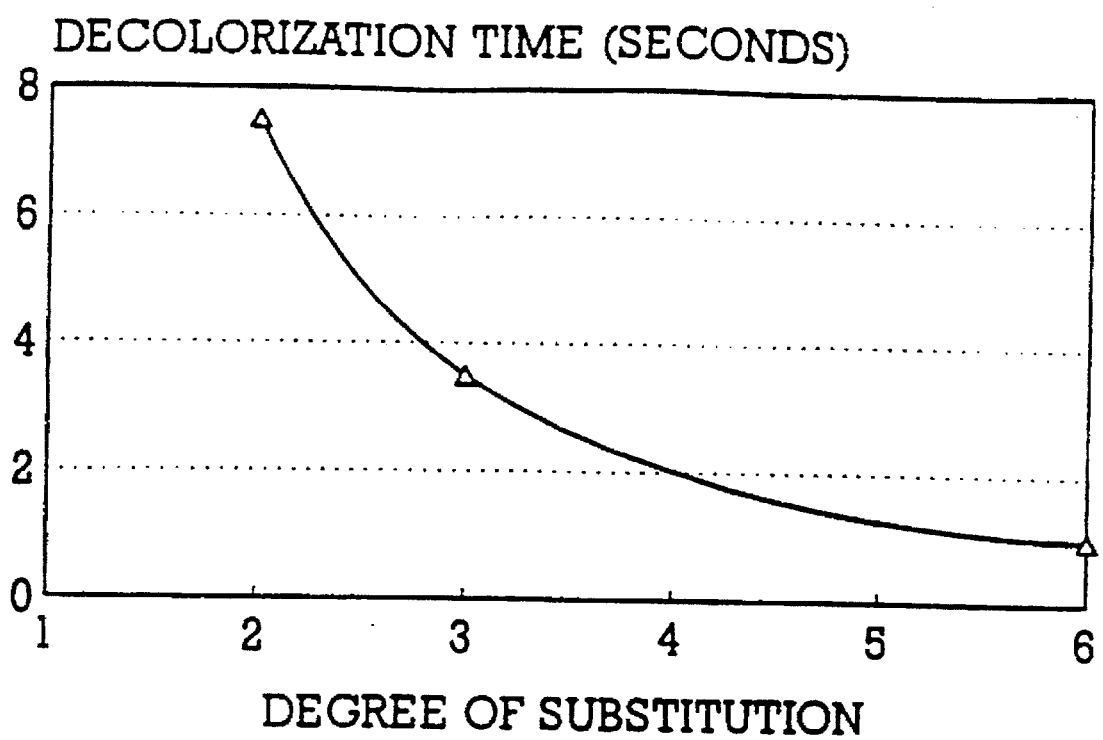
FIG. 3 is a plot of the average number of ultraviolet radiation transorber molecules which are covalently coupled to each molecule of a molecular includant in several colored compositions, which number also is referred to by the term, "degree of substitution," versus the decolorization time upon exposure to 222-nanometer excimer lamp ultraviolet radiation.

While the data in Table 6 demonstrate the clear superiority of the colored compositions of the present invention, such data were plotted as degree of substitution versus decolorization time. The plot is shown in FIG. 3. FIG. 3 not only demonstrates the significant improvement of the colored compositions of the present invention when compared with compositions having a degree of substitution less than three, but also indicates that a degree of substitution of about 6 is about optimum. That is, the figure indicates that little if any improvement in decolonization time would be achieved with degrees of substitution greater than about 6.

EXAMPLE 21

This example describes the preparation of a complex consisting of a mutable colorant and the derivatized molecular includant of Example 15.

The procedure of Example 18 was repeated, except that the functionalized molecular includant of Example 15 was replaced with 10 g (4.8 mmoles) of the derivatized molecular includant of Example 15 and the amount of Victoria Pure Blue BO was reduced to 2.5 g (4.8 mmoles). The yield of washed solid was 10.8 g (86 percent) of a mutable colorant associated with the β-cyclodextrin having an average of six tosyl groups per molecule of molecular includant.

EXAMPLE 22

This example describes the preparation of a colored composition which includes a mutable colorant and a functionalized molecular includant.

The procedure of preparing a functionalized molecular includant of Example 15 was repeated, except that the tosylated β-cyclodextrin was replaced with 10 g (3.8 mmoles) of the complex obtained in Example 21 and the amount of the derivatized ultraviolet radiation transorber prepared in Example 15 was 11.6 g (27 mmoles). The amount of colored composition obtained was 11.2 g (56 percent). The average degree of substitution was determined as described above, and was found to be 5.9, or about 6.

EXAMPLE 23

The two compounds represented in the following formulas were tested for their ability to stabilize Victoria Pure Blue BO:

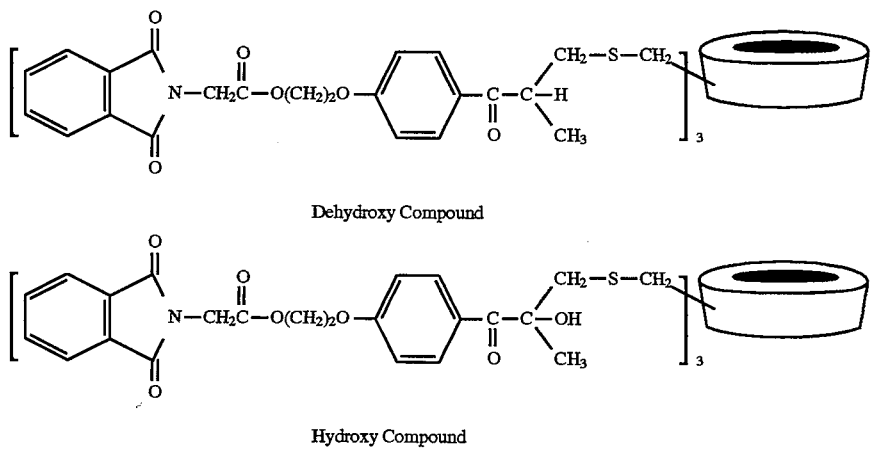

Dehydroxy Compound

Hydroxy Compound

This example further demonstrates the ability of the present invention to stabilize colorants against light. The two compounds containing Victoria Pure Blue BO as an includant in the cyclodextrin cavity were tested for light fastness under a medium pressure mercury discharge lamp. 100 mg of each compound was dissolved in 20 ml of acetonitrile and was uniformly spread on steel plates to a thickness of approximately 0.1 min. The plates were then immediately exposed to a medium pressure 1200 watt high intensity quartz arc mercury discharge lamp (Conrad-Hanovia, Inc., Newark, N.J.) at a distance of 30 cm from the lamp. The light fastness results of these compounds are summarized in Table 7.

TABLE 7

| Cyclodextrin Compound | Fade Time |
|---|---|
| Dehydroxy Compound | >10 min[a] |
| Hydroxy Compound | <20 sec |

[a]There is a phase change after 10 minutes due to extreme heat

EXAMPLE 24

This example describes the preparation of films consisting of colorant, ultraviolet radiation transorber, and thermoplastic polymer. The colorant and ultraviolet radiation transorber were ground separately in a mortar. The desired amounts of the ground components were weighed and placed in an aluminum pan, along with a weighed amount of a thermoplastic polymer. The pan was placed on a hot plate set at 150° C. and the mixture in the pan was stirred until molten. A few drops of the molten mixture were poured onto a steel plate and spread into a thin film by means of a glass microscope slide. Each steel plate was 3×5 inches (7.6 cm×12.7 cm) and was obtained from Q-Panel Company, Cleveland, Ohio. The film on the steel plate was estimated to have a thickness of the order of 10–20 micrometers.

In every instance, the colorant was Malachite Green oxalate (Aldrich Chemical Company, Inc., Milwaukee, Wis.), referred to hereinafter as Colorant A for convenience. The ultraviolet radiation transorber ("UVRT") consisted of one or more of Irgacure® 500 ("UVRT A"), Irgacure® 651 ("UVRT B"), and Irgacure® 907 ("UVRT C"), each of which was described earlier and is available from Ciba-Geigy Corporation, Hawthorne, N.Y. The polymer was one of the following: an epichlorohydrin-bisphenol A epoxy resin ("Polymer A"), Epon® 1004F (Shell Oil Company, Houston, Tex.); a poly(ethylene glycol) having a weight-average molecular weight of about 8,000 ("Polymer B"), Carbowax 8000 (Aldrich Chemical Company); and a poly(ethylene glycol) having a weight-average molecular weight of about 4,600 ("Polymer C"), Carbowax 4600 (Aldrich Chemical Company). A control film was prepared which consisted only of colorant and polymer. The compositions of the films are summarized in Table 8.

TABLE 8

Compositions of Films Containing Colorant and Ultraviolet Radiation Transorber ("UVRT")

| Film | Colorant Type | Colorant Parts | UVRT Type | UVRT Parts | Polymer Type | Polymer Parts |
| --- | --- | --- | --- | --- | --- | --- |
| A | A | 1 | A | 6 | A | 90 |
|   |   |   | C | 4 |   |   |
| B | A | 1 | A | 12 | A | 90 |
|   |   |   | C | 8 |   |   |
| C | A | 1 | A | 18 | A | 90 |
|   |   |   | C | 12 |   |   |
| D | A | 1 | A | 6 | A | 90 |
|   |   |   | B | 4 |   |   |
| E | A | 1 | B | 30 | A | 70 |
| F | A | 1 | — | — | A | 100 |
| G | A | 1 | A | 6 | B | 90 |
|   |   |   | C | 4 |   |   |
| H | A | 1 | B | 10 | C | 90 |

While still on the steel plate, each film was exposed to ultraviolet radiation. In each case, the steel plate having the film sample on its surface was placed on a moving conveyor belt having a variable speed control. Three different ultraviolet radiation sources, or lamps, were used. Lamp A was a 222-nanometer excimer lamp and Lamp B was a 308-nanometer excimer lamp, as already described. Lamp C was a fusion lamp system having a "D" bulb (Fusion Systems Corporation, Rockville, Md.). The excimer lamps were organized in banks of four cylindrical lamps having a length of about 30 cm, with the lamps being oriented normal to the direction of motion of the belt. The lamps were cooled by circulating water through a centrally located or inner tube of the lamp and, as a consequence, they operated at a relatively low temperature, i.e., about 50° C. The power density at the lamp's outer surface typically is in the range of from about 4 to about 20 joules per square meter ($J/m^2$).

However, such range in reality merely reflects the capabilities of current excimer lamp power supplies; in the future, higher power densities may be practical. With Lamps A and B, the distance from the lamp to the film sample was 4.5 cm and the belt was set to move at 20 ft/min (0.1 m/sec). With Lamp C, the belt speed was 14 ft/min (0.07 m/sec) and the lamp-to-sample distance was 10 cm. The results of exposing the film samples to ultraviolet radiation are summarized in Table 9. Except for Film F, the table records the number of passes under a lamp which were required in order to render the film colorless. For Film F, the table records the number of passes tried, with the film in each case remaining colored (no change).

TABLE 9

Results of Exposing Films Containing Colorant and Ultraviolet Radiation Transorber (UVRT) to Ultraviolet Radiation

| Film | Excimer Lamp Lamp A | Excimer Lamp Lamp B | Fusion Lamp |
| --- | --- | --- | --- |
| A | 3 | 3 | 15 |
| B | 2 | 3 | 10 |
| C | 1 | 3 | 10 |
| D | 1 | 1 | 10 |
| E | 1 | 1 | 1 |
| F | 5 | 5 | 10 |
| G | 3 | — | 10 |
| H | 3 | — | 10 |

EXAMPLE 25

Figure 4:
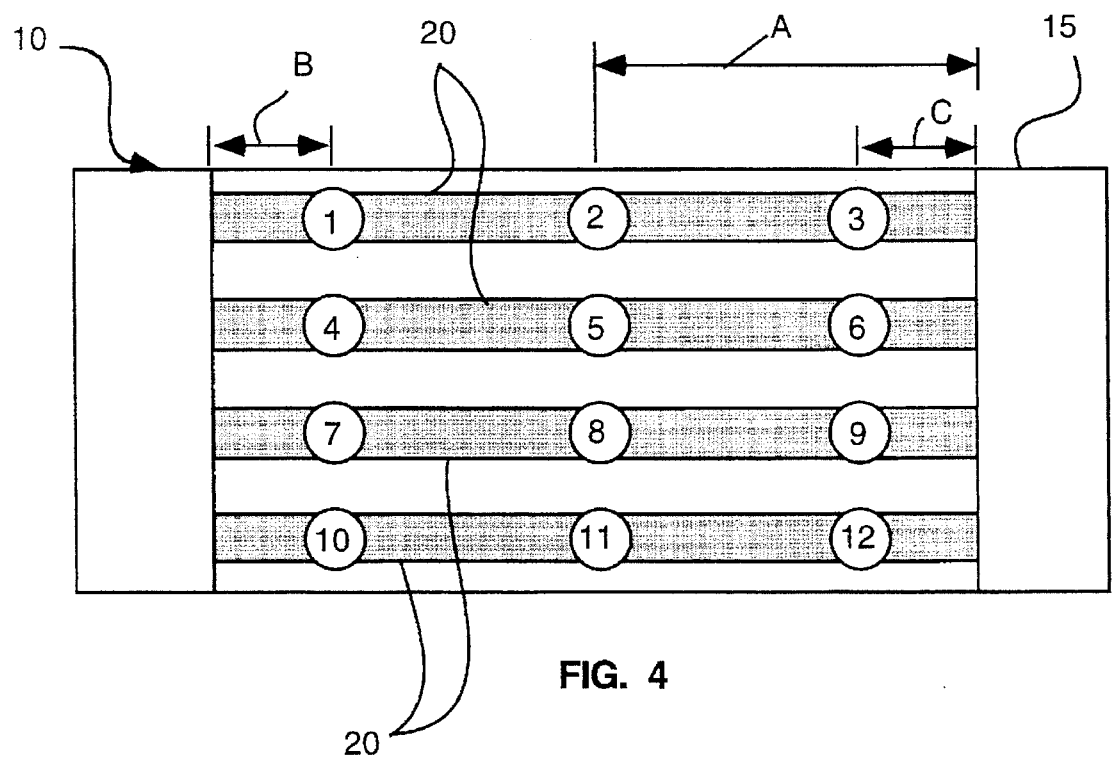
FIG. 4 is an illustration of several 222 nanometer excimer lamps arranged in four parallel columns wherein the twelve numbers represent the locations where twelve intensity measurements were obtained approximately 5.5 centimeters from the excimer lamps.

This Example demonstrates that the 222 nanometer excimer lamps illustrated in FIG. 4 produce uniform intensity readings on a surface of a substrate 5.5 centimeters from the lamps, at the numbered locations, in an amount sufficient to mutate the colorant in the compositions of the present invention which are present on the surface of the substrate. The lamp 10 comprises a lamp housing 15 with four excimer lamp bulbs 20 positioned in parallel, the excimer lamp bulbs 20 are approximately 30 cm in length. The lamps are cooled by circulating water through a centrally located or inner tube (not shown) and, as a consequence, the lamps are operated at a relatively low temperature, i.e., about 50° C. The power density at the lamp's outer surface typically is in the range of from about 4 to about 20 joules per square meter ($J/m^2$).

Table 10 summarizes the intensity readings which were obtained by a meter located on the surface of the substrate. The readings numbered 1, 4, 7, and 10 were located approximately 7.0 centimeters from the left end of the column as shown in FIG. 4. The readings numbered 3, 6, 9, and 12 were located approximately 5.5 centimeters from the right end of the column as shown in FIG. 4. The readings numbered 2, 5, 8, and 11 were centrally located approximately 17.5 centimeters from each end of the column as shown in FIG. 4.

TABLE 10

| Background ($\mu W$) | Reading ($mW/cm^2$) |
| --- | --- |
| 24.57 | 9.63 |
| 19.56 | 9.35 |
| 22.67 | 9.39 |
| 19.62 | 9.33 |
| 17.90 | 9.30 |
| 19.60 | 9.30 |
| 21.41 | 9.32 |
| 17.91 | 9.30 |

TABLE 10-continued

| Background (μW) | Reading (mW/cm²) |
|---|---|
| 23.49 | 9.30 |
| 19.15 | 9.36 |
| 17.12 | 9.35 |
| 21.44 | 9.37 |

EXAMPLE 26

Figure 5:
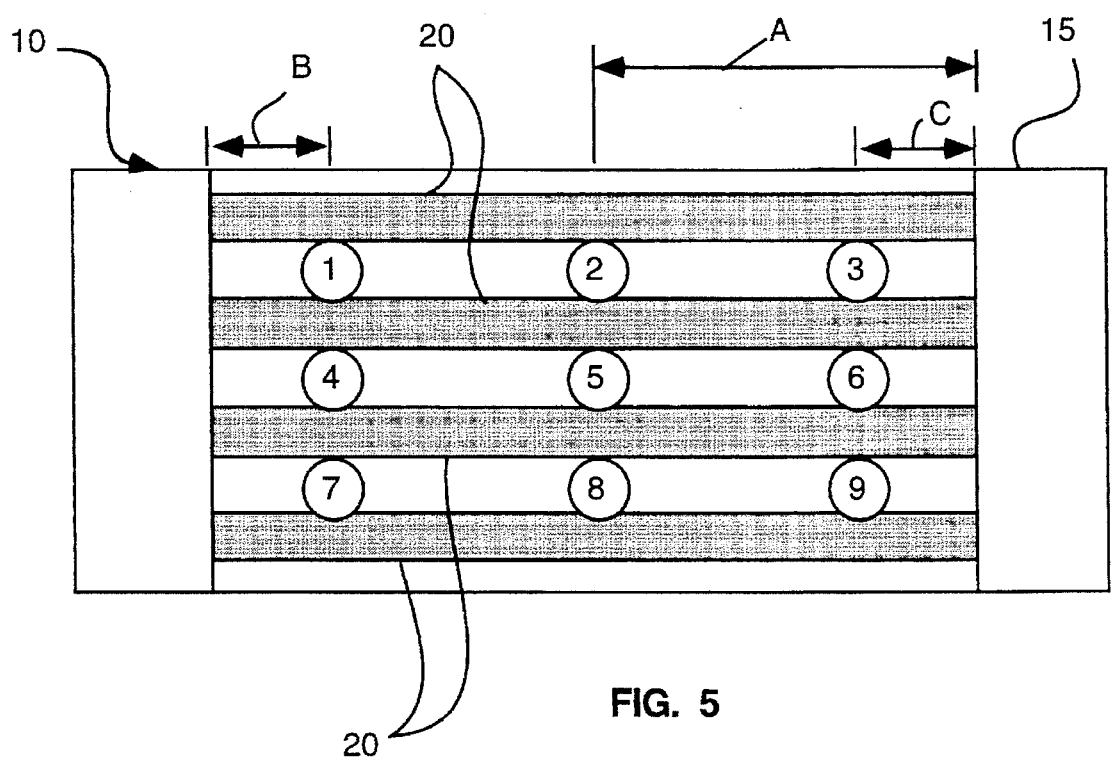
FIG. 5 is an illustration of several 222 nanometer excimer lamps arranged in four parallel columns wherein the nine numbers represent the locations where nine intensity measurements were obtained approximately 5.5 centimeters from the excimer lamps.

This Example demonstrates that the 222 nanometer excimer lamps illustrated in FIG. 5 produce uniform intensity readings on a surface of a substrate 5.5 centimeters from the lamps, at the numbered locations, in an amount sufficient to mutate the colorant in the compositions of the present invention which are present on the surface of the substrate. The excimer lamp 10 comprises a lamp housing 15 with four excimer lamp bulbs 20 positioned in parallel, the excimer lamp bulbs 20 are approximately 30 cm in length. The lamps are cooled by circulating water through a centrally located or inner tube (not shown) and, as a consequence, the lamps are operated at a relatively low temperature, i.e., about 50° C. The power density at the lamp's outer surface typically is in the range of from about 4 to about 20 joules per square meter ($J/m^2$).

Table 11 summarizes the intensity readings which were obtained by a meter located on the surface of the substrate. The readings numbered 1, 4, and 7 were located approximately 7.0 centimeters from the left end of the columns as shown in FIG. 5. The readings numbered 3, 6, and 9 were located approximately 5.5 centimeters from the fight end of the columns as shown in FIG. 5. The readings numbered 2, 5, 8 were centrally located approximately 17.5 centimeters from each end of the columns as shown in FIG. 5.

TABLE 11

| Background (μW) | Reading (mW/cm²) |
|---|---|
| 23.46 | 9.32 |
| 16.12 | 9.31 |
| 17.39 | 9.32 |
| 20.19 | 9.31 |
| 16.45 | 9.29 |
| 20.42 | 9.31 |
| 18.33 | 9.32 |
| 15.50 | 9.30 |
| 20.90 | 9.34 |

EXAMPLE 27

Figure 6:
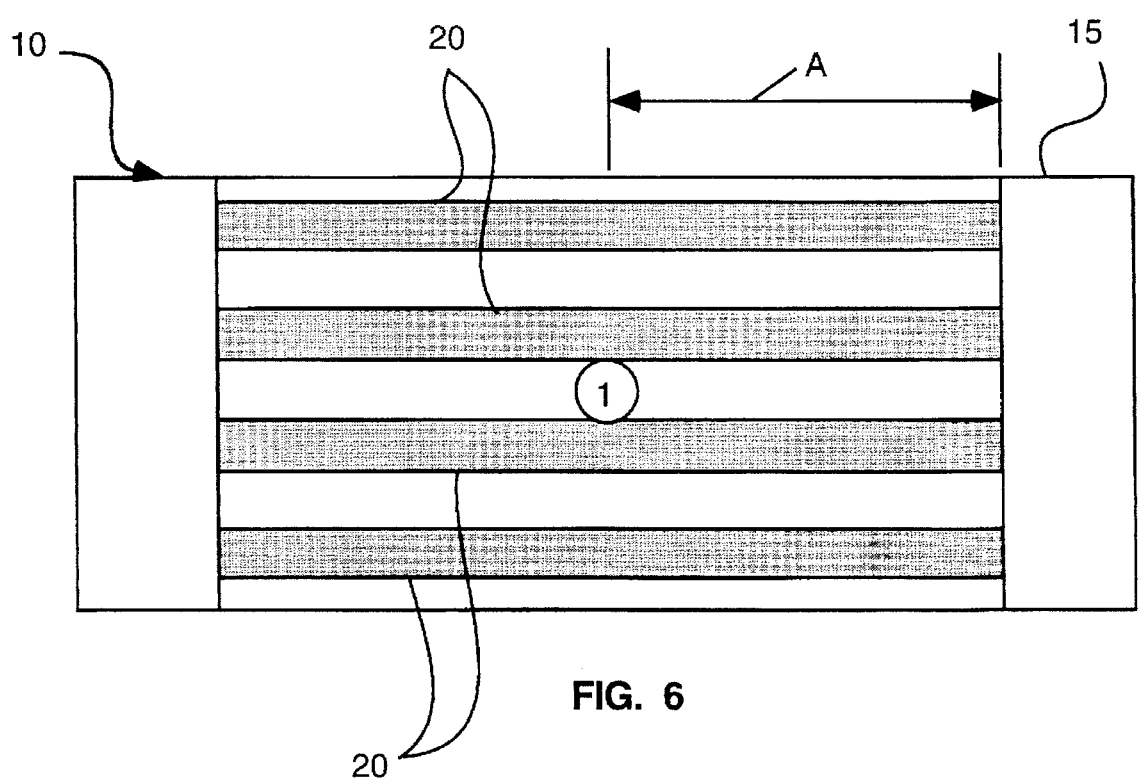
FIG. 6 is an illustration of several 222 nanometer excimer lamps arranged in four parallel columns wherein the location of the number "1" denotes the location where ten intensity measurements were obtained from increasing distances from the lamps at that location. (The measurements and their distances from the lamp are summarized in Table 12.)

This Example demonstrates the intensity produced by the 222 nanometer excimer lamps illustrated in FIG. 6, on a surface of a substrate, as a function of the distance of the surface from the lamps, the intensity being sufficient to mutate the colorant in the compositions of the present invention which are present on the surface of the substrate. The excimer lamp 10 comprises a lamp housing 15 with four excimer lamp bulbs 20 positioned in parallel, the excimer lamp bulbs 20 are approximately 30 cm in length. The lamps are cooled by circulating water through a centrally located or inner tube (not shown) and, as a consequence, the lamps are operated at a relatively low temperature, i.e., about 50° C. The power density at the lamp's outer surface typically is in the range of from about 4 to about 20 joules per square meter ($J/m^2$).

Table 12 summarizes the intensity readings which were obtained by a meter located on the surface of the substrate at position 1 as shown in FIG. 6. Position 1 was centrally located approximately 17 centimeters from each end of the column as shown in FIG. 6.

TABLE 12

| Distance (cm) | Background (μW) | Reading (mW/cm²) |
|---|---|---|
| 5.5 | 18.85 | 9.30 |
| 6.0 | 15.78 | 9.32 |
| 10 | 18.60 | 9.32 |
| 15 | 20.90 | 9.38 |
| 20 | 21.67 | 9.48 |
| 25 | 19.86 | 9.69 |
| 30 | 22.50 | 11.14 |
| 35 | 26.28 | 9.10 |
| 40 | 24.71 | 7.58 |
| 50 | 26.95 | 5.20 |

EXAMPLE 28

This example describes a method of making the wavelength-selective sensitizer represented in the following formula:

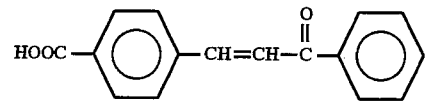

The wavelength-selective sensitizer is synthesized as summarized below:

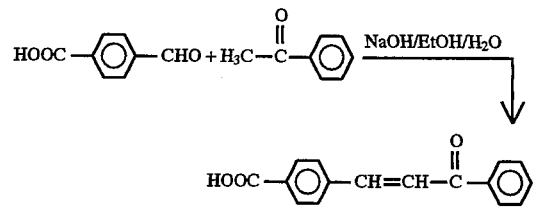

In a 250 ml round bottom flask fitted with a magnetic stir bar, and a condenser, was added 10.8 g (0.27 mole) sodium hydroxide (Aldrich), 98 g water and 50 g ethanol. The solution was stirred while being cooled to room temperature in an ice bath. To the stirred solution was added 25.8 g (0.21 mole) acetophenone (Aldrich) and then 32.2 g (0.21 mole) 4-carboxybenzaldehyde (Aldrich). The reaction mixture was stirred at room temperature for approximately 8 hours. The reaction mixture temperature was checked in order to prevent it from exceeding 30° C. Next, dilute HCL was added to bring the mixture to neutral pH. The white/yellow precipitate was filtered using a Buchner funnel to yield 40.0 g (75%) after drying on a rotary pump for four hours. The product was used below without further purification.

The resulting reaction product had the following physical parameters:

Mass. Spec. m/e (m⁺) 252, 207, 179, 157, 105, 77, 51.

EXAMPLE 29

This example describes a method of covalently bonding the compound produced in Example 28 to cyclodextrin as is summarized below:

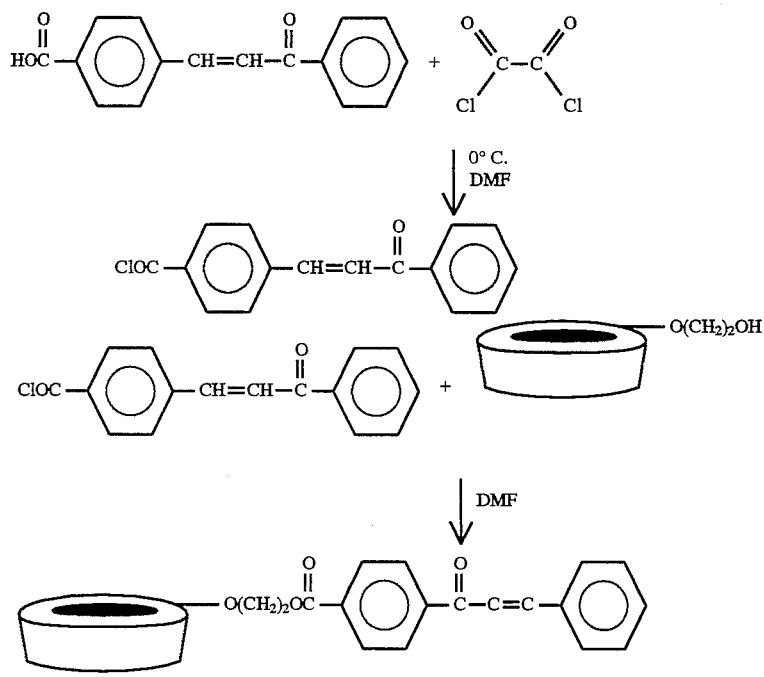

To a 250 ml round bottom flask fitted with a magnetic stir bar, condenser, and while being flushed with argon, was placed 5.0 g (0.019 mole) of the composition prepared in Example 29, and 50 ml of anhydrous DMF (Aldrich). To this solution was slowly dropped in 2.5 g (0.019 mole) oxalyl chloride (Aldrich) over thirty minutes with vigorous stirring while the reaction flask was cooled in an ice-bath. After one hour, the reaction was allowed to warm to room temperature, and then was stirred for one hour. The reaction mixture was used "as is" in the following step. To the above reaction mixture 5.3 g (0.004 mole) of hydroxyethyl substituted α-cyclodextrin (American Maize Company), dehydrated by Dean and Stark over benzene for two hours to remove any water, was added and the reaction mixture stirred at room temperature with 3 drops of triethylamine added. After four hours the reaction mixture was poured into 500 ml of acetone and the white precipitate filtered using a Buchner Funnel. The white powder was dried on a rotary pump (0.1 mm Hg) for four hours to yield 8.2 g product.

The resulting reaction product had the following physical parameters:

NMR (DMSO-d$_6$) 2.80[M, CD], 3.6–4.0[M, CD], 7.9[C, aromatus], 8.2[M, aromatus of C], 8.3[M, aromatus of C] ppm.

EXAMPLE 30

This example describes a method of making the following wavelength-selective sensitizer, namely 4-[4'-carboxy phenyl]-3-buten-2-one:

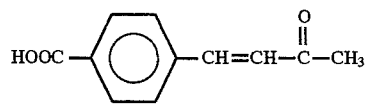

The wavelength-selective sensitizer is synthesized as summarized below:

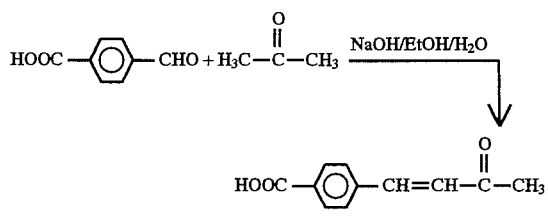

The method of Example 28 was followed except that acetone (Fisher, Optima Grade) was added first, and then the carboxybenzaldehyde was added. More particularly, 32.2 (0.21 mole) of carboxybenzaldehyde was reacted with 12.2 g (0.21 mole) of acetone in the sodium hydroxide/ethanol/water mixture described in Example 28. Dilute HCl was added to bring the reaction mixture to neutral pH, yielding 37.1 g (91%) of a pale yellow powder which was used without further purification in the following examples.

The resulting reaction product, namely 4-[4'-carboxy phenyl]-3-buten-2-one, had the following physical parameters:

Mass. Spec. 190 (m$^+$), 175, 120.

EXAMPLE 31

This example describes a method of covalently bonding the 4-[4'-carboxy phenyl]-3-buten-2-one produced in Example 30 to cyclodextrin as is summarized below:

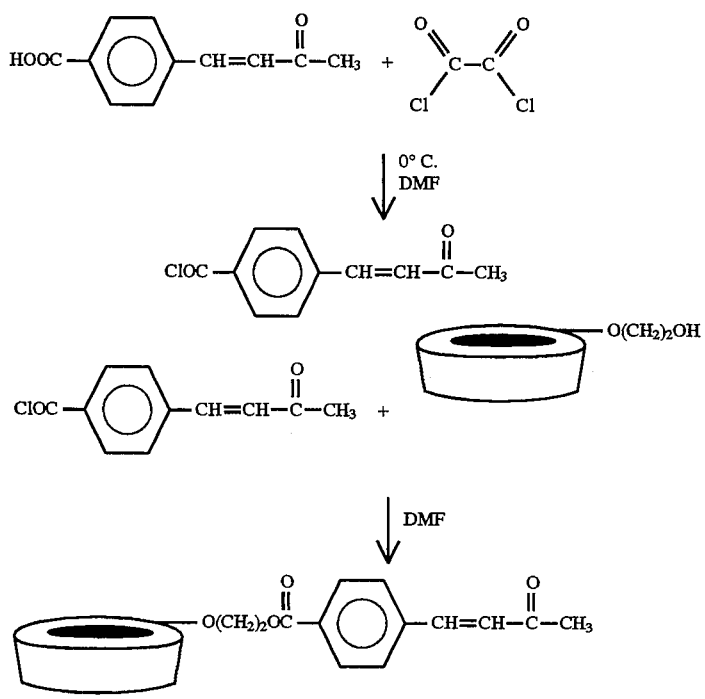

The method of Example 29 was followed except that 5.0 g of the 4-[4'-carboxy phenyl]-3-buten-2-one was used. More particularly, 5.0 g (0.026 mole) of the 4-[4'-carboxy phenyl]-3-buten-2-one produced in Example 30 was reacted with 3.3 g (0.026 mole) of oxalyl chloride in anyhydrous DMF at about 0° C. Next, approximately 7.1 g (0.005 mole) hydroxyethyl substituted cyclodextrin was added to the mixture (5:1 ratio) under the conditions described in Example 30 and was further processed as described therein, to produce 10.8 g of white powder. The NMR of the product showed both the aromatic protons of the 4-[4'-carboxy phenyl]-3-buten-2-one produced in Example 30 and the glucose protons of the cyclodextrin.

EXAMPLE 32

This example describes a method of covalently bonding the compound produced in Example 28 to a photoreactor, namely DAROCUR 2959, as is summarized below:

p-toluenesulphonic acid (Aldrich), and 300 ml anhydrous benzene (Aldrich). The Dean and Stark adapter was put on the flask and the reaction mixture heated at reflux for 8 hours after which point 1.5 ml of water had been collected (theo. 1.43 ml). The reaction mixture was then cooled and the solvent removed on a rotary evaporator to yield 35.4 g. The crude product was recrystalized from 30% ethyl acetate in hexane to yield 34.2 g (94%) of a white powder. The resulting reaction product had the following physical parameters:

Mass. Spectrum: 458(m$^+$), 440, 399, 322, 284.

EXAMPLE 33

To determine whether the 4-[4'-carboxy phenyl]-3-buten-2-one produced in Example 30 has the capability to stabilize colorants, file following experiment was conducted. Test films were made up containing 90% carbowax 4600 and 10% of a 1 part Victoria Blue BO (Aldrich) to 19 parts

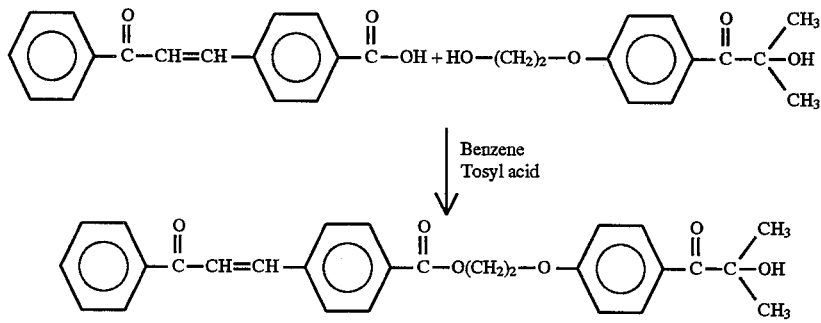

To a 500 ml round bottom flask fitted with a magnetic stir bar, and condenser, was placed 20 g (0.08 mole) of the composition prepared in Example 28, 17.8 g (0.08 mole) DAROCUR 2959 (Ciba-Geigy, New York), 0.5 g 4-[4'-carboxy phenyl]-3-buten-2-one. The mixture was melted on a hot plate, stirred, then drawn down on metal plates (at approximately 60° C.), using a #3 drawdown bar.

A similar sample was made with only 1% Victoria Blue BO in 99% carbowax.

The plates were exposed to a 1200 Watt Mercury medium pressure lamp for one hour, the lamp being about 2 feet from the plates. After one hour, the Victoria Blue BO plate was essentially colorless, while the plate having the mixture of Victoria Blue BO and 4-[4'-carboxy phenyl]-3-buten-2-one thereon had not changed.

EXAMPLE 34

A further experiment to determine the colorant stabilizing capability of the 4-[4'-carboxy phenyl]-3-buten-2-one produced in Example 30 is as follows. The experiment used in Example 33 was repeated except that no carbowax was used. Instead, the materials were dissolved in acetonitrile and a film formed, allowed to dry, and then exposed to the 1200 Watt lamp. Again, after one hour, the dye (Victoria Blue BO) was essentially colorless while the mixture containing the 4-[4'-carboxy phenyl]-3-buten-2-one was unchanged in color.

EXAMPLE 35

A further experiment to determine the colorant stabilizing capability of the compounds produced in Examples 28, 29, 30 (4-[4'-carboxy phenyl]-3-buten-2-one), and 31 (4-[4'-carboxy phenyl]-3-buten-2-one/cyclodextrin) was as follows. The experiment used in Example 34 was repeated for all four compounds, separately. More particularly, five metal plates were prepared using the acetonitrile slurry method of Example 34, with the compositions as follows:

(1) Victoria Pure Blue BO only;

(2) Victoria Pure Blue BO+the compound produced in Example 28;

(3) Victoria Pure Blue BO+the compound produced in Example 30;

(4) Victoria Pure Blue BO+the compound produced in Example 29;

(5) Victoria Pure Blue BO+the compound produced in Example 31.

In compositions (2) through (5), the compositions contained one part Victoria Pure Blue BO per 20 parts of the compounds produced in the above examples. More particularly, 0.1 g of Victoria Pure Blue BO was mixed with approximately 2.0 g of one of the compounds produced in the above examples, in 10 ml of acetonitrile. The mixtures were drawn down using a #8 bar and allowed to air dry in a ventilation hood. All of the plates were simultaneously exposed to the 1200 Watt mercury lamp for one hour. Each plate was half covered with aluminum foil during exposure to the lamp to maintain a reference point with respect to fading of the colorant. After one hour under the lamp, mixture (1) had gone colorless, while mixtures (2) through (5) all remained unchanged.

EXAMPLE 36

Another experiment to determine the colorant stabilizing capability of the compound produced in Example 29 is as follows. Briefly described, the compound of Example 29 was used with color inks removed from the color cartridges of a CANON BJC-600e bubble jet color printer. The ink was re-installed into the cartridges, which were installed into the ink jet printer, and color test pages were generated. The fortieth color test page was used in the present study.

More particularly, the four cartridges were of BJI-201, and the four inks (cyan, magenta, black, and yellow) were prepared as follows:

(1) Cyan

About 3.8 ml of the colored ink in the cartridge was removed, having a viscosity of 12 seconds for 3 ml measured in a 10 ml pipette. About 0.4 g of the compound produced in Example 29 was added to the 3.8 ml and mixed for 15 minutes. The ink solution prepared was hazy, and had a viscosity of 19 seconds for 3 ml.

(2) Magenta

About 4.8 ml of the colored ink in the cartridge was removed, having a viscosity of 12 seconds for 3 ml. About 0.43 g of the compound of Example 29 was added to the 4.8 ml and mixed for fifteen minutes, producing a ink solution having a viscosity of 18 seconds for 3 ml.

(3) Black

About 7.2 ml of the ink in the cartridge was removed, having a viscosity of 8 seconds for 3 ml. About 0.72 g of the compound of Example 29 was added to the 7.2 ml and mixed for fifteen minutes, producing a hazy ink solution having a viscosity of 15 seconds for 3 ml.

(4) Yellow

About 4.0 ml of the colored ink in the cartridge was removed, having a viscosity of 4 seconds for 3 ml. About 0.41 g of the compound of Example 29 was added to the 4.0 ml and mixed for fifteen minutes, producing a hazy ink solution having a viscosity of 7 seconds for 3 ml.

The cartridges were then refilled with the corresponding ink solutions (1) through (4) above. Forty pages were run off, and the fortieth page was exposed to a 1200 Watt medium pressure mercury lamp with a control sheet for nine hours. The control sheet is the fortieth color test page run off using the ink compositions that were in the original ink cartridges.

The results of this experiment are as follows. After three hours under the 1200 Watt lamp, the control was 40 to 50% bleached, while the inks containing the compound produced in Example 29 were unchanged. After nine hours, the control was 50 to 60% bleached while the inks containing the compound of Example 29 were only about 10 to 20% bleached. Accordingly, the compound produced in Example 29 is capable of stabilizing the dyes found in standard ink jet inks.

EXAMPLE 37

Another experiment to determine the colorant stabilizing capability of the compound produced in Example 29 is as follows. The stability of the ink solutions produced in Example 1 were studied as described below.

The forty-eighth sheet (test sheet) was generated using the ink solutions (1) through (4) of Example 36 each containing about 10% of the compound of Example 29, and was then exposed to a 1200 Watt lamp along with a control sheet (generated from the commercially available ink from the cartridges before the compound of Example 29 was added.). The sheets were monitored each hour of exposure and "fade" was determined by the eye against an unexposed sheet. The results of exposing the sheets to the 1200 Watt lamp are summarized in Table 13, where NC=no change.

TABLE 13

| Time (Hour) | Irradiation | |
|---|---|---|
| | Control Sheet | Test Sheet |
| 0 | NC | NC |
| 1 | 5–10% | NC |
| 2 | 10–15% | NC |
| 3 | 20% | NC |
| 4 | 30% | NC |
| 5 | 50% | NC |

Accordingly, the compound prepared in Example 29 works well as a dye stabilizer to visible and ultraviolet radiation.

EXAMPLE 38

An ink composition is prepared by dissolving approximately 2.0 grams of a colored composition comprising a β-cyclodextrin molecular includant having an ultraviolet radiation transorber covalently bonded to the cyclodextrin outside of the cavity of the cyclodextrin and a colored composition associated with the cyclodextrin, as described in the Examples above, in approximately 80.0 grams of deionized water and 5.0 grams of diethylene glycol at approximately 50° C. with constant stirring. The resulting colored composition-containing ink was allowed to cool to room temperature. The ink may be subjected to sonication. Further, a surfactant may be added to the ink formulation. For example, approximately 0.2 gram of surfactant is added dropwise and with constant stirring. Useful surfactant include Strodex PK-'30, obtained from GAF, Pluronic F-68, obtained from BASF, and Karasperse TU, obtained from Marasperse. Still further, the ink may be centrifuged or filtered.

EXAMPLE 39

An ink composition is prepared according to the following proportions:

| | |
|---|---|
| Colored composition as described above | 16% |
| Styrene-maleic anhydride copolymer (dispersant) | 4% |
| Styrene-acrylic resin emulsion, (resin content: 19%) | 25% |
| Diethylene glycol | 5% |
| Ethanol | 5% |
| Water | 45% |

The above components, except diethylene glycol and ethanol are mixed to completely disperse and combine the material. The diethylene glycol and ethanol are then added, and the mixture stirred and filtered through a 5 μm membrane to obtain an ink suitable for ink jet printing.

EXAMPLE 40

An ink composition is prepared according the to following proportions:

| | |
|---|---|
| Colored composition as described above | 8% |
| Styrene-maleic anhydride copolymer (dispersant) | 2% |
| Styrene-acrylic resin emulsion, (resin content: 19%) | 1% |
| Inositol | 10% |
| 2-pyrrolidone | 4% |
| Ethanol | 5% |
| Water | 70% |

The above components, except 2-pyrrolidone and ethanol are mixed to completely disperse and combine the material. The diethylene glycol and ethanol are then added, and the mixture stirred and filtered through a 5 μm membrane to obtain an ink suitable for ink jet printing.

EXAMPLE 41

An ink composition is prepared according the to following proportions:

| | |
|---|---|
| Colored composition as described above | 8% |
| Styrene-acrylic acid copolymer (dispersant) | 1% |
| Styrene-acrylic resin emulsion, (resin content: 19%) | 8% |
| Diethylene glycol | 12% |
| 2-propanol | 3% |
| Water | 68% |

The above components, except diethylene glycol and 2-propanol are mixed to completely disperse and combine the material. The diethylene glycol and ethanol are then added, and the mixture stirred and filtered through a 5 μm membrane to obtain an ink suitable for ink jet printing.

EXAMPLE 42

Ink prepared according to Examples 38–41 is filtered and incorporated into a Hewlett-Packard DeskJet thermal ink jet printer and prints are generated on standard ink jet printer paper.

Having thus described the invention, numerous changes and modifications hereof will be readily apparent to those having ordinary skill in the art, without departing from the spirit or scope of the invention.

What is claimed is:

1. A mutable ink composition suitable for ink jet printing comprising a mixture of:

a colorant;

a radiation transorber;

a molecular includant; and a liquid vehicle;

wherein the radiation transorber comprises a photoreactor covalently bonded to a wavelength selective sensitizer represented by the formula

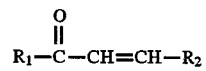

wherein at least one of $R_1$ and $R_2$ is an aryl group; when $R_1$ is an aryl group, $R_2$ is a hydrogen, alkyl, aryl, heterocyclic or phenyl group, the phenyl group optionally being substituted with an alkyl, halo, amino or thiol group; when $R_2$ is an aryl group, $R_1$ is a hydrogen, arkyl, aryl, heterocyclic or phenyl group, the phenyl group optionally being substituted with an akyl, halo, amino or thiol group; and wherein the molecular includant is covalently bonded to the radiation transorber.

2. The mutable ink composition of claim 1, wherein the photoreactor is represented by the following formula

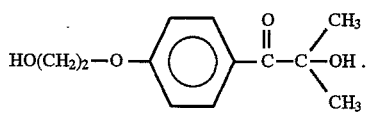

3. The mutable ink jet composition of claim 1, wherein the sensitizer is represented by the following formula

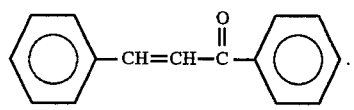

4. The mutable ink composition of claim 1, wherein he sensitizer is represented by the following formula

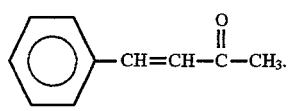

5. The mutable ink composition of claim 1, wherein $R_1$ or $R_2$ is an aryl group having a carboxylic acid group, an aldehyde group, an amino group, a haloalkyl group, a hydroxyl group, or a thioalkyl group attached thereto.

6. The mutable ink composition of claim 5, wherein the sensitizer is represented by the following formula

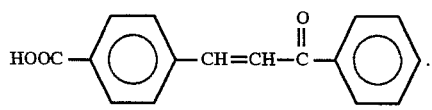

7. The mutable ink composition of claim 5, wherein the sensitizer is represented by the following formula

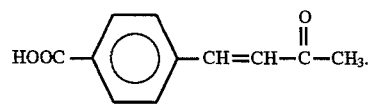

8. The mutable ink composition of claim 5, wherein the sensitizer is represented by the following formula

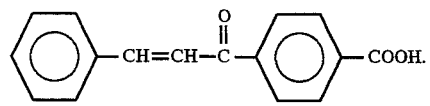

9. The mutable ink composition of claim 1, wherein the molecular includant is selected from the group consisting of clathrates, zeolites and cyclodextrins.

10. The mutable ink composition of claim 9, wherein the cyclodextrin is α-cyclodextrin, β-cyclodextrin, γ-cyclodextrin, hydroxypropyl β-cyclodextrin, hydroethyl β-cyclodextrin, sulfated β-cyclodextrin, hydroxyethyl α-cyclodextrin, carboxymethyl α-cyclodextrin, carboxymethyl β-cyclodextrin, carboxymethyl γ-cyclodextrin, octyl succinated α-cyclodextrin, octyl succinated β-cyclodextrin, octyl succinated γ-cyclodextrin, or sulfated γ-cyclodextrin.

11. The mutable ink composition of claim 10, wherein the molecular includant is β-cyclodextrin.

12. The mutable ink composition of claim 1, wherein the colorant is as least partially included within a cavity of the molecular includant.

13. The mutable ink composition of claim 1, wherein the photoreactor is 1-[4-(2-hydroxyethoxy)-phenyl]-2-hydroxy-2-methylpropan-1-one or 1-hydroxy cyclohexyl phenyl ketone.

14. A mutable ink composition suitable for ink jet printing comprising a mixture of:
   a colorant;
   a radiation transorber; and
   a liquid vehicle;
   wherein the radiation transorber is selected from the group consisting of 2-[p-(2-methyllactoyl)phenoxy] ethyl 1,3-dioxo-2-isoindolineacetate having the following structure

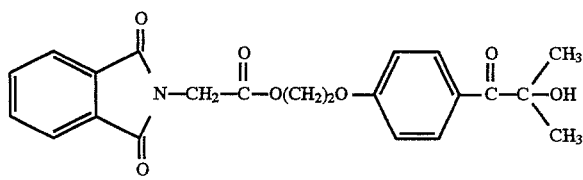

and 2-hydroxy-2-methyl-4'-[2-[p-(3-oxobutyl)phenoxy] ethoxy]-propiophenone having the following structure

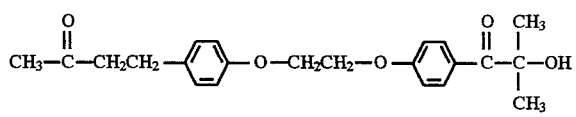

15. A method of printing comprising ejecting droplets of a mutable ink composition onto a substrate from an ink jet printer in an image-wise pattern, said mutable ink composition comprising a mixture of:
   a colorant;
   a radiation transorber;
   a molecular includant; and
   a liquid vehicle;
   wherein the radiation transorber comprises a photoreactor covalently bonded to a wavelength selective sensitizer represented by the formula

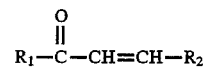

wherein at least one of $R_1$ and $R_2$ is an aryl group; when $R_1$ is an aryl group, $R_2$ is a hydrogen, alkyl, aryl, heterocyclic or phenyl group, the phenyl group optionally being substituted with an alkyl, halo, amino or thiol group; when $R_2$ is an aryl group, $R_1$ is a hydrogen, alkyl, aryl, heterocyclic or phenyl group, the phenyl group optionally being substituted with an akyl, halo, amino or thiol group; and wherein the molecular includant is covalently bonded to the radiation transorber.

16. The method of claim 15, wherein the photoreactor is represented by the following formula

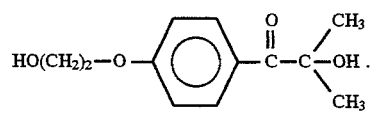

17. The method of claim 15, wherein the sensitizer is represented by the following formula

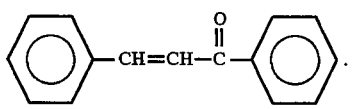

18. The method of claim 15, wherein the sensitizer is represented by the following formula

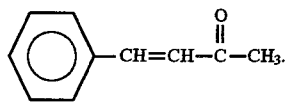

19. The method of claim 15 wherein $R_1$ or $R_2$ is an aryl group having a carboxylic acid group, an aldehyde group, an amino group, a haloalkyl group, a hydroxyl group, or a thioalkyl group attached thereto.

20. The method of claim 19, wherein the sensitizer is represented by the following formula

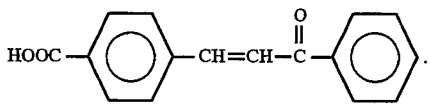

21. The method of claim 19, wherein the sensitizer is represented by the following formula

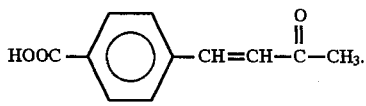

22. The method of claim 19, wherein the sensitizer is represented by the following formula

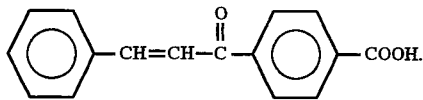

23. The method of claim 15, wherein the molecular includant is selected from the group consisting of clathrates, zeolites and cyclodextrins.

24. The method of claim 15, wherein the photoreactor is 1-[4-(2-hydroxyethoxy)-phenyl]-2-hydroxy-2-methylpropan-1-one or 1-hydroxy cyclohexyl phenyl ketone.

25. A method of printing comprising ejecting droplets of a mutable ink composition onto a substrate from an ink jet printer in an image-wise pattern, said mutable ink composition comprising a mixture of:

a colorant;
a radiation transorber; and
a liquid vehicle;

wherein the radiation transorber is selected from the group consisting of 2-[p-(2-methyllactoyl)phenoxy] ethyl 1,3-dioxo-2-isoindolineacetate having the following structure

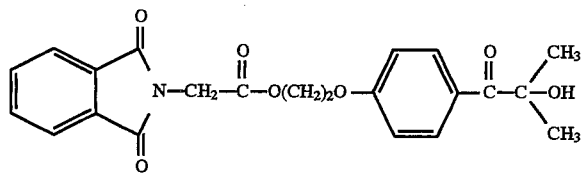

and 2-hydroxy-2-methyl-4'-[2-[p-(3-oxobutyl)phenoxy] ethoxy]-propiophenone having the following structure

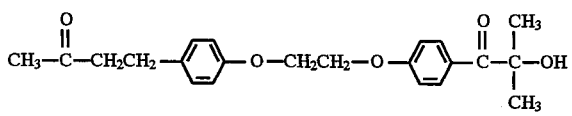

26. An ink jet printer cartridge filled with ink comprising an ink jet print cartridge containing a mutable ink composition therein, said ink composition comprising:

a colorant;
a radiation transorber;
a molecular includant; and
a liquid vehicle;

wherein the radiation transorber comprises a photoreactor covalently bonded to a wavelength selective sensitizer represented by the formula

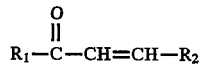

wherein at least one of $R_1$ and $R_2$ is an aryl group; when $R_1$ is an aryl group, $R_2$ is a hydrogen, alkyl, aryl, heterocyclic or phenyl group, the phenyl group optionally being substituted with an alkyl, halo, amino or thiol group; when $R_2$ is an aryl group, $R_1$ is a hydrogen, alkyl, aryl, heterocyclic or phenyl group, the phenyl group optionally being substituted with an akyl, halo, amino or thiol group; and wherein the molecular includant is covalently bonded to the radiation transorber.

* * * * *